US006479255B1

(12) United States Patent
Rubin et al.

(10) Patent No.: US 6,479,255 B1
(45) Date of Patent: Nov. 12, 2002

(54) POLYNUCLEOTIDES ENCODING HUMAN FRP AND FRAGMENTS THEREOF

(75) Inventors: Jeffrey S. Rubin, Rockville, MD (US); Paul Finch, Croton, NY (US); Stuart Aaronson, New York, NY (US); Xi He, Brighton, MA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/087,031

(22) Filed: May 29, 1998

Related U.S. Application Data

(60) Provisional application No. 60/050,417, filed on May 29, 1997, and provisional application No. 60/050,495, filed on Jun. 23, 1997.

(51) Int. Cl.[7] ............................ C12P 21/06; C07H 21/04
(52) U.S. Cl. ...................... 435/69.1; 536/23.5; 530/350; 435/320.1; 435/252.3; 435/6
(58) Field of Search ........................ 536/23.5; 530/350; 435/320.1, 252.3, 6

(56) References Cited

PUBLICATIONS

Paul W. Finch, et al., "Purification And Molecular Cloning of a Secreted, Frizzled—Related Antagonist of Wnt Action", Proc. Natl. Acad. Sci., vol. 94, No. 13, pp. 6770–6775, Jun. 24, 1997.

Adrian N. Salic, et al., "Sizzled: A Secreted Xwnt8 Antagonist Expressed in the Ventral Marginal Zone of Xenopus Embryos", Development, vol. 124 (23), pp. 4739–4748, Dec. 1997.

Hovsep S. Melkonyan, "SARPs: A Family of Secreted Apoptosis–Related Proteins", Proc. Natl. Acad. Sci., vol. 94, No. 25, pp. 13636–13641, Dec. 9, 1997.

Ken M. Cadigan, et al., "Wnt Signaling: A Common Theme in Animal Development", Genes & Development, vol. 11, No. 24, pp. 3286–3305, Dec. 15, 1997.

Jeffrey R. Miller, et al., "Signal Transduction Through β–Catening And Specification of Cell Fate During Embryogenesis", Genes & Development, vol. 10, No. 20, pp. 2527–2539, Oct. 15, 1996.

Bang Hoang, et al., "Primary Structure And Tissue Distribution of FRZB, a Novel Protein Related to Drosphila Frizzled, Suggest a Role in Skeletal Morphogenesis", The Journal of Biological Chemistry, vol. 271, No. 42, pp. 26131–26137, Oct. 18, 1996.

Michio Shirozu, et al., "Characterization of Novel Secreted And Membrane Proteins Isolated by The Signal Sequence Trap Method", Genomics, vol. 37, No. 3, pp. 273–280, Nov. 1, 1996.

Irina D. Karavanova, et al., "Conditioned Medium From a Rat Ureteric Bud Cell Line in Combination With bFGF Induces Complete Differentiation of Isolated Metanephrici Mesenchyme", Development, vol. 122 (12), pp. 4159–4167, Dec. 1996.

Xi He, et al., "A Member of The Frizzled Protein Family Mediating Axis Induction by Wnt–5A", Science, vol. 275, pp. 1652–1654, Mar. 14, 1997.

Luc Leyns, et al., "Frzb–1 is a Secreted Antagonist of wnt Signaling Expressed in The Spemann Organizer", Cell, vol. 88, No. 6, pp. 747–756, Mar. 21, 1997.

Vladimir Korinek, et al., "Constitutive Transcriptional Activation by a β–Catenin–Tcf Complex in APC –/– Colon Carcinoma", Science, vol. 275, pp. 1784–1787, Mar. 21, 1997.

Feliz Mitelman, et al., "A Breakpoint Map of Recurrent Chromosomal Rearrangements in Human Neoplasia", Nature Genetics, vol. 15, pp. 417–419, Apr. 1997.

Amir Rattner, et al., "A Family of Secreted Proteins Contains Homology to the Cystein–Rich Ligand–Binding Domain of Frizzled Receptors", Proc. Natl. Acad. Sci., vol. 94, No. 7, 2859–2863, Apr. 1, 1997.

Kevin Stark, et al., "Epithelial Transformation of Metanephric Mesenchyme in The Developing Kidney Regulated by Wnt–4", Nature, vol. 372, No. 6507, pp. 679–683, Dec. 15, 1994.

Brian A. Parr, et al., "Dorsalizing Signal Wnt–7a Required For Normal Polarity of D–V and A–P Axes of Mouse Limb", Nature, vol. 374, vol. 6520, pp. 350–353, Mar. 23, 1995.

Marko Rehn, et al. "Idenfitication of Three N–Terminal Ends of Type XVIII Collagen Chains And Tissue–Sepcific Differences in The Express of The Corresponding Transcripts", The Journal of Biological Chemistry, vol.. 270, No. 9, pp. 4705–4711, Mar. 3, 1995.

Xi He, et al., "Glycogen Synthase Kinase–3 And Dorsoventral Patterning in Xenoopus Embryos", Nature, vol. 374, No. 6523, pp. 617–622, Apr. 13, 1995.

Zhaoyang Zhao, et al., "A Human Homologue of The Drosophila Polarity Gene Frizzled Has Been Identified And Mapped to 17q21.1", Genomics, vol. 27, No. 2, pp. 370–373, May 20, 1995.

(List continued on next page.)

Primary Examiner—Lorraine Spector
Assistant Examiner—Eileen B. O'Hara
(74) Attorney, Agent, or Firm—Klarquist Sparkman, LLP

(57) ABSTRACT

The invention provides a novel, secreted protein that contains a region homologous to ligand binding domain of a cytokine receptor. This protein, called Frizzled-related protein (FRP), antagonizes the signaling of the Wnt family of cytokines. Extracellular signaling molecules such as the Wnt family members have essential roles as inducers of cellular proliferation, migration, differentiation, and tissue morphogenesis. As Wnt molecules are known to participate in the aberrant growth associated with neoplasia, Wnt antagonists such as FRP are valuable tools which both for understanding oncogenesis and for the design of new cancer therapies.

49 Claims, 18 Drawing Sheets

OTHER PUBLICATIONS

Yanshu Wang, et al., "A Large Family of Putative Transmembrane Receptors Homologous to The Product of The Drosophila Tissue Polarity Gene Frizzled", The Journal of Biological Chemistry, vol. 271, No. 8, pp. 4468–4476, Feb. 23, 1996.

Purnima Bhanot, et al., "A New Member of The Frizzled From Drosophila Functions as a Wingless Receptor", Nature, vol. 382, No. 6588, pp. 225–230, Jul. 18, 1996.

Miranda Molenaar, et al., "XTcf–3 transcription Factor Mediates β–Catenin–Induces Axis Formation in Xenopus Embryos", Cell, vol. 86, No. 3, pp. 391–399, Aug. 9, 1996.

Norbert Perrimon, et al., "Serpentine Proteins Slither Into The Wingless And Hedgehog Fields", Cell, vol. 86, No. 4, pp. 513–516, Aug. 23, 1996.

William C. Smith, et al., "Injected Xwnt–8 RNA Acts Early in Xenopus Embryos to Promote Formation of a Vegetal Dorsalizing Center", Cell, vol. 67, No. 4, pp. 753–765, Nov. 15, 1991.

Kirk R. Thomas, et al., "Swaying is a Mutant Allele of The Proto–Oncogene Wnt–1", Cell, vol. 67, No. 5, pp. 969–976, Nov. 29, 1991.

Arthur Chakrabarti, et al., "Secretory And Inductive Properties of Drosphila Wingless Protein in Xenopus Oocytes And Embryos", Development, vol. 115 (1), pp. 355–369, May 1992.

Michael J. Kelley, et al., "Emergence of The Keratinocyte Growth Factor Multigene Family During The Great Ape Radiation", Proc. Natl. Acad. Sci., vol. 89, No. 19, pp. 9287–9291, Oct. 1, 1992.

Samuel D.H. Chan, et al., "Two Homologs of The Drosophila Polarity Gene Frizzled (fz) Are Widely Expressed in Mammalian Tissues", The Journal of Biological Chemistry, vol. 267, No. 35, pp. 25202–25207, Dec. 15, 1992.

S.L. Wolda, et al., "Overlapping Expressing of Xwnt–3A and Xwnt–1 in Neural Tissue of Xenopus Laevis Embryos", Development Biology, vol. 155, No. 1, pp. 46–57, Jan. 1993.

Neil T. Parkin, et al., "Activity of Wnt–1 as a Transmembrance Protein", Genes & Development, vol. 7, No. 11, pp. 2181–2193, Nov. 1993.

Brian A. Parr, et al., "Wnt Genes And Vertebrate Development", Current Opinion in Genetics & Development, vol. 4, No. 4, pp. 523–528, 1994.

Baihua Yang, et al., "Identification of a Common Hyaluronan Binding Motif in The Hyaluronan Binding Proteins RHAMM, CD44, And Link Protein", The EMBO Journal, vol. 13, No. 2, pp. 286–296, Jan. 15, 1994.

Frank V. Leeuwen, et al., "Biological Activity of Soluble Wingless Protein in Cultured Drosphila Imaginal Disc Cells", Nature, vol. 368, No. 6469, pp. 342–344, Mar. 24, 1994.

Roel Nusse, et al., "Mode of Proviral Activation of a Putative Mammary Oncogene (int–1) on Mouse Chromosome 15", Nature, vol. 307, No. 5946, pp. 131–136, Jan. 1984.

Frans Rijsewijk, et al., "The Drosphila Homolog of The Mouse Mammary Oncogene int–1 is Identical to The Segment Polarity Gene Wingless", Cell, vol. 50, No. 4, pp. 649–657, Aug. 14, 1987.

Charles R. Vinson, et al., "Directional Non–Cell Autonomy And The Transmission of Polarity Information by The Frizzled Gene of Drosophila", vol. 329, No. 6139, pp. 549–551, Oct. 8, 1987.

Ann S. Tsukamoto, et al, "Expression of the int–1 Gene in Transgenic Mice is Associated With Mammary Gland Hyperplasia And Adenocarcinomas in Male And Femal Mice", vol. 55, No. 4, pp. 619–625, Nov. 18, 1988.

Andrew P. McMaho, et al., "int–1 a Proto–Oncogene Involved in Cell Signaling", Development 1989 Supplement, pp. 161–167, 1989.

Jeffrey S. Rubin, et al., "Purification And Characterization of a Newly Identified Growth Factor Specific For Epithelial Cells", Proc. Natl. Acad. Sci., vol. 86, No. 3, pp. 802–806, Feb. 1989.

Charles R. Vinson, et al., "A Drosophila Tissue Polarity Locus Encodes a Protein Containing Seven Potential Transmembrance Domains", Nature, vol. 338, No. 6212, pp. 263–264, Mar. 16, 1989.

Paul W. Finch, et al., "Human KGF is FGF–Related With Properties of a Paracrine Effector of Epithelial Cell Growth", Science, vol. 245, pp. 752–755, Aug. 18, 1989.

Roger S. Bradley, et al., "The Proto–Oncogene int–1 Encodes a Secreted Protein Associated With The Extracellular Matrix", The EMBO Journal, vol. 9, No. 5, pp. 1569–1575, May 1990.

Jeffrey S. Rubin, et al., "A Broad–Spectrum Human Lung Fibroblast–Derived Mitogen is a Variant of Hepatocyte Growth Factor", Proc. Natl. Acad. Sci., vol. 88, No. 2, pp. 415–419, Jan. 15, 1991.

T. Fujiwara et al., Otsuka cDNA Project, EMBL Database, Sep. 29, 1996, XP–0020776.

L. Hillier et al., The WashU–Merck EST Project, EMBL Database, Apr. 5, 1996, XP–00207764.

Z. Zhou and J. Wang, Upregulation of human secreted Frizzled homologue in apoptosis and its down regulation in breast tumors, EMBL Database, Apr. 9, 1998, XP–002077645.

Rattner et al.DatabaseGenEmbl, Accession No. MMU88566, Mus musculus secreted frizzeled related protein sFRP–1 (Sfrp1) mRNA, Apr. 22, 1997.*

Hillier et al., Database EST, Accession No. AA424647, zv91h11.r1 Soares_NhHMPu_S1 *Homo sapiens* cDNA clone IMAGE:767205 5'mRNA sequence. WashU–Merck EST Project, May 15, 1997.*

* cited by examiner

FIG. 1A

FIG. 1B

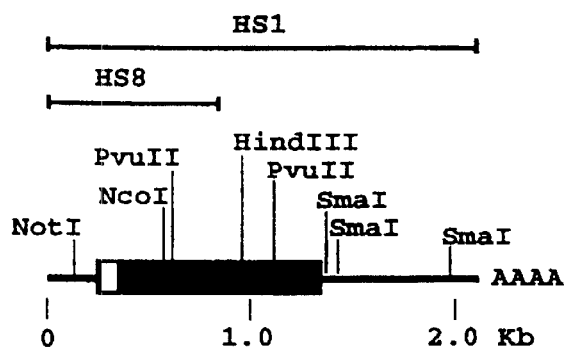

FIG. 1C

```
         10          20          30          40
MGIGRSEGGRRGALGVLLALGAALLAVGSASEYDYVSFQS 50          60          70          80
DIGPYQSGRFYTKPPQCVDIPADLRLCHNVGYKKMVLPNL 90         100         110         120
LEHETMAEVKQQASSWVPLLNKNCHAGTQVFLCSLFAPVC 130         140         150         160
LDRPIYPCRWLCEAVRDSCEPVMQFFGFYWPEMLKCDKFP 170         180         190         200
EGDVCIAMTPPNATEASKPQGTTVCPPCDNELKSEAIIEH 210         220         230         240
LCASEFALRMKIKEVKKENGDKKIVPKKKKPLKLGPIKKK 250         260         270         280
DLKKLVLYLKNGADCPCHQLDNLSHHFLIMGRKVKSQYLL 290         300         310
TAIHKWDKKNKEFKNFMKKMKNHECPTFQSVFK    (SEQ ID NO: 4)
```

| | | | | | | |
|---|---|---|---|---|---|---|
| hFRP | 57 | CVDIPADLRL | CHNVGYKKMV | LPNLLEHETM | AEVKQQASSW | VPLLNKNCHA |
| hFZ | 39 | CQPIS..IPL | CTDIAYNQTI | MPNLLGHTNQ | EDAGLEVHQF | YPLVKVQCSP |
| hFZ5 | 33 | CQEIT..VPM | CRGIGYNLTH | MPNQFNHDTQ | DEAGLEVHQF | WPLVEIQCSP |
| mFZ3 | 28 | CEPIT..LRM | CQDLPYNTTF | MPNLLNHYDQ | QTAALAMEPF | HPMVNLDCSR |
| mFZ4 | 45 | CDPIR..IAM | CNLGYNVTK | MPNLVGHELQ | TDAELQLTTF | TPLIQYGCSS |
| mFZ6 | 24 | CEPIT..VPR | CMKMTYNMTF | FPNLMGHYDQ. | GIAAVEMGHF | LHLANLECSS |
| mFZ7 | 49 | CQPIS..IPL | CTDIAYNQTI | LPNLLGHTNQ | EDAGLEVHQF | YPLVKVQCSP |
| mFZ8 | 35 | CQEIT..VPL | CKGIGYNYTY | MPNQFNHDTQ | DEAGLEVHQF | WPLVEIQCSP |
| rFZ1 | 111 | CQPIS..IPL | CTDIAYNQTI | MPNLLGHTNQ | EDAGLEVHQF | YPLVKVQCSA |
| rFZ2 | 44 | CQPIS..IPL | CTDIAYNQTI | MPNLLGHTNQ | EDAGLEVHQF | YPLVKVQCSP |
| dFZ | 53 | CEPIT..ISI | CKNIPYNMTI | MPNLIGHTKQ | EEAGLEVHQF | APLVKIGCSD |
| dFZ2 | 64 | CEEIT..IPM | CRGIGYNMTS | FPNEMNHETQ | DEAGLEVHQF | WPLVEIKCSP |
| cFZ | 26 | CQKVD..HEM | CNDLPYNLTS | FPNLVDEESW | KDASESILTY | KPLLSVVCSE |
| mCOL | 370 | CLPLPPTLTL | CSRLGIGHFW | LPNHLHHTDS | VEVEATVQAW | GRFLHTNCHP |
| hFRZB | 35 | CEPVR..IPL | CKSLPWNMTK | MPNHLHHSTQ | ANAILAIEQF | EGLLGTHCSP |
| mSDF5 | 40 | CKPIPANLQL | CHGIEYQNMR | LPNLLGHETM | KEVLEQAGAW | IPLVMKQCHP |
| | | * | * | ** | | * |
| | | * | * | | | * |
| CONSENSUS | | C-PI-...IPL | C--I-YN-T- | MPNLLGH--Q | --AGLEVHQF | -PLV---CSP |

| | | | | | |
|---|---|---|---|---|---|
| hFRP | GTQVFLCSLF | APVC...LD. | RPIYPCRWLC | EAVRDSCEPV | MQFFGFYWPE |
| hFZ | ELRFFLCSMY | APVC.TVLE. | QAIPPCRSIC | ERARQGCEAL | MNKFGFQWPE |
| hFZ5 | DLRFFLCTMY | TPICLPDYH. | KPLPPCRSVC | ERAKAGCSPL | MRQYGFAWPE |
| mFZ3 | DFRPFLCALY | APICME..YG | RVTLPCRRLC | QRAYSECSKL | MEMFGVPWPE |
| mFZ4 | QLQFFLCSVY | VPMCTEKINI | .PIGPCGGMC | LSVKRRCEPV | LREFGFAWPD |
| mFZ6 | NIEMFLCQAF | IPTCTE..QI | HVVLPCRKLC | EKIVSDCKKL | MDTFGIRWPE |
| mFZ7 | ELRFFLCSMY | APVC.TVLD. | QAIPPCRSLC | ERARQGCEAL | MNKFGFQWPE |
| mFZ8 | DLKFFLCSMY | TPICLEDYK. | KPLPPCRSVC | ERAKAGCAPL | MRQYGFAWPD |
| rFZ1 | ELKFFLCSMY | APVC.TVLE. | QALPPCRSLC | ERA.QGCEAL | MNKFGFQWPD |
| rFZ2 | ELRFFLCSMY | APVC.TVLE. | QAIPPCRSIC | ERARQGCEAL | MNKFGFQWPE |
| dFZ | DLQLFLCSLY | VPVC.TILE. | RPIPPCRSLC | ESAR.VCEKL | MKTYNFNWPE |
| dFZ2 | DLKFFLCSMY | TPICLEDYH. | KPLPVCRSVC | ERARSGCAPI | MQQYSFEWPE |
| cFZ | QLKFFLCSVY | FPMCNEKLAN | .PIGPCRPLC | LSVQEKCLPV | LESFGFKWPD |
| mCOL | FLAWFFCLLL | APSCGPG.PP | PPLPPCRQFC | EALEDEC... | ...WNYLAGD |
| hFRZB | DLLFFLCAMY | APICTIDFQH | EPINPCKSVC | ERARQGCEPI | LIKYRHSWPE |
| mSDF5 | DTKKFLCSLF | APVCLDDLD. | ETICPCHSLC | MQVKDRCAPV | MSAFGFPWPD |
| | * * | * * | * | * | * |
| | * | * | | * | |
| CONSENSUS | -L-FFLCSMY | AP-C---L-. | -PIPPCRSLC | ERA--GCEPL | M--FGF-WPE |

| | | | | |
|---|---|---|---|---|
| hFRP | MLK..CDKFP | .EG....DVC | 166 | (SEQ ID NO: 19) |
| hFZ | RLR..CEHFP | RHG..AEQIC | 150 | (SEQ ID NO: 9) |
| hFZ5 | RMS..CDRLP | VLGRDAEVLC | 147 | (SEQ ID NO: 10) |
| mFZ3 | DME..CSRFP | D........C | 133 | (SEQ ID NO: 11) |
| mFZ4 | TLN..CSKFP | PQN.DHNHMC | 158 | (SEQ ID NO: 12) |
| mFZ6 | ELE..CNRLP | H........C | 129 | (SEQ ID NO: 13) |
| mFZ7 | RLR..CENFP | VHG..AGEIC | 160 | (SEQ ID NO: 14) |
| mFZ8 | RMR..CDRLP | EQG.NPDTLC | 148 | (SEQ ID NO: 15) |
| rFZ1 | TLK..CEKFP | VHG..AGELC | 221 | (SEQ ID NO: 16) |
| rFZ2 | RLR..CEHFP | RHG..AEQIC | 155 | (SEQ ID NO: 17) |
| dFZ | NLE..CSKFP | VHG..GEDLC | 163 | (SEQ ID NO: 18) |
| dFZ2 | RMA..CEHLP | LHG.DPDNLC | 177 | (SEQ ID NO: 20) |
| cFZ | VIR..CDKFP | LEN.NREKMC | 139 | (SEQ ID NO: 21) |
| mCOL | RLPVVCASLP | SQE...DGYC | 479 | (SEQ ID NO: 22) |
| hFRZB | NLA..CEELP | VYDR...GVC | 147 | (SEQ ID NO: 23) |
| mSDF5 | MLE..CDRFP | QDN....DLC | 152 | (SEQ ID NO: 24) |
| | * * | * | | |
| CONSENSUS | -L-..C--FP | --G..----C | | (SEQ ID NO: 25) |

Fig. 2

```
        10         20         30         40         50         60         70
cctgcagcct ccggagtcag tgccgcgcgc ccgccgcccc gcgccttcct gctcgccgca cctccgggag 80         90        100        110        120        130        140
ccggggcgca cccagcccgc agcgccgcct ccccgcccgc gccgcctccg accgcaggcc gagggccgcc 150        160        170        180        190        200        210
actggccggg gggaccgggc agcagcttgc ggccgcggag ccgggcaacg ctggggactg cgccttttgt 220        230        240        250        260        270        280
ccccggaggt ccctggaagt ttgcggcagg acgcgcgcgg ggaggcggcg gaggcagccc cgacgtcgcg 290        300        310        320        330        340        350
gagaacaggg cgcagagccg gcatgggcat cgggcgcagc gagggggggcc gccgcgggg*c cctgggcgtg 360        370        380        390        400        410        420
ctgctggcgc tgggcgcggc gcttctggcc gtgggctcgg ccagcgagta cgactacgtg agcttccagt 430        440        450        460        470        480        490
cggacatcgg cccgtaccag agcgggcgct tctacaccaa gccacctcag tgcgtggaca tccccgcgga 500        510        520        530        540        550        560
cctgcggctg tgccacaacg tgggctacaa gaagatggtg ctgcccaacc tgctggagca cgagaccatg 570        580        590        600        610        620        630
gcggaggtga agcagcaggc cagcagctgg gtgcccctgc tcaacaagaa ctgccacgcc gggacccagg 640        650        660        670        680        690        700
tcttcctctg ctcgctcttc gcgcccgtct gcctggaccg gcccatctac ccgtgtcgct ggctctgcga 710        720        730        740        750        760        770
ggccgtgcgc gactcgtgcg agccggtcat gcagttcttc ggcttctact ggcccgagat gcttaagtgt 780        790        800        810        820        830        840
gacaagttcc cggagggggga cgtctgcatc gccatgacgc cgcccaatgc caccgaagcc tccaagcccc 850        860        870        880        890        900        910
aaggcacaac ggtgtgtcct ccctgtgaca acgagttgaa atctgaggcc atcattgaac atctctgtgc 920        930        940        950        960        970        980
cagcgagttt gcactgagga tgaaaataaa agaagtgaaa aagaaaatg gcgacaagaa gattgtcccc 990       1000       1010       1020       1030       1040       1050
aagaagaaga agccectgaa gttggggccc atcaagaaga aggacctgaa gaagcttgtg ctgtacctga 1060       1070       1080       1090       1100       1110       1120
agaatggggc tgactgtccc tgccaccagc tggacaacct cagccaccac ttcctcatca tgggccgcaa
```

Fig. 8A (SEQ ID NO: 2, bases 1-1120)

```
        1130       1140       1150       1160       1170       1180       1190
ggtgaagagc cagtacttgc tgacggccat ccacaagtgg gacaagaaaa acaaggagtt caaaaacttc 1200       1210       1220       1230       1240       1250       1260
atgaagaaaa tgaaaaacca tgagtgcccc acctttcagt ccgtgtttaa gtgattctcc cggggggcagg 1270       1280       1290       1300       1310       1320       1330
gtggggaggg agcctcgggt ggggtgggag cgggggggac agtgcccggg aacccgtggt cacacacacg 1340       1350       1360       1370       1380       1390       1400
cactgccctg tcagtagtgg acattgtaat ccagtcggct tgttcttgca gcattcccgc tccctttccc 1410       1420       1430       1440       1450       1460       1470
tccatagcca cgctccaaac cccagggtag ccatggccgg gtaaagcaag ggccatttag attaggaagg 1480       1490       1500       1510       1520       1530       1540
tttttaagat ccgcaatgtg gagcagcagc cactgcacag gaggaggtga caaaccattt ccaacagcaa 1550       1560       1570       1580       1590       1600       1610
cacagccact aaaacacaaa aaggggggatt gggcggaaag tgagagccag cagcaaaaac tacattttgc 1620       1630       1640       1650       1660       1670       1680
aacttgttgg tgtggatcta ttggctgatc tatgcctttc aactagaaaa ttctaatgat tggcaagtca 1690       1700       1710       1720       1730       1740       1750
cgttgtttc aggtccagag tagtttcttt ctgtctgctt taaatggaaa cagactcata ccacacttac 1760       1770       1780       1790       1800       1810       1820
aattaaggtc aagcccagaa agtgataagt gcagggagga aaagtgcaag tccattatct aatagtgaca 1830       1840       1850       1860       1870       1880       1890
gcaaagggac caggggagag gcattgcctt ctctgcccac agtctttccg tgtgattgtc tttgaatctg 1900       1910       1920       1930       1940       1950       1960
aatcagccag tctcagatgc cccaaagttt cggttcctat gagcccgggg catgatctga tccccaagac 1970       1980       1990       2000       2010       2020       2030
atgtggaggg gcagcctgtg cctgcctttg tgtcagaaaa aggaaaccac agtgagcctg agagagacgg 2040       2050       2060       2070
cgattttcgg gctgagaagg cagtagtttt caaaacacat agtta
```

* We have observed an insert of sequence 'cag' at this site in some cDNA constructs. This would result in an insert of a single amino acid residue, alanine, in the putative signal peptide sequence without altering any of the remaining amino acid sequence. This may result from alternative splicing, but we have not excluded the possibility of a sequencing artifact. We hope to resolve this matter soon. The numbering scheme in the above figure corresponds to the sequence lacking 'cag.'

Fig. 8B (SEQ ID NO: 2, bases 1121-2075)

Fig. 8C (SEQ ID NO: 27)

```
            10         20         30         40         50         60         70         80         90        100
GAATTCTCAGGAATTCGAGGTAGAAGGTGGCAGAGAGAGACTTCTGTTCCTGGGGCCGAGCTGTTGTGCTGATACCGTCCTCCTTGCGGTCTGCCCTAGTGG 0100
GGACCCTTGATTTTAACTTGAAGTTCCTGGACTGGGTCTAACCTTAGCATGTGCTGAGTGATGACTTGGTATTTACACCAGCCACGCTGATAAGTG 0200
CACATGTGTTTTTTAATGTTTGGCTTTCCACACACAAACACACAGATGTGCTGTCGCCCGGGCTAGGACTGGAGTAGGGTTTTTCTATTTAAATATATA 0300
TTATATATTTAAAAAAGTGTCCTCCCAGAGCTAATACCGTTGCTAGCAGCTCTTCCTGCCGCCACACCGGCAAAGTCCACCACTGCCCCAGTGTTGAG 0400
GGCCACCATGGGCGGCCCACCTGGAGAGTGCTGCTCACAGCAAACAGCTCCAACTGGCCTTCGCCTTCCAGGGAGCCCAGCCAGGCCCACTG 0500
GGTATTTACAAGCAGACCTCCCTGCTTCAGCCTTGAACCCCTGTTAGTTGGGAAACCACCTGTCTGCACCGCAGCTAGAGAACCGAGGAGAGGAGC 0600
CGCTAGTCTAAAGGGCTGTTGTTGAAATTAGGAAGCAGTAGTGTAAAGAAAAAAAAGAAAAAAAATTTGGGAGGCCAAGGCAGGAGCATCACCTGAGGTCAGC 0700
AGTTCGAGACCAGCCTGCTAACGTGGTGAAAACCCCGTCTGTGAAACCCGTCTCTACTAAAAATACAAAAAATTAGCGGGGCGTGTGGCACGCGGCTGTAATCCCAGCTAC 0800
TCGGGAGGCTGAGGCAGGAGAATGGCTTGAACCCGGGAGGCGGAGATAGCCAGTCACGAGAGATAGCCAGTCACGAGATTGCACTCCAGCCTGGGCAACAAGAGAGCGA 0900
AACTTCGTCAAAAAAAAAAAGTCTTCATAATTTCATGGGTTTGCAAGTATTTGCAAGTAATGGCAATGCGAGTTAATTACAGCGT 1000
CCGCCCTGGTCTCTCTCCACCCCAGCCGTGATCCATTCCCCCTTGTCTTTCCCCTTGTCTTTTTCCTACTCCCCCCTTTATTTATGTATTTTGGTTTT 1100
GTTTTTAAGGGTGTTGAGCCGCGTCTGTTCTAGTAAACCGAACCCGCGATTGGCTCCCGCGCCGGTGACGACGTGGTAACGAG 1200
TGCGGCTCGCCCCGCCGGAGCTGATTGGCTGCGCGGACTCGGCCTGCCGGGCTCGGCCTGCGGAGCCGTAGGAGCGCGACTCCAGCCCTGCAGCCTCCGAGTCA 1300
GTGCCGCGCGCCCCCCCGCCGCCCCCGCGCCTTCCTGCTCGCGGGGACCCTGCGGCCCGGCCCAGCCCAGCGCCCGCGAGCCGGCAACGCTGGGGACTGCGCCTTTTGTCCCCGGAGG 1500
GACCGCAGGCCGCGAGGGCCGCACTGGCCAGGACGCGCGGGACGCGGGAGGCAGCCCCGACGTCGCGAGGAGAACAGGGCGCAGAGCCGGCATGGCGCATCGGGCGCAC 1600
TCCCTGGAAGTTTGCGGCAGACGCCGCGGGGCAGCCCTGGCGTGCTGCTGGGGCGCTTCTGGGCTCGGCGCTGGGCGGCGCAGCGAGTACGACTGAGCTTCCAG 1700
GGAGGGGGCGCCGCGGGGCAGCCGTACCAGAGCGGGGCGCGCTTCTACACCAAGCCACCTCAGTGCGTGACATCCCGCGACCTGGGTGCCCCTGCTCAACAAGAACTGCCACGC 1800
TCGGACATCGGCCCGTACCAGAGCGGGGCGCGCTTCTACACCAAGCCACCTCAGTGCGTGACATCCCGCGACCTGGGTGCCCCTGCTCAACAAGAACTGCCACGC 1900
AGAAGATGGTGCTGCCAACCTGCTGAGACGAGACCATGGCGGAGGTGAAGCAGCAGCAGGCCCATCTCCGTGTCGCCGGCCTGCCTGGACCGGCCATCCGTGCCTTACCCGTGCTCGCCGT 2000
CGGGACCCCAGTTCTTCCTGCTCTCGCCGCCTCTTCGCGCCCCCGTGTCGCCGGCCCATCCGTGCCTTACCCGTGCTCGCCGTCTGCGAGGCCCGTGCTGCCGACTCGTGC 2000
GAGCCGGTCATGCAGTTCTTCGGCTTCACTGGCCCGAGATGCTTAAGTGTGACAAGTTCCCGGAGGGGACGTCTGCATCGCCATGACCGCCCAATG 2100
CCACCGAAGCCTCCAAGCCCCAAG

Fig. 11 (SEQ ID NO: 26)
```

POLYNUCLEOTIDES ENCODING HUMAN FRP AND FRAGMENTS THEREOF

CROSS-REFERENCE TO RELATED APPLICATIONS

This application claims the benefit of U.S. Provisional Application No. 60/050,417, entitled "HUMAN FRP AND FRAGMENTS THEREOF INCLUDING METHODS FOR USING THEM," filed on May 29, 1997, by Rubin et al., and U.S. Provisional Application No. 60/050,495 entitled "HUMAN FRP AND FRAGMENTS THEREOF INCLUDING METHODS FOR USING THEM," filed on Jun. 23, 1997, by Rubin et al., which are incorporated by reference herein.

BACKGROUND OF THE INVENTION

1. Field of the Invention

This invention is in the field of molecular biology and in particular relates to the identification of a novel human Frizzled Related Protein (FRP) involved in cell growth and differentiation.

2. Description of Related Art

Extracellular signaling molecules have essential roles as inducers of cellular proliferation, migration, differentiation, and tissue morphogenesis during normal development. These molecules also participate in many of the aberrant growth regulatory pathways associated with neoplasia. In addition, these molecules function as regulators of apoptosis, the programmed cell death that plays a significant role in normal development and functioning of multicellular organisms, and when disregulated, is involved in the pathogenesis of numerous diseases. See e.g. Thompson, C. B., Science 267, 1456–1462 (1995).

Apoptosis is a result of an active cell response to physiological or damaging agents and numerous gene products are involved in signal transduction, triggering and executive steps of the apoptotic pathways. Other proteins do not take part in the apoptotic cascade by themselves but modify cell sensitivity to proapoptotic stimuli. While many genes and gene families that participate in different stages of apoptosis have recently been identified and cloned, because the apoptotic pathways have not been clearly delineated, many novel genes which are involved in these processes await discovery.

The identification and characterization of molecules involved in growth and differentiation is an important step in both the identification of mechanisms of cellular development and oncogenesis and the subsequent conception of novel therapies based on this knowledge. One group of molecules known to play a significant role in regulating cellular development is the Wnt family of glycoproteins. In vertebrates, this family consists of more than a dozen structurally related molecules, containing 350–380 amino acid residues of which >100 are conserved, including 23–24 cysteine residues. See e.g. Parr, B. A. & McMahon, A. P. (1994) Curr Opin Genet Dev 4, 523–8.

Wnt-1, the first Wnt-encoding gene to be isolated, was identified as an oncogene expressed as a result of insertional activation by the mouse mammary tumor virus (Nusse, R., et al., Nature 307, 131–6 1984). Subsequently, transgenic expression of Wnt-1 confirmed that constitutive expression of this gene caused mammary hyperplasia and adenocarcinoma (Tsukamoto et. al., Cell 55, 619–25 (1988)). Targeted disruption of the Wnt-1 gene revealed an essential role in development, as mouse embryos had severe defects in their midbrain and cerebellum. Thomas et. al., Cell 67, 969–76 (1991). In addition, Wingless (Wg), the Drosophila homolog of Wnt-1, was independently identified as a segment polarity gene (Rijsewijk et al., Cell 50, 649–57 (1987)). Gene targeting of other Wnt genes demonstrated additional important roles for these molecules in kidney tubulogenesis and limb bud development. See e.g. Parr et al., Nature 374, 350–3 (1995); Stark K et al. Nature 372: 679–683, 1994.

Several aspects of Wnt signaling have been illuminated by studies in flies, worms, frogs and mice (Perrimon, N. (1996) Cell 86, 513–6; Miller, J. R. & Moon, R. T. (1996) Genes Dev 10, 2527–39), but until recently little was known about key events which occur at the external cell surface. Identification of Wnt receptors was hampered by the relative insolubility of the Wnt proteins, which tend to remain tightly bound to cells or extracellular matrix. However, several observations now indicate that members of the Frizzled (FZ) family of molecules including Frzb can function as receptors for Wnt proteins or as components of a Wnt receptor complex. See e.g. He et. al., Science 275, 1652–1654 (1997).

The prototype for this family of receptor molecules, Drosophila frizzled (Dfz), was first identified as a tissue polarity gene that governs orientation of epidermal bristles. Vinson et al., Nature 329, 549–51 (1987). Cells programmed to express a second Drosophila Fz gene, Fz2, bind Wg and transduce a Wg signal to downstream components of the signaling pathway. Bhanot et al., Nature 382, 225–30 (1996). Each member of the Fz receptor gene family encodes an integral membrane protein with a large extracellular portion, seven putative transmembrane domains, and a cytoplasmic tail. See e.g. Wang et al., J Biol Chem 271, 4468–76 (1997). Near the NH2-terminus of the extracellular portion is a cysteine-rich domain (CRD) that is well conserved among other members of the FZ family. The CRD, comprised of ~110 amino acid residues, including 10 invariant cysteines, is the putative binding site for Wnt ligands. Bhanot et al., Nature 382, 225–30 (1996).

In organisms including frogs, fruit flies, and mice, proteins including Wingless, Armadillo, and Frizzled form part of a signaling cascade that controls crucial events during early embryonic development—particularly gastrulation, the process by which a hollow ball of embryonic cells collapses in on itself, forming the major embryonic tissues. In vertebrates, the signaling pathway—headed by the Wnt family of growth factors contribute to the formation of body axis and the proper development of the central nervous system, kidneys, and limbs. When it is activated inappropriately in adult cells, the pathway can precipitate the formation of tumors. During gastrulation, Fz family members may interact with Wnt to control the proper development of the nervous system and muscles. The coupling of Wnt and Frizzled activates a pathway that leads to the expression of a set of Wnt-responsive genes, including those that encode the transcription factors such as Engrailed and Siamois.

When Wnt mRNA is injected into Xenopus embryos in the 4–8 cell stage, the tadpoles develop a second body axis: They can duplicate all or part of the nervous systems from head to tail, and many of their organs are duplicated. Interestingly, during gastrulation, a Wnt family member known as Xwnt-8 serves to "ventralize" the embryo—steering cells in the mesoderm toward forming muscle. Injecting Frzb mRNA into a developing Xenopus embryo prior to gastrulation inhibits muscle formation, generating tadpoles that are stunted in appearance, with shortened trunks due to the lack of muscle tissue. The embryos also have enlarged heads, because an abnormal number of mesodermal cells adopt a dorsal fate. Knockout mice have already helped researchers understand a few of the various roles that Wnts play in development. To date, scientists have identified 16 different Wnts that function in vertebrate development. Many Wnts appear to be involved in directing the development of the central nervous system (CNS). Others control the formation of nephrons in the kidney and the proper development of the limbs.

The existence of molecules that have a FZ CRD but lack the seven transmembrane motif and cytoplasmic tail suggests that there is a subfamily of proteins that function as regulators of Wnt activity. Little is known about the activity of SDF5, which was cloned using the signal sequence trap method. FRZB is a heparin-binding molecule thought to be involved in skeletal morphogenesis. Recently Rattner et al. cloned cDNAs encoding the murine homologs of Fz family members, and showed that, when artificially linked to the plasma membrane via a glycolipid anchor, SDF5 and FRZB conferred cellular binding to Wg. Rattner et al., P.N.A.S. 94, 2859–2863 (1997).

The disregulation of Wnt pathways appears to be a factor in aberrant growth and development. Mutations in β-catenin, a protein that accumulates when the Wnt pathway is activated, are associated with tumor development in human colon cancers and melanomas. β-catenins couple with other cellular transcription factors and help to activate Wnt-responsive genes. These results confirm that the Wnt-signaling pathway can play an important role in the embryo and the adult. Ultimately, Wnt transmits its signal by allowing β-catenin to accumulate in the cell cytoplasm. There, β-catenin binds to members of the Tcf-Lef transcription factor family and translocates to the nucleus. When Wnt is absent, β-catenin instead forms a complex with glycogen synthase kinase-3 (GSK-3) and the adenomatous polyposis coli (APC) tumorsuppressor protein. This interaction is associated with the phosphorylation of β-catenin, marking it for ubiquitination and degradation. Wnt permits the accumulation of β-catenin by inhibiting the function of GSK-3. The mutations that drive tumor formation follow a similar strategy. Mutations in APC render the tumor-suppressor protein unable to bind to β-catenin, which remains unphosphorylated and accumulates in the cell, turning on Wnt-responsive genes.

Given the potential complexity of interactions between the multiple members of Wnt and FZ families, additional mechanisms might exist to modulate Wnt signaling during specific periods of development or in certain tissues. What is needed in the art is the identification and characterization of novel effectors of the processes which are related to cellular growth and development. The identification of such mechanisms and in particular, the effectors of these mechanisms is important for understanding and modulating the processes of cellular regulation.

SUMMARY OF THE INVENTION

The invention includes nucleotide sequences that encode a novel polypeptide, designated in the present application as "FRP" (Frizzled Related Protein), which is a secreted antagonist of the Wnt signaling pathway and exhibits a number of characteristics which make it a useful tool for studying cell growth and differentiation as well as oncogenesis. As such, this novel protein has a variety of applications in the identification, characterization and regulation of activities associated with cellular function as well as processes associated with oncogenesis.

The invention provides "FRP" (Frizzled Related Protein) polypeptides [SEQ ID Nos. 3,4] and fragments thereof and polynucleotide sequences encoding FRP polypeptides [SEQ ID Nos. 1, 2, and 27]. The invention further provides antibodies which are specific for FRP polypeptides and animals having FRP transgenes. Moreover, the invention provides methods of producing FRP polypeptides and polynucleotide sequences. In addition, the invention provides methods of assaying for FRP in a sample as well as methods for detecting FRP binding partners.

In one embodiment, the invention provides isolated nucleic acid molecules which encode FRP polypeptides. For example, the isolated nucleic acid can include DNA encoding FRP polypeptide having amino acid residues 1 to 313 of FIG. 1 [SEQ ID No. 2, bases 303–1241], or is complementary to such encoding nucleic acid sequence, and remains stably bound to it under at least moderate, and optionally, under high stringency conditions. In another embodiment, the invention provides a vector comprising a gene encoding a FRP polypeptide. A host cell comprising such a vector is also provided. By way of example, the host cells may be *E. coli*, yeast or mammalian cells. A process for producing FRP polypeptides is further provided and comprises culturing host cells under conditions suitable for expression of FRP. If desired, the FRP may be recovered.

In another embodiment, the invention provides isolated FRP polypeptide. In one embodiment, FRP of the invention comprises 313 amino acids and includes a signal sequence, Wnt binding domain, a hyaluronic acid binding domain and potential asparagine-linked glycosylation sites. In particular, the invention provides isolated native sequence FRP polypeptide, which in one embodiment, includes an amino acid sequence comprising residues 1 to 313 of FIG. 1 [SEQ ID No. 4]. In a related embodiment, the invention provides chimeric molecules comprising FRP polypeptide fused to a heterologous polypeptide or amino acid sequence. An example of such a chimeric molecule is a factor which includes a FRP fused to a polyhistidine polypeptide sequence. In another embodiment, the invention provides a non-human transgenic animal whose somatic and germ cells contain a transgene comprising human FRP. In yet another embodiment, the invention provides a polypeptide capable of specifically binding a FRP polypeptide such as an antibody specific for a FRP polypeptide. Optionally, the antibody is a monoclonal antibody.

Also included in the invention is a method for regulating cell signaling pathways by inhibiting the interaction of Wnt with Fz receptors by blocking this interaction with FRP molecules. The invention also provides methods for determining the presence of FRP molecules in a sample. The invention also provides a method for determining the presence of Wnt molecules in a sample by screening the sample with FRP. In addition, the invention provides a method for monitoring the course of a neoplastic condition by quantitatively determining the presence of Wnt molecules in a sample by screening the sample with FRP.

In other embodiments, the invention provides methods for using FRP polypeptides and nucleic acids for studying and modulating mechanisms involved in cellular proliferation. In one embodiment, the invention provides a method of modulating cellular phenotype by controlling the level of FRP expression within the cell. In a more specific embodiment, the invention provides a method of inhibiting cellular proliferation and/or differentiation by exposing a cell to FRP.

BRIEF DESCRIPTION OF THE DRAWINGS

FIG. 1A shows an SDS/PAGE analysis of heparin-Sepharose purified FRP.

FIG. 1B shows a restriction endonuclease map with representations of the human FRP cDNA clones and the coding region of the gene.

FIG. 1C [SEQ ID No. 4] shows the predicted FRP amino acid sequence (standard single-letter code).

FIG. 2 [SEQ ID No. 11–27] shows a comparison of the CRDs of FRP and other members of the FZ family.

FIG. 11 [SEQ ID No. 26] shows the nucleic acid sequence of FRP 5' flanking genomic sequences.

DETAILED DESCRIPTION OF THE INVENTION

Definitions

Figure 3:
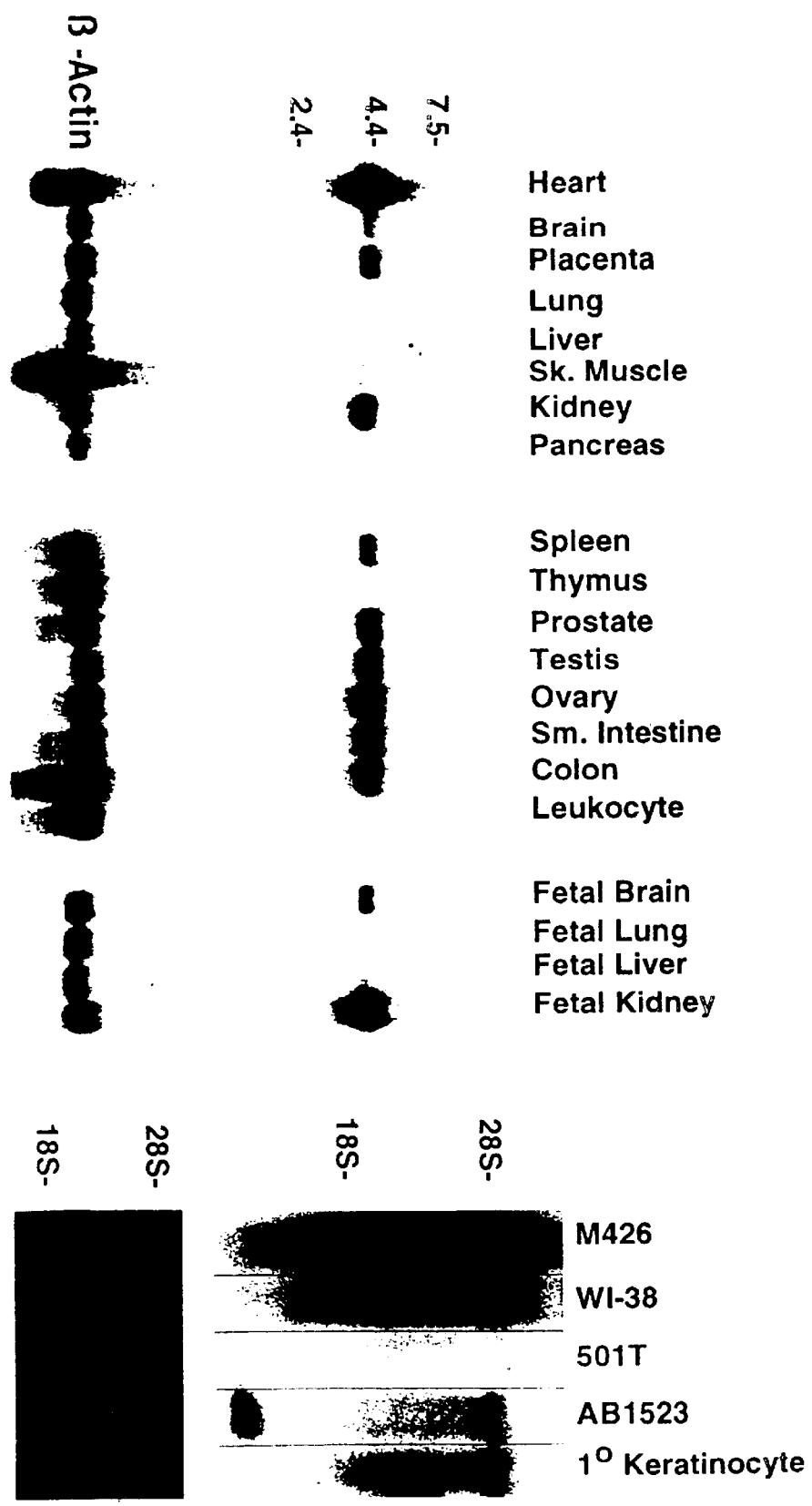
FIG. 3 shows a northern blot analysis showing FRP mRNA expression in normal human adult and embryonic tissues, and in cultured cells.

As used in this application, the following words or phrases have the meanings specified.

The terms "FRP polypeptide" and "FRP" when used herein encompass native sequence FRP and FRP variants (which are further defined herein). The FRP may be isolated from a variety of sources, such as from human tissue types or from another source, or prepared by recombinant or synthetic methods.

The FRP polypeptide, which may be a fragment of a native sequence, contains a Wnt binding domain. Typically, the FRP polypeptide also includes a hyaluronic acid binding domain.

A "native sequence FRP" is a polypeptide having the same amino acid sequence as an FRP derived from nature. Such native sequence FRP can be isolated from nature or can be produced by recombinant or synthetic means. The term "native sequence FRP" specifically encompasses naturally-occurring variant forms (e.g., alternatively spliced forms) and naturally-occurring allelic variants of the FRP. In one embodiment of the invention, the native sequence FRP is a mature or full-length native sequence FRP polypeptide comprising amino acids 1 to 313 of FIG. 1 [SEQ ID No. 4].

"FRP variant" means a functionally active FRP as defined below having at least about 80% amino acid sequence identity with FRP, such as the FRP polypeptide having the deduced amino acid sequence shown in FIG. 1 [SEQ ID No. 4] for a full-length native sequence FRP. Such FRP variants include, for instance, FRP polypeptides wherein one or more amino acid residues are added, or deleted, at the N- or C-terminus of the sequence of FIG. 1. Ordinarily, a FRP variant will have at least about 80% or 85% amino acid sequence identity with native FRP sequences, more preferably at least about 90% amino acid sequence identity. Most preferably a FRP variant will have at least about 95% amino acid sequence identity with native FRP sequence of FIG. 1 [SEQ ID No. 4].

"Percent (%) amino acid sequence identity" with respect to the FRP sequences identified herein is defined as the percentage of amino acid residues in a candidate sequence that are identical with the amino acid residues in the FRP sequence, after aligning the sequences in the same reading frame and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST software. Those skilled in the art can determine appropriate parameters for measuring alignment, including any algorithms needed to achieve maximal alignment over the full length of the sequences being compared.

"Percent (%) nucleic acid sequence identity" with respect to the FRP sequences identified herein is defined as the percentage of nucleotides in a candidate sequence that are identical with the nucleotides in the FRP sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

The term "epitope tagged" when used herein refers to a chimeric polypeptide comprising FRP, or a functional fragment thereof, fused to a "tag polypeptide". The tag polypeptide has enough residues to provide an epitope, against which an antibody can be made, or which can be identified by some other agent, yet is short enough such that it does not interfere with activity of the FRP. The tag polypeptide preferably also is sufficiently unique so that the antibody does not substantially cross-react with other epitopes. Suitable tag polypeptides generally have at least six amino acid residues and usually between about 8 to about 50 amino acid residues (preferably, between about 10 to about 20 residues).

"Isolated," when used to describe the various polypeptides disclosed herein, means polypeptide that has been identified and separated and/or recovered from a contaminating component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified to a degree sufficient to obtain N-terminal or internal amino acid sequence by use of a spinning cup sequenator, or to homogeneity by SDS-PAGE under non-reducing or reducing conditions using Coomassie blue or silver stain. Isolated polypeptide includes polypeptide in situ within recombinant cells, since at least one component of the FRP natural environment will not be present. Ordinarily, however, isolated polypeptide will be prepared by at least one purification step (referred to herein as an "isolated and purified polypeptide").

An "isolated" FRP nucleic acid molecule is a nucleic acid molecule that is identified and separated from at least one contaminant nucleic acid molecule with which it is ordinarily associated in the natural source of the FRP nucleic acid. An isolated FRP nucleic acid molecule is other than in the form or setting in which it is found in nature. Isolated FRP nucleic acid molecules therefore are distinguished from the FRP nucleic acid molecule as it exists in natural cells. However, an isolated FRP nucleic acid molecule includes FRP nucleic acid molecules contained in cells that ordinarily express FRP where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking may be accomplished by ligation at convenient restriction sites. If such sites do not exist, the synthetic oligonucleotide adaptors or linkers may be used in accordance with conventional practice.

"Polynucleotide" and "nucleic acid" refer to single or double-stranded molecules which may be DNA, comprised of the nucleotide bases A, T, C and G, or RNA, comprised of the bases A, U (substitutes for T), C, and G. The polynucleotide may represent a coding strand or its complement. Polynucleotide molecules may be identical in sequence to the sequence which is naturally occurring or may include alternative codons which encode the same amino acid as that which is found in the naturally occurring sequence (See, Lewin "Genes V" Oxford University Press Chapter 7, pp. 171–174 (1994)). Furthermore, polynucleotide molecules may include codons which represent conservative substitutions of amino acids as described. The polynucleotide may represent genomic DNA or cDNA.

"Polypeptide" refers to a molecule comprised of amino acids which correspond to those encoded by a polynucleotide sequence which is naturally occurring. The polypeptide may include conservative substitutions where the naturally occurring amino acid is replaced by one having similar properties, where such conservative substitutions do not alter the function of the polypeptide (See, Lewin "Genes V" Oxford University Press Chapter 1, pp.: 9–13 (1994)).

The term "antibody" is used in the broadest sense and specifically covers single anti-FRP monoclonal antibodies (including agonist, antagonist, and neutralizing antibodies) and anti-FRP antibody compositions with polyepitopic specificity as well as other recombinant molecules derived from these antibodies. The term "monoclonal antibody" as used herein refers to an antibody obtained from a population of substantially homogeneous antibodies, i.e., the individual antibodies comprising the population are identical except for possible naturally-occurring mutations that may be present in minor amounts.

As used herein, "non-FRP binding molecule" is defined as a molecule which does not bind FRP.

As used herein a "binding domain" means that portion or portions of a molecule which confer the ability to bind its target.

As used herein "blocking" means to interfere with the binding of one molecule to another.

As used herein a "sample" means any sample which may contain molecule of interest and includes but is not limited to (1) biological fluids such as solutions comprising blood, lymph, saliva and/or urine and (2) tissues derived from brain, lung, muscle and/or bone.

In order that the invention herein described may be more fully understood, the following description is set forth.

Identification of a Novel Wnt Binding Ligand

Disclosed herein is a novel human gene product which resembles FZ proteins in that it possesses a conserved FZ CRD, a putative binding domain for Wnt ligands. In contrast to the original members of the FZ family, FRP lacks any transmembrane region or cytoplasmic domain required to transduce Wnt signaling inside the cell. Because it is preferentially distributed to the cell surface or matrix, it is well-positioned to interact with Wnt proteins. Findings disclosed herein indicate that in Xenopus embryos FRP inhibits Wnt-dependent axial duplication when various Wnts and FRP are co-expressed. FRP behaves like a dominant-negative receptor in this model system, similar to the effect of the secreted NH2-terminal ectodomain of human FZ5 on axis duplication by XWnt-5A and hFZ5 (He et al. Science 275, 1652–1654 (1997)).

The existence of other molecules besides FRP that have a FZ CRD but lack the seven transmembrane motif and cytoplasmic tail suggests that there is a subfamily of proteins that function as regulators of Wnt activity. Little is known about the activity of SDF5, which was cloned using the signal sequence trap method (Shirozu et al., (1996) Genomics 37, 273–280). FRZB is a heparin-binding molecule thought to be involved in skeletal morphogenesis (Hoang, B., Moos, M., Jr., Vukicevic, S. & Luyten, F. P. (1996) J Biol Chem 271, 26131–7). Recently Rattner et al. cloned cDNAs encoding the murine homologs of SDF5, FRZB and FRP, and showed that, when artificially linked to the plasma membrane via a glycolipid anchor, SDF5 and FRZB conferred cellular binding to Wg (Rattner, A., Hsieh, J. C., Smallwood, P. M., Gilbert, D. J., Copeland, N. G., Jenkins, N. A. & Nathans, J. (1997) Proc Natl Acad Sci U S A 94, 2859–2863). Thus, it now appears likely that these molecules can interact with Wnt proteins and modulate their activity.

Compositions of the Invention

This invention provides the isolation of human FRP which includes a Wnt binding site (also referred to herein as the cysteine rich domain (CRD), the binding site for Wnt ligands, and the FZ CRD motif) and a hyaluronic acid binding sequence (also referred to herein as the hyaluronic acid binding site and the hyaluronic acid binding domain). FRP is a secreted antagonist to Wnt signaling. In addition, the invention provides FRP polypeptide products of the FRP gene. The invention also provides methods for using the expressed FRP to regulate Wnt signaling, and as a detection means for Wnt proteins and associated processes.

The present invention provides the first human protein product of the FRP gene. In one embodiment, human FRP of the invention includes 313 amino acids. Further it includes a signal sequence, a Wnt binding domain, a hyaluronic acid binding sequence and potential asparagine-linked glycosylation sites. In a preferred embodiment, a human FRP includes a Wnt binding domain as shown in the large shaded region of FIG. 1C and a hyaluronic acid binding sequence as shown in the small shaded region of FIG. 1C. The amino acid sequence of this FRP is shown in FIG. 1C [SEQ ID No. 4].

In another embodiment, a FRP can be joined to another molecule. The FRP may be fused a variety of known fusion protein partners that are well known in the art such as maltose binding protein, LacZ, thioredoxin or an immunoglobulin constant region (Current Protocols In Molecular Biology, Volume 2, Unit 16, Frederick M. Ausubul et al. eds., 1995; Linsley, P. S., Brady, W., Urnes, M., Grosmaire, L., Damle, N., and Ledbetter, L.(1991) J. Exp. Med. 174, 561–566). In a preferred embodiment, this fusion partner is a non-FRP binding molecule so as to prevent difficulties associated with intramolecular interactions. In the alternative, the FRP can be joined to a detectable label such as a radioactive isotope such as $I^{125}$ or $P^{32}$, an enzyme such as horseradish peroxidase or alkaline phosphatase, a fluorophore such as fluorescein isothiocyanate or a chromophore (Current Protocols In Molecular Biology, Volume 2, Units 10,11 and 14, Frederick M. Ausubul et al. eds., 1995; Molecular Cloning, A Laboratory Manual, §12, Tom Maniatis et al. eds., 2d ed. 1989).

The invention also provides peptides and polypeptides having a specific portion of the FRP such as the Wnt binding domain or the hyaluronic acid binding domain (Current Protocols In Molecular Biology, Volume I, Unit 8, Ausubul et al. eds., 1995; Solid Phase Peptide Synthesis, The Peptides Volume II, G. Barany et al., 1980). As with FRP and FRP fusion proteins, these polypeptides can be joined to amino acid tags such as Hemaglutinin or polyhistidine sequences (Krebs et al., Protein Exp. Pur. 6(6), 780–788 (1995); Canfield, V. A., Norbeck, L., and Leveson, R., (1996) Biochemistry 35(45), 14165–14172), larger molecules such as immunoglobulin constant regions, various functional domains from other proteins and known fusion proteins partners (Current Protocols In Molecular Biology, Volume 2, Unit 16, Frederick M. Ausubul et al. eds., 1995; Linsley, P. S., Brady, W., Urnes, M., Grosmaire, L., Damle, N., and Ledbetter, L. (1991) J. Exp. Med. 174, 561–566). In the alternative, the polypeptide can be joined to a detectable label such as a radioactive isotope, an enzyme, a fluorophore or a chromophore.

The polypeptides of the invention can combine in a wide variety of known reagents; typically as a composition comprising an FRP or portion thereof, included therein in a pharmaceutically acceptable carrier such as dextran in a suitable buffer (Current Protocols In Molecular Biology, Volume 3, Appendix A, Frederick M. Ausubul et al. eds., 1995; The Pharmacological Basis of Therapeutics, Alfred G. Gilman et al eds., 8th ed. 1993).

Figure 8C:
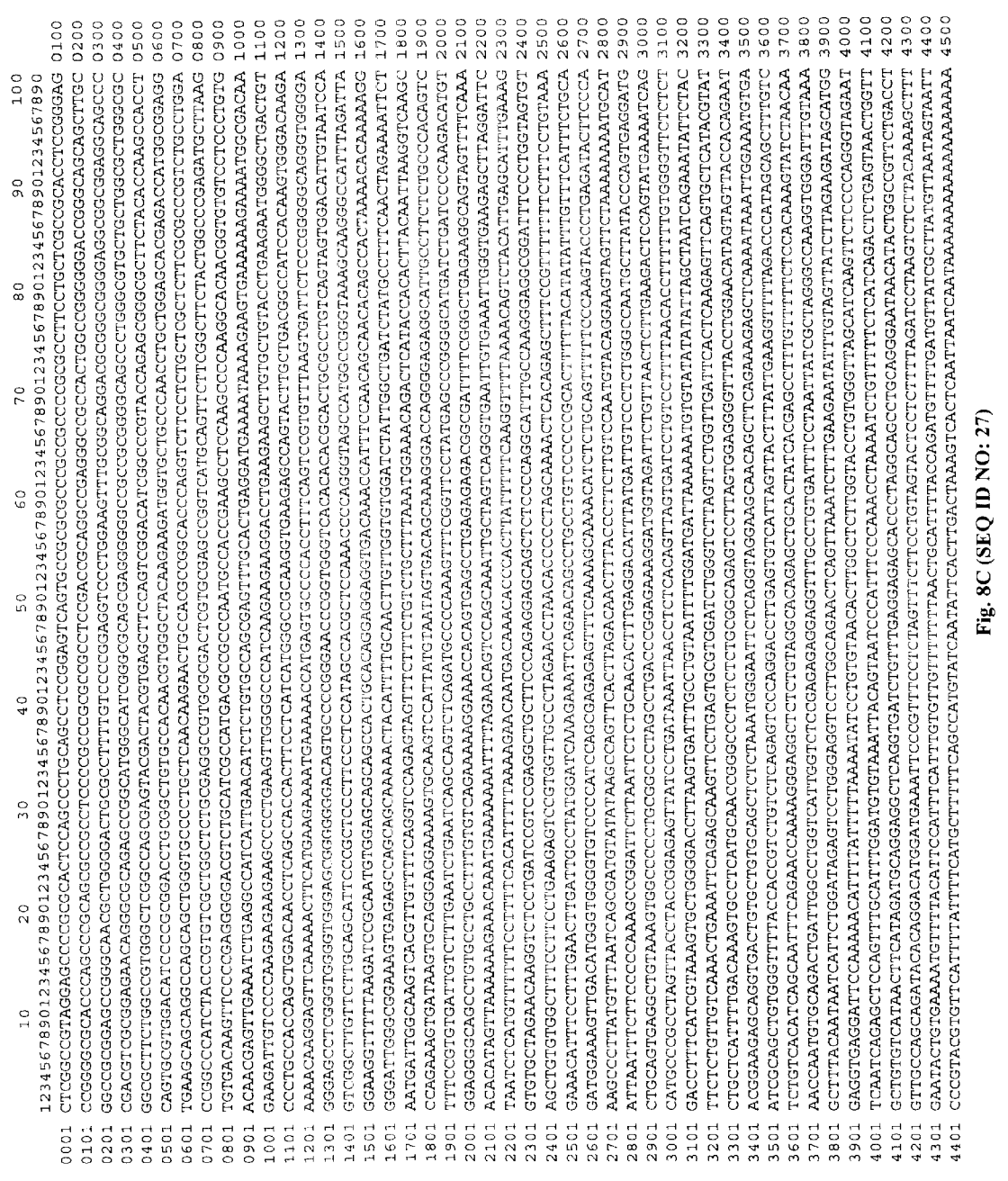

The invention includes single and double stranded nucleic acid molecules having human FRP gene sequences. An illustrative example of such a molecule is shown in FIG. 8. Alternatively, the nucleic acid molecule is represented by the restriction endonuclease map shown in FIG. 1B. These nucleic acid molecules can be RNA such as mRNA or DNA such as cDNA. In a preferred embodiment, the nucleic acid molecule or a hybrid thereof can be joined to a detectable label or tag such as $P^{32}$, biotin or digoxigenein, (Current Protocols In Molecular Biology, Volume I, Unit 3, Frederick M. Ausubul et al. eds., 1995).

In another embodiment, a nucleic acid molecule can include a specific portion of the FRP molecule such as the untranslated regulatory regions, the Wnt binding domain or the hyaluronic acid binding domain. In one such embodiment, the nucleic acid molecule is a deletion mutant which encodes a portion of the region coding for the n-terminus or c-terminus of the FRP protein. In an illustrative embodiment of such a deletion mutant, the deleted sequence encodes the putative FRP signal sequence from FIG. 1C. In another embodiment, the nucleic acid molecule is a deletion mutant in which an internal portion of the FRP coding region has been removed. These FRP molecules can be joined to other nucleic acid molecules such as those encoding fusion protein partners (Molecular Cloning, A Laboratory Manual, §14 and Appendix F, Tom Maniatis et al. eds., 2d ed. 1989). These specific nucleic acid molecules may also be joined to a tag or a detectable label.

Another embodiment provides a complementary nucleic acid probe which specifically hybridizes to FRP nucleic acid sequences (Molecular Cloning, A Laboratory Manual, §7, 9, 14 and Appendix F, Tom Maniatis et al. eds., 2d ed. 1989). In a preferred embodiment, such a probe hybridizes with the Wnt binding domain which encodes amino acids 57–166 as shown in FIG. 1C. For example, the isolated nucleic acid can include DNA encoding FRP polypeptide having amino acid residues 57–166 of FIG. 1C [SEQ ID No. 2] bases 471–800], or is complementary to such encoding nucleic acid sequence, and remains stably bound to it under at least moderate, and optionally, under high stringency conditions. Those skilled in the art appreciate that the stringency of the conditions are manipulated by altering the ionic strength and/or temperature of the hybridization, with for example, conditions of higher stringency employing hybridization conditions wherein the complexes are washed under conditions of lower ionic strength and higher temperatures. Thus, prehybridization and hybridization conditions of 42° C. in 5×SSPE, 0.3% SDS, 200 µg/ml sheared and denatured salmon sperm DNA, and either 50, 35 or 25% formamide illustrate high, medium and low stringencies, respectively. Variations on such condition are well known in the art (see e.g. U.S. Pat. Nos. 5,688,663 and 5,429,921).

Another embodiment provides an antisense nucleic acid which specifically hybridizes to FRP mRNA (Chen, Z., Fischer, R., Riggs, C., Rhim, J. and Lautenberger, J. (1997) Cancer Research 57, 2013–2019; Aviezer D., lozzo, R. V., Noonan, D., and Yayon, a., (1997), Mol. Cell Biol. 17(4), 1938–1946). Antisense technology entails the administration of exogenous oligonucleotides which bind to a target polynucleotide located within the cells. The term "antisense" refers to the fact that such oligonucleotides are complementary to their intracellular targets, e.g., FRP. See for example, Jack Cohen, OLIGODEOXYNUCLEOTIDES, Antisense Inhibitors of Gene Expression, CRC Press, 1989; and Synthesis 1:1–5 (1988). The FRP antisense oligonucleotides of the present invention include derivatives such as S-oligonucleotides (phosphorothioate derivatives or S-oligos, see, Jack Cohen, supra) which exhibit enhanced cancer cell growth inhibitory action.

S-oligos (nucleoside phosphorothioates) are isoelectronic analogs of an oligonucleotide (O-oligo) in which a non-bridging oxygen atom of the phosphate group is replaced by a sulfur atom. The S-oligos of the present invention may be prepared by treatment of the corresponding O-oligos with 3H-1,2-benzodithiol-3-one-1,1-dioxide which is a sulfur transfer reagent. See Iyer, R. P. et al, J. Org. Chem. 55:4693–4698 (1990); and Iyer, R. P. et al., J. Am. Chem. Soc. 112:1253–1254 (1990), the disclosures of which are fully incorporated by reference herein.

The FRP antisense oligonucleotides of the present invention may be RNA or DNA which is complementary to and stably hybridizes with the first 100 N-terminal codons or last 100 C-terminal codons of the FRP genome or the corresponding mRNA. While absolute complementarity (i.e. a complementary interaction between all polynucleotide moieties) of antisense oligonucleotides is not required, high degrees of complementarity are preferred. Use of an oligonucleotide complementary to this region allows for the selective hybridization to FRP mRNA and not to mRNA specifying other regulatory subunits of protein kinase. Preferably, the FRP antisense oligonucleotides of the present invention are a 15 to 30-mer fragment of the antisense DNA molecule having which hybridizes to FRP mRNA. Optionally, FRP antisense oligonucleotide is a 30-mer oligonucleotide which is complementary to a region in the first 10 N-terminal codons and last 10 C-terminal codons of FRP. Alternatively, the antisense molecules are modified to employ ribozymes in the inhibition of FRP expression. L. A. Couture & D. T. Stinchcomb; *Trends Genet* 12: 510–515 (1996).

The invention further provides an expression vector such as bacteriophage lambda gt11, plasmid vectors such as pcDNA, CDM8 and PNTK or retroviral vectors such as those of the pBABE series comprising the FRP cDNA or a portion thereof (*Current Protocols In Molecular Biology*, Volume I, Units 5, 9, 12, Frederick M. Ausubul et al. eds., 1995). Additionally, the invention provides a host vector system in which the expression vector is transfected into a compatible host cell including bacterial strains such as the DH5α strain of *E. coli*, yeast strains such as EGY48, animal cell lines such as CHO cells and human cells such as HELA cells (*Current Protocols In Molecular Biology*, Volume II, Units 13–16, Frederick M. Ausubul et al. eds., 1995; *Molecular Cloning, A Laboratory Manual*, §16 and 17, Tom Maniatis et al. eds., 2d ed. 1989). Additionally, the invention provides a method of producing a protein comprising growing the transfected host cell, thereby producing the protein that may be recovered and utilized in a wide variety of applications (*Current Protocols In Molecular Biology*, Volume II, Unit 16, Frederick M. Ausubul et al. eds., 1995).

As discussed in Example 7, an illustrative embodiment of a recombinant expression system is the MDCK/FRP recombinant expression system. Optimization of the MDCK/FRP recombinant expression system may be carried out by techniques known in the art. For example, immunological methods may be employed to screen subpopulations of transfectants to measure the amount of FRP released into the medium. By successive screening and subculturing, clonal lines expressing greater amounts of FRP protein may be obtained. In addition, the illustrative regimen for harvesting conditioned medium involves subculturing into a large number of T-175 flasks and cycling monolayers from serum-containing to serum-free medium several times may be streamlined by utilizing alternative devices such as cell factories and/or microcarriers, and then determine whether multiple successive rounds of FRP-rich, serum-free conditioned medium can be collected once confluent monolayers are generated with serum-containing medium. Such measures can reduce the time and cost of producing large quantities of recombinant protein to be used for structural analysis, biochemical and biological studies.

Figure 12:
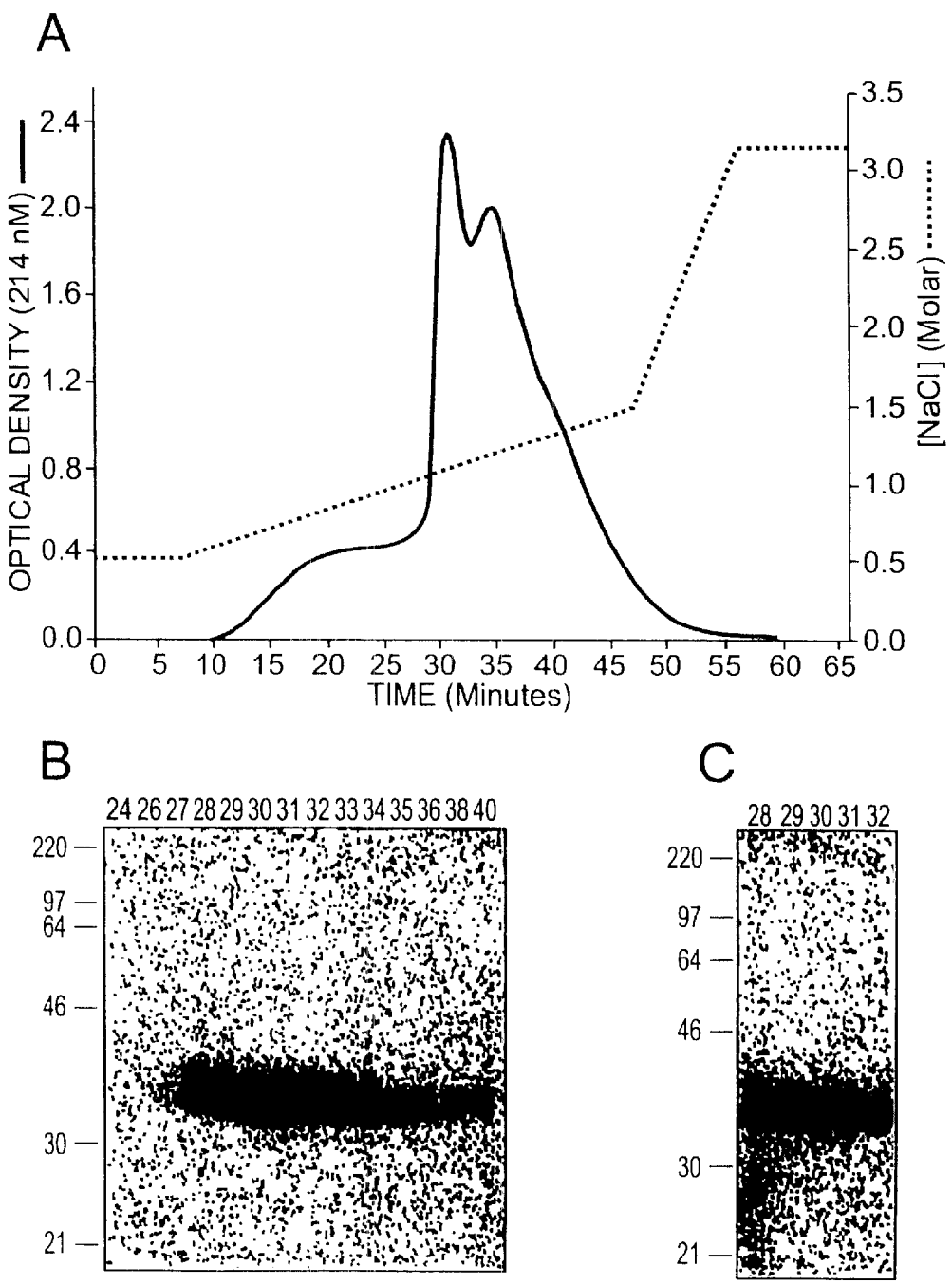
FIG. 12A shows an elution profile of recombinant FRP.
FIG. 12B shows immunoblotting of recombinant FRP with peptide antiserum.
FIG. 12C shows a polyacrrylamide gel of silver stained recombinant FRP.

The asymmetry of FRP elution in the heparin-HPLC optical density profile, and the breadth of the FRP-crossreactive bands suggest that current preparations of recombinant protein are heterogeneous (FIG. 12). This is also evident in naturally occurring FRP, as amino-terminal sequence analysis revealed two distinct sequences that differed from each other by a three-amino acid stagger. Finch, et al., P.N.A.S. 94: 6770–6775 (1997). To identify the source of this heterogeneity, amino acid sequence analysis of purified recombinant FRP protein can be performed to evaluate the purity of the preparation and indicate whether such differences account for at least some of the apparent heterogeneity. Given the presence of two potential asparagine-linked glycosylation sites in the FRP sequence, variation in glycosylation also might contribute to heterogeneity. This possibility can be tested by expressing site-directed mutants lacking the glycosylation sites; the mobility and breadth of immunocrossreactive bands corresponding to these derivatives will indicate whether FRP normally is glycosylated at these sites and whether this is responsible for heterogeneity. The resolution of putative FRP variants by additional chromatography (ion exchange or hydrophobic interaction, for instance) or their elimination by removal of glycosylation sites is also possible using art accepted techniques and will facilitate structural analysis by methods such as X-ray diffraction or NMR that require homogeneous preparations.

Figure 13:
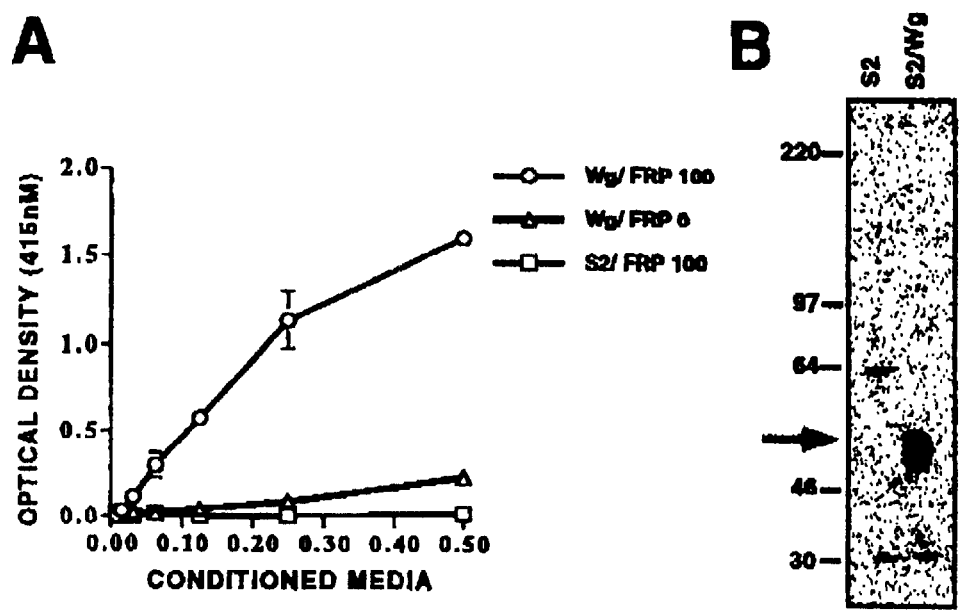
FIG. 13A shows the interaction between recombinant FRP and Wg in an ELISA format.
FIG. 13B shows the immunoblotting of Wg.

The MDCK/FRP expression system can be used to produce FRP derivatives for structural analysis. Besides mutants lacking glycosylation sites, truncated variants may can be expressed to assess the significance of different structural elements. While the epitopes and regions associated with the function and integrity of the cysteine-rich domain (CRD) are of significant interest, other regions of the molecule presumably responsible for binding to proteoglycan can also be examined. Such structural studies can be used to determine the disulfide-bonding pattern in the CRD, and consequently, to engineer substitutions of paired cysteine residues to determine the significance of individual disulfide bond-dependent peptide loops. Derivatives can be tested in Wnt-binding ELISAs (for example as shown in FIG. 13) and in biological assays involving β-catenin stabilization or other manifestations of Wnt activity. Miller et al., Genes Dev. 10: 2527–2539, (1996). The ELISA format disclosed in Example 8 is particularly well suited for a quantitative comparison of the FRP analogs. Because the heparin-binding and immunological properties of the derivatives will vary, one can express them in pcDNA vectors designed to add histidine and Myc tags to the recombinant protein. In this way, it is possible to purify the various derivatives on nickel-affinity resin and visualize them with antibody directed against the Myc or histidine epitopes.

Reports indicate that there are several other secreted Frizzled-related proteins of similar size and perhaps function. (See e.g., Rattner, et al., P.N.A.S. 94:2859–2863 (1997)). The MDCK/pcDNA expression system is well suited for the production of other secreted FRP molecules. In this way one can compare and contrast the binding and biological properties of multiple secreted FRPs to better understand their unique functions.

Notwithstanding the results obtained with FRP expression in MDCK cells, other recombinant systems may prove more useful for certain applications. For example, for NMR solution analysis, proteins must be uniformly labeled with various non-standard isotopes ($^2$H, $^{13}$C, $^{15}$N). The medium required to achieve this labeling in mammalian cell culture is very expensive. As an alternative, one may express CRD-containing constructs in yeast (*Pichia pasteuris*), bacteria such as *E.coli* or baculovirus/insect cell expression systems, where isotope-labeling should be more straightforward.

Further, in accordance with the practice of this invention, FRP molecules of the invention can have amino acid substitutions in the amino acid sequence shown in FIG. 1C (*Current Protocols In Molecular Biology*, Volume I, Unit 8, Frederick M. Ausubul et al. eds., 1995). The only requirement being that substitutions result in human FRP that retains the ability to bind the Wnt molecule. These amino acid substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

FRP derivatives can be made using methods known in the art such as site-directed mutagenesis, alanine scanning, and PCR mutagenesis. Site-directed mutagenesis [Carter et al., *Nucl. Acids Res.*, 13.4331 (1986); Zoller et al., *Nucl. Acids Res.*, 10:6487 (1987)], cassette mutagenesis [Wells et al., Gene, 34:315 (1985)], restriction selection mutagenesis [Wells et al., *Philos. Trans. R. Soc. London SerA*, 317:415 (1986)] or other known techniques can be performed on the cloned DNA to produce the FRP variant DNA. Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W. H. Freeman & Co., N.Y.); Chothia, J. Mol. Biol., 150:1 (1976)]. If alanine substitution does not yield adequate amounts of variant, an isoteric amino acid can be used.

As discussed above, redundancy in the genetic code permits variation in FRP gene sequences. In particular, one skilled in the art will recognize specific codon preferences by a specific host species and can adapt the disclosed sequence as preferred for a desired host. For example, preferred codon sequences typically have rare codons (i.e., codons having a useage frequency of less than about 20% in known sequences of the desired host) replaced with higher frequency codons. Codon preferences for a specific organism may be calculated, for example, by utilizing codon usage tables available on the INTERNET. Nucleotide sequences which have been optimized for a particular host species by replacing any codons having a useage frequency of less than about 20% are referred to herein as "codon optimized sequences."

Additional sequence modifications are known to enhance protein expression in a cellular host. These include elimination of sequences encoding spurious polyadenylation signals, exon/intron splice site signals, transposon-like repeats, and/or other such well-characterized sequences which may be deleterious to gene expression. The GC content of the sequence may be adjusted to levels average for a given cellular host, as calculated by reference to known genes expressed in the host cell. Where possible, the sequence may also be modified to avoid predicted hairpin secondary mRNA structures. Other useful modifications include the addition of a translational initiation consensus sequence at the start of the open reading frame, as described in Kozak, *Mol. Cell Biol.*, 9:5073–5080 (1989). Nucleotide sequences which have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequence."

The present invention also provides an antibody which specifically recognizes and binds an epitope on a FRP, e.g. the Wnt binding domain or the hyaluronic acid binding domain of an FRP (*Current Protocols In Molecular Biology*, Volume II, Unit 11, Frederick M. Ausubul et al. eds., 1995; Kohler, G., and Milstein, C., Nature, (1975) 256, 495–497). A rabbit polyclonal antiserum raised against a synthetic peptide corresponding to a portion of the FRP amino-terminal sequence has been used for the detection of FRP by immunoblotting, immunoprecipitation and ELISA. A rabbit polyclonal antiserum raised against full-length recombinant FRP has also been generated. A related embodiment consists of an anti-idiotype antibody which specifically recognizes and binds antibody generated to an FRP epitope. Related embodiments further provide for single chain and human-ized forms of these antibodies (U.S. Pat. No. 5,569,825 to Lonberg et al., issued Oct. 29, 1996; Bei, R., Schlom, J., and Kashmiri, S., (1995) *J. Immunol. Methods* 186(2) 245–255; Park, S., Ryu, C. J., Gripon, P., Guguen-Guillouzo, C., and Hong, H. J. (1996) *Hybridoma* 15(6) 435–441). These antibodies may be linked to a detectable label such as one selected from the group consisting of radioactive isotopes, enzymes, fluorophores or chromophores (*Current Protocols*

*In Molecular Biology*, Volume II, Units 11, 14, Frederick M. Ausubul et al. eds., 1995).

Methods of the Invention

The invention further provides methods of modulating cellular development. In one embodiment, the method includes the steps of contacting a Wnt molecule with FRP or a portion of the FRP molecule. This contact blocks an interaction between the Wnt molecule and a Fz receptor, thereby inhibiting a cellular process such as proliferation and/or differentiation and/or migration (Tan, P., Anasetti, C., Hansen, J., Melrose, J., Brunvand, M., Bradshaw, J., Ledbetter, J. and Linsley, P., (1993) J. Exp. Med. 177, 165–173). In a preferred embodiment of this method, the cell is a tumor cell (Estrov, Z. Kurzrock, R., Estey, E. Wetzler, M., Ferrajoli, A., Harris, D., Blake, M., Gutterman, J. U. and Talpaz, M. (1992) *Blood* 79(8) 1938–1945).

The invention further provides a method for blocking Wnt and Fz receptor binding. This method involves administering FRP to a subject. The FRP so administered must be in an amount sufficient to block the binding between a Wnt molecule and a Fz receptor.

The present invention also provides a method for modulating cellular differentiation in a subject. One such method includes administering cells transfected with an FRP gene (*Current Protocols In Molecular Biology*, Volume I, Unit 9, Frederick M. Ausubul et al. eds., 1995). Once administered, these transfected cells express recombinant FRP in an amount sufficient to block the interactions between a Wnt molecule and Wnt receptor, thereby inhibiting cell proliferation and/or differentiation. In these methods, the FRP gene can be manipulated in one of a number of ways as is well known in the art such as through the use of a plasmid or viral vectors (*Molecular Cloning, A Laboratory Manual*, §1 and Appendix F, Tom Maniatis et al. eds., 2d ed. 1989). The FRP gene can be inserted into donor cells by a nonviral physical transfection of DNA, by microinjection of RNA or DNA, by electroporation, via chemically mediated transfection or by one of a variety of related methods of manipulation (*Molecular Cloning, A Laboratory Manual*, §16, Tom Maniatis et al. eds., 2d ed. 1989).

Using the molecules disclosed herein, the invention provides methods to investigate the impact of FRP on effectors of Wnt signaling. In particular, one can measure the steady-state level of soluble β-catenin in cells exposed to Wnt stimulation in the presence or absence of FRP. As in a study showing that Drosophila Frizzled 2 (Df2) can mediate Wg-dependent stabilization of armadillo (Drosophila beta-catenin homolog), one can treat clone 8 cells expressing endogenous Dfz2 and/or Dfz2-transfected S2 cells with Wg-containing medium preincubated with FRP or vehicle control. Bhanot et al., Nature 382: 225–230, (1996). If FRP functions as a Wg antagonist in this cellular system, consistent with its effect in the Xenopus embryo dorsal axis duplication assay, lower levels of armadillo will be seen when cells are exposed to medium preincubated with FRP. Such a result was recently described in another experimental model: MCF-7 human mammary carcinoma cells transfected with an FRP construct showed a marked decrease in cellular β-catenin relative to vector control transfectants, Melkonyan, et al., P.N.A.S. 94:13636–13641 (1997) (in this article FRP was referred to as SARP2). Thus, one can test the ability of recombinant FRP protein to reduce the β-catenin content of this and other cell lines. If documented, this can serve as a convenient, semi-quantitative, functional assay of FRP derivatives. As additional markers of Wnt signaling are delineated, one can test the effect of FRP on these parameters. This can involve Tcf/LEF-1-beta-catenin-dependent gene expression (see e.g., Molenaar, et al., Cell 86:391–399 (1996), changes in cytoskeleton or cell cycle progression. The intent will be to determine whether all manifestations of Wnt signaling are blocked by FRP, or only certain pathways.

The invention further provides a method for determining the presence of FRP nucleic acid and peptide sequences in a sample. This method includes screening a sample with FRP nucleic acid molecules or antibodies via procedures such as reverse transcriptase Polymerase Chain Reaction, and northern and Southern and western protocols as is well known in the art (*Current Protocols In Molecular Biology*, Volume I and III, Units 16, 2 and 4, Frederick M. Ausubul et al. eds., 1995).

As disclosed in Example 3 below, Northern blot analysis of RNA from adult and embryonic organs indicate that FRP is expressed widely, though not ubiquitously in humans. Subsequent in situ hybridization analysis of mouse embryonic tissue confirms this interpretation (see Example 3 below). By surveying the pattern of FRP expression during development and in the adult with a combination of in situ hybridization and immunohistochemistry, one can identify a set of contexts in which this gene is active. Additionally, one can extend the analysis to models of wound repair in which processes such as cell proliferation, migration and apoptosis are particularly active.

Similarly, FRP sequences and expression can be examined in tumor specimens. For example tumor samples can be screened for evidence of FRP mutations or hypermethylation of regulatory regions associated with the absence of gene expression (see e.g. *Current Protocols In Molecular Biology*, Volumes I and II, Units 3 and 12, Frederick M. Ausubul et al. eds., 1995).

A number of approaches that are well known in the art can be taken to study the regulation of FRP expression. An illustrative approach involves the use of various cytokines and/or growth conditions to assess the impact of different external agents or environmental factors on expression. Multiple FRP-expressing cells can be included in such analyses, as preliminary observations suggest that cells vary in their response to these kinds of stimuli. Complementary to these experiments is the identification and analysis of the FRP promoter region as shown in FIG. 11. Sequencing of the presumptive promoter lying 5' upstream of the coding sequence can be followed by subcloning into reporter constructs and transfection into cell lines for functional analysis. Upon confirmation of promoter activity, one can pinpoint the sequences responsible for regulating expression by a combination of deletional analysis and computer-based searches to locate potential binding sites for transcription factors. If putative binding sites are identified, their relevance can be tested by expression of corresponding reporter constructs, gel shift and supershift experiments, and co-expression of promoter reporter constructs with mRNA promoting the expression of the corresponding transcription factor. Xu, et al., P.N.A.S. 93:834–838 (1996). The functionality of putative promoter sequences with respect to determining the spatiotemporal distribution of FRP expression can also be tested by using reporter constructs in transgenic mice.

The invention further provides a method for determining the presence of a Wnt molecule in a sample. This method includes adding a FRP to the sample. The FRP so added can recognize and bind Wnt molecule that is present in the sample. This binding results in a FRP/Wnt complex that can be detected. The presence of the complex is indicative of the presence of the Wnt molecule in the sample. In a variation of this method, detection includes contacting the complex with an antibody which recognizes and binds the complex (*Current Protocols In Molecular Biology*, Volume II, Unit 11, Frederick M. Ausubul et al. eds., 1995). The antibody/complex so bound can be detected. The antibody can be either monoclonal or polyclonal. Further, the antibody can be bound to a matrix such agarose, sepharose, or a related type of bead (*Current Protocols In Molecular Biology*, Volume II, Unit 11, Frederick M. Ausubul et al. eds., 1995). In addition, the antibody may be labeled with a detectable marker such as a radioactive isotope, an enzyme, a fluorophore or a chromophore.

The preparation of ample quantities of purified FRP protein as disclosed in Example 7 below is useful for studying the presumed interactions of FRP and Wnt polypeptides. With sufficient amounts of FRP, multiple experimental designs can be employed to test the hypothesis that FRP and Wnts engage in a direct interaction. The affinity and specificity of the suspected binding interactions can be determined, as well as the potential requirement for co-factors such as proteoglycan. Experimental models that rely on constitutive expression of FRP may yield important information about the effects of FRP on cell function. However, use of recombinant protein will enable one skilled in the art to control the timing and amount of FRP exposure, and consequently, assess its effects in a more quantitative manner. Moreover, a satisfactory recombinant expression system will be the cornerstone of detailed structure-function analysis.

As illustrated in Example 8, the invention provides methods to evaluate the interaction between FRP and FRP-binding partners. The results obtained with the FRP-Wg binding ELISA in Example 8 establish that this is a useful model for the study of FRP interactions with Wnt proteins. A variety of modifications of such studies are contemplated such as those that identify cofactors in these interactions. For example, the Wg content of purified and crude preparations can be normalized by immunoblot analysis, and the FRP-binding of both Wg samples can be compared in the ELISA disclosed in Example 8. Because the conditions used to purify Wg are relatively gentle, any appreciable decrease in binding activity of the enriched Wg preparation could be attributable to loss of a cryptic co-factor rather than denaturation of the Wg protein. If such a loss were observed, a leading candidate for the putative co-factor would be soluble glycosaminoglycan. To examine this, one can treat the crude material with heparitinases, or add exogenous proteoglycan to purified Wg in the ELISA and observing whether binding activity is restored.

Utilizing purified Wg one can estimate the affinity of the apparent FRP-Wg interaction. Either by using purified Wg directly in the FRP-binding ELISA, or simply to quantify the amounts of Wg in the starting material and bound in the ELISA microtiter well, it is possible to determine the concentration of bound versus free Wg in the assay and perform a Scatchard analysis to provide a useful indication of the affinity characterizing FRP-Wnt interactions.

As mentioned above, the ELISA format illustrated in Example 8 can be employed to examine Wnt binding of various FRP analogs. One can investigate the Wg-binding of FRP truncation mutants and site-directed variants lacking the asparagine-linked glycosylation sites. Further, the binding of additional site-directed FRP mutants and other secreted FRPs can be assessed. The substitution other Wnt family members for Wg in the binding assay will provide additional useful information.

Cell-free binding assays that complement the disclosed ELISA include ligand-receptor, cross-linking analysis. While in classical covalent binding studies a radioisotope-labeled ligand is employed, one can use $^{125}$I-FRP as tracer in combination with unlabeled Wg (or other available soluble Wnt protein) and a cross-linking agent such as bis(sulfosuccinimidyl) suberate. Subsequent immunoprecipitation with antibody to Wg (or the appropriate epitope if a tagged Wnt molecule is involved), followed by SDS-PAGE and autoradiography will provide evidence of a direct FRP-Wg interaction.

Cellular binding assays can also be performed, using labeled FRP as tracer. While Wnt protein may be accessible at the cell surface, alternative models such as fusion proteins can be employed to anchor Wnt in the membrane and facilitate detection. Parkin, et al., Genes Dev. 7:2181–2193 (1993). While in such studies, the ligand-receptor relationship of Wg and FRP will be reversed; nonetheless, binding will occur and be suitable for Scatchard analysis. A quantitative measure of this condition can be obtained by assaying Wg-binding of the tracer in the ELISA disclosed in Example 8.

The present invention also provides a method for monitoring the course of a neoplastic condition in a subject. This method includes quantitatively determining in a first sample, from the subject, the presence of a Wnt molecule by detection method such as those commonly utilized in immunohistochemistry (*Current Protocols In Molecular Biology*, Volume II, Unit 14, Frederick M. Ausubul et al. eds., 1995). The amount so determined is compared with an amount present in a second sample from the subject. Each sample is taken at a different point in time. A difference in the amounts determined is indicative of the course of the neoplastic condition.

As outlined above, FRP plays a role in neoplasia. Ectopic expression of Wnt-l caused hyperplasia and adenocarcinoma in mouse mammary gland. (See e.g., Tsukamoto, et al., Cell 55:619–625 (1988)). Stabilization of beta-catenin-a hallmark of Wnt signaling—occurs with high frequency either as a consequence of mutation in the beta-catenin or APC genes in human colon cancer and melanoma. (See e.g., Korinek, et al., Science 275:1784–1787 (1997)). The ability of FRP to inhibit Wnt signaling in the Xenopus axis duplication assay (Finch, et al., P.N.A.S. 94:6770–6775 (1997) and to decrease intracellular beta-catenin concentration in MCF-7 transfectants (Melkonyan, et al., P.N.A.S. 94:13636–13641 (1997)) suggests that FRP might function to suppress signaling in a pathway that can contribute to malignancy. FRP expression in MCF-7 cells apparently caused an increase in the number of cells undergoing apoptosis (Melkonyan, et al., P.N.A.S. 94:13636–13641 (1997)). Moreover, deletions or loss of heterozygosity have been described at the FRP chromosomal locus, 8p11.1–12, in association with kidney, breast, prostate, bladder and pancreas carcinoma and astrocytoma. See e.g., Mitelman, et al., Nature Genet 15: 417–474 (1997). Translocations at this locus were reported to occur in cases of myeloproliferative disease, T-ALL and T-PLL (Mitelman, et al., Nature Genet 15: 417–474 (1997)). Taken together, these observations raise the possibility that FRP may act as a tumor suppressor by inhibiting Wnt signaling and promoting apoptosis; loss of this function foster tumorigenesis.

One can perform a screen of FRP mRNA expression in a large sample of tumor cell lines. This can be accompanied by Southern blotting of restriction digests of genomic DNA from lines lacking FRP expression to look for gross changes in FRP gene structure. If no differences are seen relative to a normal control, more sensitive methods of detecting point mutations such as single strand conformation polymorphism (SSCP) can be used. Humphries, et al. Clin. Chem. 43:427–435 (1997). To facilitate this analysis, exon-intron boundaries of the FRP gene can be determined; and with this information, PCR primers can be designed to assist in the investigation of the gene structure of coding sequence. Any evidence of mutation can be confirmed by nucleotide sequence analysis. In addition to studying cell lines, one can screen paired tumor-bearing and tumor-free tissue specimens from individual patients. Gene targeting of FRP can also provide evidence of tumor suppressor function, if it resulted in mice that were prone to malignancy. Animals with this phenotype will serve as a useful model for the investigation of molecular events that culminate in neoplasia.

The invention also provides screening method for molecules that react with a Wnt or FRP molecules by a two-hybrid screen (Janouex-Lerosey I., Jollivet, F., Camonis, J., Marche, P. N., and Goud, B., (1995) J. Biol. Chem. 270(24), 14801–14808) or by Western or Far Western techniques (*Current Protocols In Molecular Biology*, Volume I, Unit 11, Frederick M. Ausubul et al. eds., 1995; Takayama, S., and Reed, J. C. (1997) Methods Mol. Biol. 69, 171–184). One method includes separately contacting each of a plurality of samples. Each sample contains a predefined number of cells. Further, each sample contains a predetermined amount of a different molecule to be tested.

Use of FRP Upstream Control Sequences for Evaluating Regulatory Processes

The genomic FRP control sequences of the present invention, whether positive, negative, or both, may be employed in numerous various combinations and organizations to assess the regulation of FRP. Moreover, in the context of multiple unit embodiments and/or in embodiments which incorporate both positive and negative control units, there is no requirement that such units be arranged in an adjacent head-to-head or head-to-tail construction in that the improved regulation capability of such multiple units is conferred virtually independent of the location of such multiple sequences with respect to each other. Moreover, there is no requirement that each unit include the same positive or negative element. All that is required is that such sequences be located upstream of and sufficiently proximal to a transcription initiation site.

To evaluate FRP regulatory elements in the context of heterologous genes, one simply obtains the structural gene and locates one or more of such control sequences upstream of a transcription initiation site. Additionally, as is known in the art, it is generally desirable to include TATA-box sequences upstream of and proximal to a transcription initiation site of the heterologous structural gene. Such sequences may be synthesized and inserted in the same manner as the novel control sequences. Alternatively, one may desire to simply employ the TATA sequences normally associated with the heterologous gene. In any event, TATA sequences are most desirably located between about 20 and 30 nucleotides upstream of transcription initiation.

Preferably the heterologous gene is a gene which encodes an enzyme which produces colorimetric or fluorometric change in the host cell which is detectable by in situ analysis and which is a quantitative or semi-quantitative function of transcriptional activation. Exemplary enzymes include esterases, phosphatases, proteases (tissue plasminogen activator or urokinase) and other enzymes capable of being detected by activity which generates a chromophore or fluorophore as will be known to those skilled in the art. A preferred example is *E. coli* β-galactosidase. This enzyme produces a color change upon cleavage of the indigogenic substrate indolyl-B-D-galactoside by cells bearing β-galactosidase (see, e.g., Goring et al., Science, 235:456–458 (1987) and Price et al., Proc. Natl. Acad. Sci. U.S.A., 84:156–160 (1987)). Thus, this enzyme facilitates automatic plate reader analysis of FRP control sequence mediated expression directly in microtiter wells containing transformants treated with candidate activators. Also, since the endogenous β-galactosidase activity in mammalian cells ordinarily is quite low, the analytic screening system using β-galactosidase is not hampered by host cell background.

Another class of reporter genes which confer detectable characteristics on a host cell are those which encode polypeptides, generally enzymes, which render their transformants resistant against toxins, e.g., the neo gene which protects host cells against toxic levels of the antibiotic G418; a gene encoding dihydrofolate reductase, which confers resistance to methotrexate, or the chloramphenicol acetyltransferase (CAT) gene (Osborne et al., Cell, 42:203–212 (1985)). Genes of this class are not preferred since the phenotype (resistance) does not provide a convenient or rapid quantitative output. Resistance to antibiotic or toxin requires days of culture to confirm, or complex assay procedures if other than a biological determination is to be made.

Use of FRP Nucleic Acids in the Generation of Transgenic Animals

Nucleic acids which encode FRP or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding FRP can be used to clone genomic DNA encoding FRP in accordance with established techniques and the genomic or cDNA sequences can then be used to generate transgenic animals that contain cells which express DNA encoding FRP. Methods for generating transgenic animals, particularly animals such as mice or rats, have become conventional in the art and are described, for example, in U.S. Pat. Nos. 4,736,866 and 4,870,009. Typically, particular cells would be targeted for FRP transgene incorporation with inducible and tissue-specific control elements. Illustrative inducible and tissue specific control sequences include the mouse mammary tumor long terminal repeat (MMTV LTR) and the tetracycline elements respectively (see e.g. Hennighausen et al., J Cell Biochem Dec;59 (4):463–72 (1995). Transgenic animals that include a copy of a transgene encoding FRP introduced into the germ line of the animal at an embryonic stage can be used to examine the effect of increased expression of DNA encoding FRP. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of FRP can be used to construct a FRP "knock out" animal which has a defective or altered gene encoding FRP as a result of homologous recombination between the endogenous gene encoding FRP and altered genomic DNA encoding FRP introduced into an embryonic cell of the animal. For example, cDNA encoding FRP can be used to clone genomic DNA encoding FRP in accordance with established techniques. A portion of the genomic DNA encoding FRP can be deleted or replaced with another gene, such as a gene encoding a selectable marker which can be used to monitor integration. Typically, several kilobases of unaltered flanking DNA (both at the 5' and 3' ends) are included in the vector (see e.g., Thomas and Capecchi, Cell, 51:503 (1987) for a description of homologous recombination vectors). The vector is introduced into an embryonic stem cell line (e.g., by electroporation) and cells in which the introduced DNA has homologously recombined with the endogenous DNA are selected (see e.g., Li et al., Cell, 69:915 (1992)). The selected cells are then injected into a blastocyst of an animal (e.g., a mouse or rat) to form aggregation chimeras [see e.g., Bradley, in Teratocarcinomas and Embryonic Stem Cells: A Practical Approach, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the FRP polypeptide.

Advantages of the Invention

FRP is a previously undescribed human gene product that is involved in regulating cellular growth and differentiation. This novel polypeptide antagonizes Wnt action. As a secreted antagonist which competes for a factor known to regulate cellular growth and development, FRP is a prototype for molecules that function as endogenous regulators of cytokine activity. As such, this novel protein has a variety of applications in the identification, characterization and regulation of activities associated with the Wnt family of cytokines.

EXAMPLES

Throughout this application, various publications are referenced. The disclosures of these publications in their entireties are hereby incorporated by reference into this application in order to more fully describe the state of the art to which the invention pertains. The following examples are presented to illustrate the present invention and to assist one of ordinary skill in making and using the same. The examples are not intended in any way to otherwise limit the scope of the invention.

Example 1

Purification and Physical Characterization of the FRP Protein

Conditioned-medium collection, ultrafiltration, heparin-Sepharose affinity chromatography, and SDS/PAGE were performed as described (Rubin, J. S., Osada, H., Finch, P. W., Taylor, W. G., Rudikoff, S. & Aaronson, S. A. (1989) Proc Natl Acad Sci U S A 86, 802–6). Hepatocyte growth factor/scatter factor (HGF/SF)-containing fractions were identified by immunoblotting. Occasionally heparin-Sepharose fractions were processed by reverse-phase $C_4$ HPLC (Rubin, J. S., Osada, H., Finch, P. W., Taylor, W. G., Rudikoff, S. & Aaronson, S. A. (1989) Proc Natl Acad Sci U S A 86, 802–6) to enhance purity of FRP. Gels were fixed and silver-stained using the reagents and protocol from Bio-Rad.

During the isolation of HGF/SF from human embryonic lung fibroblast culture fluid, a 36 kDa polypeptide which co-purified with HGF/SF following a variety of chromatography procedures was identified (Rubin, J. S., Chan, A. M., Bottaro, D. P., Burgess, W. H. Taylor, W. G., Cech, A. C., Hirshfield, D. W., Wong, J., Miki, T., Finch, P. W. & et al. (1991) Proc Natl Acad Sci U S A 88, 415–9). Because the co-migration of this protein and HGF/SF suggested that it might regulate growth factor activity, a preparative scheme was devised to obtain sufficient quantities for study. This was accomplished by conservative pooling of fractions eluting from heparin-Sepharose resin with 1.0 M NaCl, once it became evident that a portion of the 36 kDa protein emerged after the HGF/SF-containing fractions. Protein obtained in this manner was sufficiently pure and abundant for structural and limited functional analysis (FIG. 1A).

Microsequencing

Approximately 30 μg of protein was loaded onto an Applied Biosystems gas-phase protein sequenator. Forty rounds of Edman degradation were carried out, and phenylthiohydantoin amino acid derivatives were identified with an automated on-line HPLC column (model 120A, Applied Biosystems).

FIG. 1 provides illustrations of these protocols and results. FIG. 1 consists of a series of panels. Panel (A) shows an SDS/PAGE analysis of heparin-Sepharose purified FRP. Approximately 200 ng of protein was resolved in a 4–20% polyacrylamide minigel (Novex) under reducing (+) or non-reducing (−) conditions, and subsequently stained with silver. The position of molecular mass markers is indicated at the right.

Example 2

Molecular Cloning and Characterization of FRP Nucleic Acid Sequences

Four pools of 26-base degenerate oligonucleotides were synthesized on the basis of either of two segments of amino acid sequence determined by microsequencing of purified FRP. Two pools corresponding to the sequence NVGYKKMVL [SEQ ID No. 5] contained all possible codon combinations except for the substitution of inosine residues in the third positions of the codons for the first Val and Gly; one subset terminated with bases CT and the other with TT. Two additional pools, corresponding to the sequence FYTKPPQXV [SEQ ID No. 6], contained all possible codon combinations except for the substitution of inosine residues in the third positions of the codons for both Pro residues; one subset contained four codon options for Ser in the X position, while the other had the remaining two. Oligonucleotide pools were labeled and used to screen an oligo (dT)-primed M426 cDNA library as previously described (Finch, P. W., Rubin, J. S., Miki, T., Ron, D. & Aaronson, S. A. (1989) Science 245, 752 5).

Microsequencing of the purified 36 kDa protein yielded two amino-terminal sequences, one beginning three residues downstream from the other. Positive identifications were made in 37 of the first 40 cycles of Edman degradation, as follows: FQSDIGPYQSGRFYTKPPQXVDIPADLR-LXXNVGYKKMVL (X denotes inability to make an amino acid assignment) [SEQ ID No. 7]. Degenerate oligonucleotides corresponding either to sequence FYTKPPQXV [SEQ ID No. 5] or NVGYKKMVL [SEQ ID No. 5] were used to probe a M426 cDNA library. An initial screening of $10^6$ plaques yielded approximately 350 clones recognized by probes derived from both peptide segments. Restriction digestion of several plaque-purified phage DNAs revealed two classes of inserts. Selected cDNA inserts were analyzed by restriction endonuclease digestion. The nucleotide sequence of the FRP cDNAs was determined by the dideoxy chain-termination method. To search for homology between FRP and any known protein, we analyzed the GenBank, PDB, SwissProt and PIR protein sequence data bases. Alignments were generated with the program PileUp from the Wisconsin Package Version 8 (Genetics Computer Group; Madison Wis.). Mapping (FIG. 1B) and sequence analysis (FIG. 1C) of a representative from each class, designated HS1 and HS8, demonstrated that they were overlapping cDNAs. HS1 was ~2 kb in length and contained a 942-bp open reading frame; HS8 encoded a portion of the 942-bp open reading frame as well as approximately 0.3 kb of cDNA extending upstream of the ATG start codon. The putative start codon, located at position 303 in the HS1 sequence, was flanked by sequence that closely matched the proposed GCC(G/A)CCATGG [SEQ ID No. 8] consensus sequence for optimal initiation by eukaryotic ribosomes (Kozak, M. (1987) Nucleic Acids Res 15, 8125–48). An upstream in-frame stop codon was not present.

As expected for a secreted protein, a hydrophobic 26-amino acid segment at the NH2-terminus likely functions as a signal peptide. The experimentally determined protein sequence begins 11 residues downstream from the presumptive signal sequence, suggesting additional processing or incidental proteolysis. There was complete agreement between the predicted and observed amino acid sequences; the three undefined residues in the latter corresponded to Cys57, Cys67 and His68, residues which typically are undetectable or have low yields following Edman degradation. Two overlapping sequences in the COOH terminal region fulfill the criteria for a consensus binding site to a hyaluronic acid (Yang, B., Yang, B. L., Savani, R. C. & Turley, E. A. (1994) Embo J 13, 286–96) (FIG. 1C). Two potential asparagine-linked glycosylation sites are also present. A consensus polyadenylation signal was not identified in the cDNA sequence, raising the possibility that the cDNA clones from this oligo-dT primed library resulted from internal priming at an adenine-rich region.

Once a FRP cDNA was isolated, FRP genomic sequences were readily identified by methods that are well known in the art. Briefly, a human genomic DNA library (Stratagene) was screened by Southern blotting with two different human FRP cDNA probes: pF2 insert was used to identify genomic fragments containing any of the coding sequence; SalI-BstXI fragment (bp 417–781, according to numbering scheme for pF2) was used to identify genomic fragment(s) containing sequence encoding the cysteine-rich domain (CRD). Phage containing DNA that hybridized with FRP probes were plaque-purified, and portions of the genomic DNA inserts were then isolated and sequenced. A portion of the genomic sequence including the 5' flanking region is illustrated in FIG. 11 [SEQ ID No. 26].

Relationship to the FZ Protein Family

Search of several protein databases revealed significant homology of a portion of the predicted amino acid sequence to a specific region conserved among members of the FZ family (FIG. 2). The observed homology is confined to the extracellular CRD of FZ, a region consisting of ~110 amino acid residues that includes 10 cysteines and a small number of other invariant residues. This domain has special importance because it is a putative binding site for Wnt ligands (Bhanot, P., Brink, M., Samos, C. H., Hsieh, J. C., Wang, Y., Macke, J. P., Andrew, D., Nathans, J. & Nusse, R. (1996) Nature 382, 225–30). The FRP CRD is 30–42% identical to the CRD of the other FZ proteins.

In addition to the plasma membrane-anchored FZ proteins and FRP, three other molecules have been described which also possess a FZ CRD motif. An alternatively spliced isoform of mouse collagen XVIII was the first such protein to be reported (Rehn, M. & Pihlajaniemi, T. (1995) J Biol Chem 270, 4705–11). The two other molecules, mouse SDF5 (Shirozu, M., Tada, H., Tashiro, K., Nakamura, T., Lopez, N. D., Nazarea, M., Hamada, T., Sato, T., Nakano, T. & Honjo, T. (1996) Genomics 37, 273–280) and human FRZB (Hoang, B., Moos, M., Jr., Vukicevic, S. & Luyten, F. P. (1996) J Biol Chem 271, 26131–26137), resemble FRP in that each consists of ~300 amino acid residues, including a signal peptide, CRD near its NH2-terminus and a hydrophilic COOH-terminal moiety. FRP and SDF5 have 58% identities in their CRDs, while FRP and FRZB are only 32% identical in this region. Elsewhere, these molecules are only 15–20% identical. Thus, FRP, SDF5 and FRZB may constitute a subfamily of small, FZ-related proteins that lack the seven transmembrane motif responsible for anchoring FZ proteins to the plasma membrane and are presumably secreted.

FIGS. 1 and 2 and 8 provide illustrations of these protocols and results. FIG. 1 consists of a series of panels. Panel (B) shows a representation of human FRP cDNA clones. Overlapping clones HS1 and HS8 are shown above a diagram of the complete coding sequence and the adjacent 5' and 3' untranslated regions. The coding region is boxed; the open portion corresponds to the signal sequence. Untranslated regions are represented by a line. Selected restriction sites are indicated. Panel (C) shows the predicted FRP amino acid sequence (standard single-letter code) [SEQ ID No. 4]. The peptide sequence obtained from the purified protein is underlined. Double-underlined sequences were used to generate oligonucleotide probes for screening of the M426 cDNA library. The putative signal sequence is italicized. The large shaded region is the cysteine-rich domain homologous to CRD's in members of the FZ family. The small shaded region is the lysine-rich segment that fulfills the criteria for a consensus hyaluronic acid-binding sequence. The dashed underlining denotes two potential asparagine-linked glycosylation sites.

FIG. 8 shows the nucleic acid sequence which encodes a FRP polypeptide (8A, [SEQ ID No. 2, bases 1–1119]; 8B, [SEQ ID No. 2, bases 1120–2975]; 8C, [SEQ ID No. 27]). At ~nucleotide 340 we denote with an asterisk a site in the molecule where we observe an insert of the sequence "CAG" in some constructs. This would result in an insert of a single amino acid residue (alanine) in the putative signal peptide sequence without altering any of the remaining amino acid sequence. This may result from alternative splicing or possibly a sequencing artifact.

FIG. 2 provides comparisons of the CRDs of FRP and other members of the FZ family. Solid black shading highlights identities present in human FRP and any other FZ family member. The consensus sequence indicates residues present in at least eight of the sixteen FZ or FZ-related proteins. Double asterisks denote the ten invariant cysteine residues, single asterisks indicate other invariant residues. hFRP, human FZ SEQ. ID No. 9-related protein, hFZ (SEQ ID No. 10) (Zhao, Z., Lee, C., Baldini, A. & Caskey, C. T. (1995) Genomics 27, 370–3); hFZ (SEQ ID NO:11) 5 (Wang, Y., Macke, J. P., Abella, B. S., Andreasson, K., Worley, P., Gilbert, D. J., Copeland, N. G., Jenkins, N. A. & Nathans, J. (1996) J Biol Chem 271, 4468–76); mFZ3[SEQ ID No. 12–16]-mFZ8 (Wang, Y., Macke, J. P., Abella, B. S., Andreasson, K., Worley, P., Gilbert, D. J., Copeland N. G., Jenkins, N. A. & Nathans, J. (1996) J Biol Chem 271, 4468–76); rFZ1 [SEQ ID No. 17] and rFZ2 [SEQ ID NO:18] (Chan, S. D., Karpf, D. B, Fowlkes, M. E., Hooks, M., Bradley, M. S., Vuoung, V., Bambino, T., Liu, M. Y., Arnaud, C. D., Strewler, G. J. & et al. (1992) J Biol Chem, 267, 25202–7), dFZ [SEQ ID No. 19] (Vinson, C. R, Conover, S. & Adler, P. N. (1989) Nature 338, 263–4); dFZ2 [SEQ ID No. 20], (Bhanot, P., Brink, M., Samos, C. H., Hsieh, J. C., Wang, Y., Macke, J. P., Andrew, D., Nathans, J. & Nusse, R. (1996) Nature 382, 225–30); cFZ [SEQ ID No. 21] (Wang, Y., Macke, J. P., Abella, B. S., Andreasson, K., Worley, P., Gilbert, D. J., Copeland, N. G., Jenkins, N. A. & Nathans, J. (1996) J Biol Chem 271, 4468–76); mCOL, mouse collagen XVIII [SEQ ID No. 22] (Rehn, M. & Pihlajaniemi, T. (1995) J Biol Chem 270, 4705–11); hFRZB [SEQ ID No. 23], (Hoang, T. B., Moos, M., Jr., Vukicevic, S. & Luyten, F. P. (1996) J Biol Chem 271, 26131 7); mSDF5 [SEQ ID No. 24] (Shirozu, M., Tada, H., Tashiro, K., Nakamura, T., Lopez, N. D., Nazarea, M., Hamada, T., Sato, T., Nakano, T. & Honjo, T. (1996) Genomics 37, 273–280).

Example 3

Expression of the FRP Gene

Northern and Southern Blot Analysis

RNA from cell lines was isolated, transferred to nitrocellulose filters, and hybridized with labeled probes as previously described (Finch, P. W., Rubin, J. S., Miki, T., Ron, D. & Aaronson, S. A. (1989) Science 245, 752 5). Northern blots containing approximately 2 μg of poly A+RNA isolated from a variety of different organs were purchased from Clontech (Palo Alto, Calif.). Labeled probes were hybridized in Express Hyb hybridization solution (Clontech) according to the manufacturer's protocol. The FRP NotI-SmaI cDNA fragment and human β-actin cDNA probe provided by Clontech were $^{32}$P-labeled with random hexamers and used at a concentration of $1–2\times10^6$ cpm/ml (specific activity $>8\times10^8$ cpm/μg DNA).

Southern blotting was performed as previously described (Kelley, M. J., Pech, M., Seuanez, H. N., Rubin, J. S., O'Brien, S. J. & Aaronson, S. A. (1992) Proc Natl Acad Sci U S A 89, 9287–91), except for variation in formamide concentration during hybridization, as noted in the text. FRP cDNA probes were $^{32}$P-labeled with the nick-translation kit from Amersham.

FRP Gene is Expressed in Multiple Organs and Cell Types

Using the 1081-bp NotI-SmaI fragment of HS1 (FIG. 1B) as probe, a single 4.4 kb transcript was detected in polyA+ RNA from several human organs (FIG. 3). In adult tissues, the highest level of expression was observed in heart, followed by kidney, ovary, prostate, testis, small intestine and colon. Lower levels were seen in placenta, spleen and brain, while transcript was barely detectable in skeletal muscle and pancreas. No hybridization signal was evident in mRNA from lung, liver, thymus or peripheral blood leukocytes. In poly A+RNA from a small sample of human fetal organs, the 4.4 kb transcript was highly represented in kidney, at moderate levels in brain, barely detectable in lung, and undetectable in liver.

Northern analysis of total RNA from various human cell lines demonstrated the 4.4 kb transcript and, occasionally, additional faint bands not further analyzed (FIG. 3, extreme right panel). While the transcript was detected in RNA from embryonic lung (M426 and WI-38) and neonatal foreskin (AB1523) fibroblasts, it was not observed in a sample of adult dermal fibroblasts (501T). In addition to fibroblasts, the transcript was seen in RNA from primary keratinocytes, indicating that expression was not limited to cells of mesenchymal origin. Considering that the cumulative size of the initial overlapping FRP cDNAs was only 2.8 kb, detection of a 4.4 kb transcript reinforced the suggestion that the cDNAs were generated by internal priming at adenine-rich regions. An illustration of the sequence of this larger transcript is provided in FIG. 8 (SEQ ID No. 27).

Developmental Expression of FRP

Northern blot analysis of samples from human organs indicates that the FRP transcript was expressed at many sites, and the level of expression varied in embryonic and adult tissues. Finch, et al., P.N.A.S. 94: 6770–6775 (1997). To assess its pattern of expression and potential role in development, we investigated the distribution of FRP transcript in mouse embryos by in situ hybridization analysis. A 144-bp mouse FRP cDNA fragment was generated by RT-PCR, using total RNA from NIH3T3 fibroblasts as template. After subcloning into pGEM3Zf(-), $^{35}$S-labeled sense and antisense riboprobes were prepared for hybridization. These experiments suggest that FRP transcript is present in embryos from 8.5 days to birth, with highest overall levels of expression observed at 12.5–14.5 days. At this peak period, expression was documented in discrete portions of the central nervous system, gastrointestinal tract, genitourinary system, lining of the abdominal cavity, heart and developing vertebrae. Transcript was present either in mesenchymal or epithelial cells, depending on the location. The transient aspect of FRP spatiotemporal distribution reinforced the idea that its expression is regulated during development. Like the Wnt proteins, FRP participates in processes that govern embryonic development.

Detection of FRP in Other Species

Figure 5:
FIG. 5 shows a southern blot analysis of FRP genomic sequences in different species.

To determine whether the FRP gene was present in other species, genomic DNAs from various sources were fully digested with EcoRI and hybridized with an NcoI-SmaI cDNA fragment (FIG. 1B) under varying conditions of stringency (FIG. 5). Multiple bands were observed under highly stringent conditions (50% formamide) in DNA from human, rhesus monkey, mouse and chicken. With moderate stringency (35% formamide), no additional fragments were seen in the DNA from these species but fragments were detected in Xenopus DNA. No hybridization signal was observed with DNA from Drosophila or yeast (S. cervisiae) in these experiments. At low stringency (20% formamide), the background was too high to detect specific signals. These results strongly suggested that the FRP gene is highly conserved among vertebrates. Although these experiments did not detect an FRP homolog in the invertebrates, the existence of such homologs was not rigorously excluded, due to the limitations of the method.

Southern blotting performed either with the NotI-NcoI cDNA fragment (FIG. 1B) or with synthetic oligonucleotide probes corresponding to different portions of the FRP coding sequence, hybridized to subsets of genomic fragments detected with the NcoI-SmaI probe. This finding and the lack of additional bands detected only under relaxed conditions (FIG. 5) indicated that highly related FRP-like sequences are not present in the human genome. Thus, the multiple genomic fragments hybridizing to the FRP cDNA in Southern blots are likely to reflect the presence of several exons in the hFRP gene.

FIGS. 3 and 5 provide an illustration of these protocols and results. FIG. 3 shows FRP mRNA expression in normal human adult and embryonic tissues, and in cultured cells. Blots containing approximately 2 μg of poly A+RNA from each of the indicated tissues or 10 μg of total RNA from different human cell lines were probed with radiolabeled FRP and β-actin cDNA fragments, as described in the Methods. The position of DNA size markers, expressed in kb, is indicated at the left of the tissue blots; the position of 28S and 18S ribosomal RNA is shown at the left of the cell blot.

FIG. 5 shows a southern blot analysis of FRP genomic sequences in different species. After fractionation by agarose gel electrophoresis and transfer to filters, Eco-RI-digested genomic DNAs were hybridized in the presence of either 50% or 35% formamide. Specimens were from the following species: λ, lambda phage; H, human; $M^k$, rhesus monkey; $M^o$, mouse; C, chicken; X, *Xenopus laevis*; D, *Drosophila melanogaster*; Y, yeast (*S. cerevisiae*).

Example 4
Chromosomal Localization of FRP

A 4.1 kb FRP genomic fragment obtained from a human fibroblast genomic DNA library (Stratagene) was labeled with biotin or digoxigenin and used as a probe for in situ hybridization to locate the FRP gene in chromosomal preparations of methotrexate-synchronized normal peripheral human lymphocyte cultures. The conditions for hybridization, detection of fluorescent signal, digital-image acquisition, processing and analysis were as previously described (Zimonjic, D. B., Popescu, N. C., Matsui, T., Ito, M. & Chihara, K. (1994) Cytogenet Cell Genet 65, 184–5). The identity of the chromosomes with specific signal was confirmed by rehybridization using a chromosome 8-specific probe, and the signal was localized on G-banded chromosomes.

Figure 4:
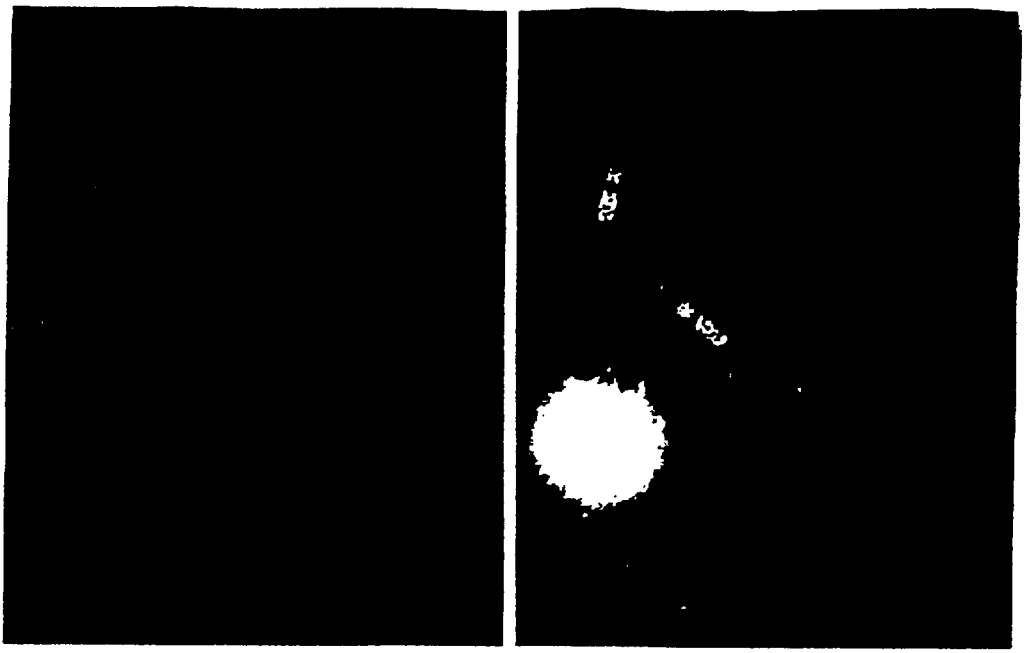
FIG. 4 shows the chromosomal localization of the FRP gene by fluorescent in situ hybridization.

Using a fluorescent-labeled 4.1 kb genomic fragment containing a portion of the FRP coding sequence, in situ hybridization revealed a single locus at chromosome 8p11.1–12 (FIG. 4). This site may be near the putative locus of the hFZ3 gene, based on homology with the location of mFz3 in the mouse genome (Wang, Y., Macke, J. P., Abella, B. S., Andreasson, K., Worley, P., Gilbert, D. J., Copeland, N. G., Jenkins, N. A. & Nathans, J. (1996) J Biol Chem 271, 4468–76). Radiation hybrid analysis yielded results consistent with the fluorescent in situ hybridization analysis. Significantly, the chromosomal locus of the FRP gene is compatible with that of a tumor suppressor gene associated prostate, colon, and non small cell lung carcinoma. Information on FRP genomic structure and its relationship to defects in these malignancies is a material avenue of research in this field.

FIG. 4 provides an illustration of these protocols and results. FIG. 4 shows the chromosomal localization of the FRP gene by fluorescent in situ hybridization. To localize the FRP gene, one hundred sets of metaphase chromosomes were analyzed. In eighty metaphases, a double fluorescent signal was observed with the FRP genomic problem in 8p11.2–12 on both chromosome homologs (left panel). The identity of the chromosomes was confirmed by hybridization with a probe specific for chromosomes 8 (right panel).

Example 5
Biosynthetic Studies of FRP

For biosynthetic studies, M426 cells grown in T-25 flasks were incubated for 30 min. in methionine-free DMEM in the presence or absence of 50 μg/ml heparin (bovine lung, Sigma; when present, heparin was included in all subsequent media), which was subsequently replaced with medium containing $^{35}$S-methionine (1 mCi/5 ml per dish). After 30 min., the radioactive medium was removed, and monolayers washed with medium containing unlabeled methionine, then incubated for varying intervals in fresh nonradioactive medium. At the specified times, the conditioned media and cell lysates were collected and processed as previously described (Rubin, J. S., Chan, A. M., Bottaro, D. P., Burgess, W. H. Taylor, W. G., Cech, A. C., Hirshfield, D. W., Wong, J., Miki, T., Finch, P. W. & et al. (1991) Proc Natl Acad Sci U S A 88, 415–9). Immunoprecipitations were performed with a rabbit polyclonal antiserum (100 μg/ml) raised against a synthetic peptide corresponding to FRP amino acid residues 41–54, in the presence or absence of competing peptide (50 μg/ml). Immune complexes adsorbed to GammaBind (Pharmacia) were pelleted by centrifugation and washed; labeled proteins were resolved by SDS/PAGE and detected by autoradiography.

Figure 6:
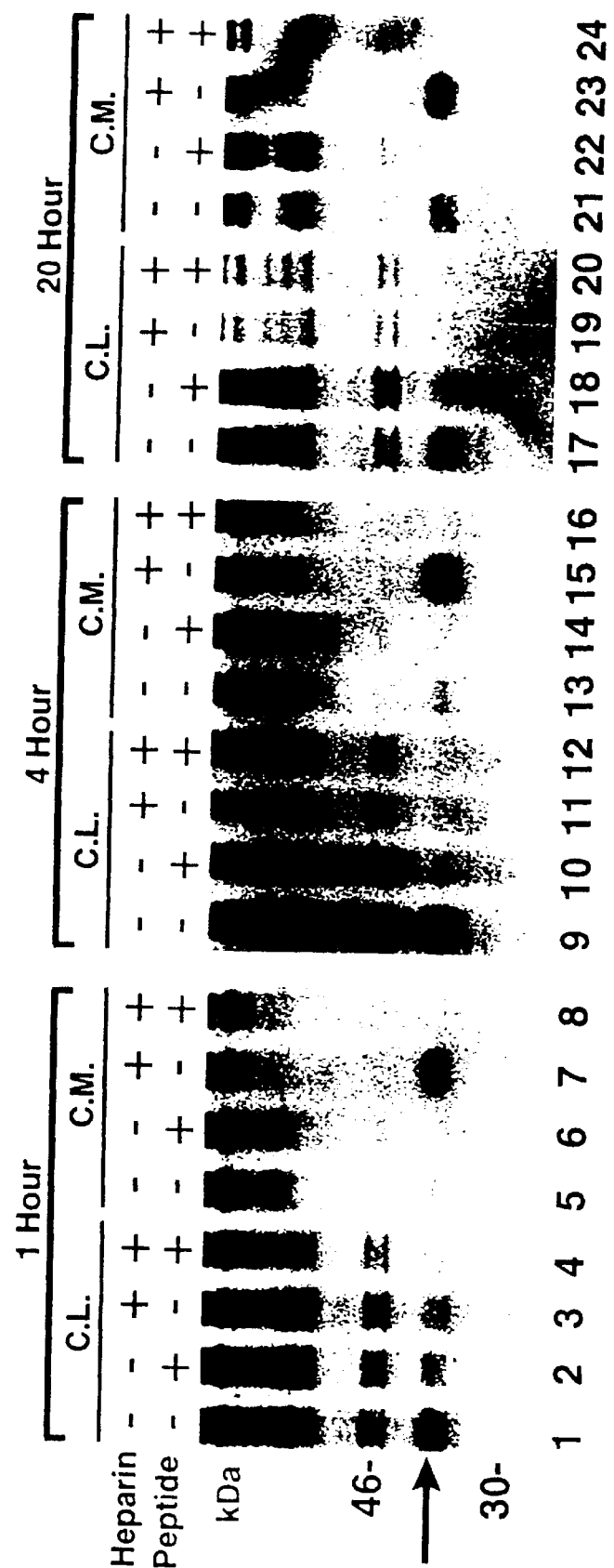
FIG. 6 shows the biosynthesis of FRP in M426 cells via a pulse-chase experiment performed with metabolically labeled cells incubated either in the absence or presence of heparin.

FIG. 6 provides an illustration of these results. FIG. 6 shows the biosynthesis of FRP in M426 cells. A pulse-chase experiment was performed with metabolically labeled cells incubated either in the absence or presence of heparin. Proteins were immunoprecipitated from cell lysates (C.L.) or conditioned medium (C.M.) with FRP peptide antiserum in the absence or presence of competing peptide, and resolved in a 10% polyacrylamide SDS gel. Cells and media were harvested 1, 4 or 20 hours after a 30 min labeling period. Lanes 1–24 are labeled at the bottom. The protein band corresponding to FRP is indicated by an arrow. The position of molecular mass markers is shown at the left.

FRP is Secreted, but Primarily Cell-Associated in the Absence of Exogenous Heparin To study the synthesis and processing of FRP protein, a pulse-chase experiment was performed with $^{35}$S-methionine labeled M426 cells either in the absence or presence of added heparin. As shown in FIG. 6, a 36 kDa protein band was specifically immunoprecipitated with antiserum raised against a synthetic peptide corresponding to a portion of the FRP NH2-terminal sequence. In the absence of soluble heparin, after either 1 hour (lanes 1 and 5) or 4 hours (lanes 9 and 13) FRP was much more abundant in the cell lysate than in the conditioned medium. However, after 20 hours, the amount of FRP protein in the medium (lane 21) was comparable to that which remained cell-associated (lane 17). At this last time point, the combined band intensity in the two compartments had decreased relative to that observed earlier, suggesting significant protein turnover during the experiment. Moreover, after 20 hr the FRP-specific signal appeared as a doublet, providing additional evidence of proteolysis. In the presence of soluble heparin (50 μg/ml), most of the FRP was detected in the medium at all three time points (compare lanes 3 and 7, 11 and 15, 19 and 23). Heparin also appeared to stabilize FRP, as the band intensity was stronger when heparin was present, and there was no evidence of partial proteolysis. Interestingly, others have shown that heparin can release Wnt-1 from the cell surface in a similar manner (Papkoff, J. & Schryver, B. (1990) *Mol Cell Biol* 10, 2723–30; Bradley, R. S. & Brown, A. M. (1990) *Embo J* 9, 1569–75; Reichsman, F., Smith, L. & Cumberledge, S. (1996) *J Cell Biol* 135, 819–27). Taken together, our results demonstrate that FRP is secreted, although it tends to remain cell-associated and relatively susceptible to degradation unless released into the medium by soluble heparin.

FRP Binds to Hyaluronic Acid

Figure 9:
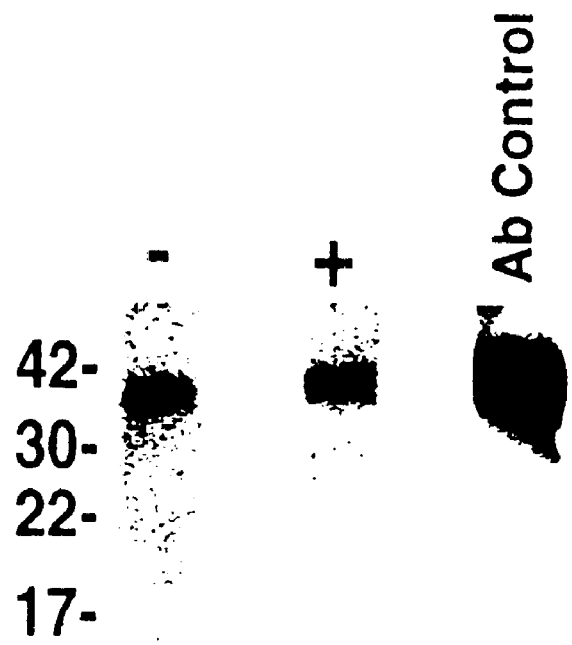
FIG. 9 shows the binding of FRP to biotinylated hyaluronic acid in a transblot assay under either nonreducing (−) or reducing (+) conditions.
Figure 10:
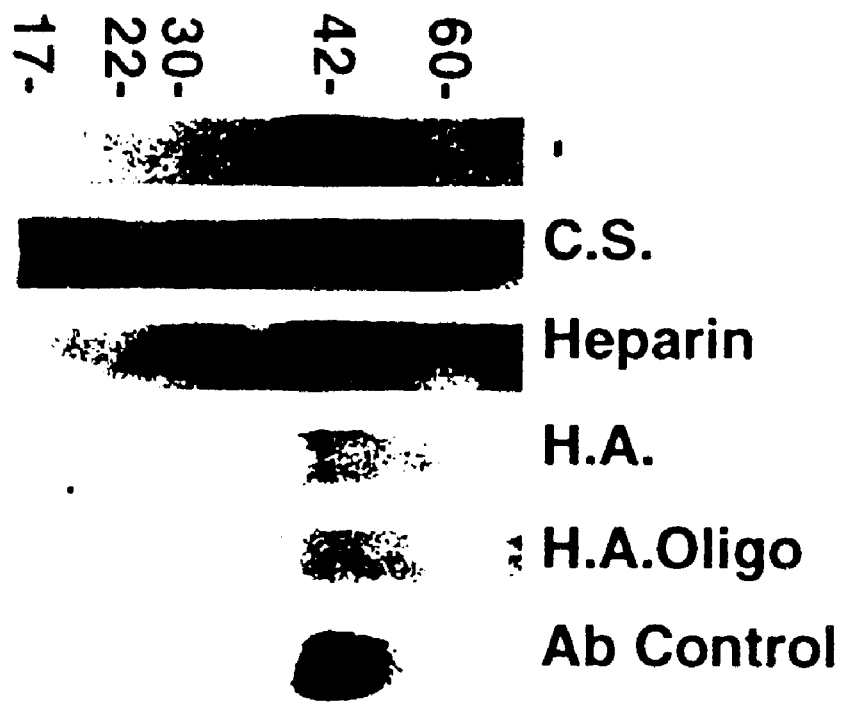
FIG. 10 shows the competition of BHA binding to FRP by various proteoglycans, C.S. is chondroitin sulfate, H.A. is hyaluronic acid, H.A. oligo is hyaluronic acid oligosaccaride. The Ab control consists of a western blot of FRP with rabbit polyclonal antiserum raised against FRP synthetic peptide.

As shown by the amino acid sequence in FIG. 1C, FRP contains a lysine-rich segment that fulfills the criteria for a consensus hyaluronic acid-binding sequence (Yang, B., Yang, B. L., Savani, R. C. & Turley, E. A. (1994) Embo J 13, 286–96). FIG. 9 shows the binding of FRP to biotinylated hyaluronic acid in a transblot assay under either nonreducing (−) or reducing (+) conditions (Yang, B, Zhang, L., and Turley, E. A. (1993) J. Bio. Chem. 268, 8617–8623; Hardwick, C., Hoare, K., Owens, R. Hohn, H. P., Hook, M., D., Cripps and Turley, E. A. (1992) J. Cell Biol. 117, 1343–1350). Further, FIG. 10 shows the competition of BHA binding to FRP by various proteoglycans, C.S. is chondroitin sulfate, H.A. is hyaluronic acid, H.A. oligo is hyaluronic acid oligosaccharide. The Ab control consists of a western blot of FRP with rabbit polyclonal antiserum raised against FRP synthetic peptide.

FIGS. 9 and 10 provide an illustration of these results. FIG. 9 shows the binding of FRP to biotinylated hyaluronic acid in a transblot assay under either nonreducing (−) or reducing (+)conditions. FIG. 10 shows the competition of BHA binding to FRP by various proteoglycans, C.S. is chondroitin sulfate, H.A. is hyaluronic acid, H.A. oligo is hyaluronic acid oligosaccharide. The Ab control consists of a western blot of FRP with rabbit polyclonal antiserum raised against FRP synthetic peptide.

Example 6
Modulation of Xenopus Development by FRP

Wnt-1, wg, Xwnt-3a and Xwnt-8 plasmids were used as described (McMahon, A. P. & Moon, R. T. (1989) *Development* 107 Suppl, 161–7; Chakrabarti, A., Matthews, G., Colman, A. & Dale, L. (1992) *Development* 115, 355–69; Wolda, S. L., Moody, C. J. & Moon, R. T. (1993) *Dev Biol* 155, 46–57; Smith, W. C. & Harland, R. M. (1991) *Cell* 67, 753–65). The FRP NaeI-SalI cDNA fragment, which includes the full coding sequence, was subcloned into the StuI and XhoI sites of pCS2+ (Turner, D. L. & Weintraub, H. (1994) *Genes Dev* 8, 1434–47). All mRNAs for injection were synthesized as capped transcripts in vitro with SP6 RNA polymerase (Ambion Megascript Kit). Embryo preparation and staging were performed as described (He, X., Saint-Jeannet, J. P., Woodgett, J. R., Varmus, H. E. & Dawid, I. B. (1995) *Nature* 374, 617–22). Transcripts were injected into the two blastomeres near the equatorial midline region at the 4-cell stage.

FRP Antagonizes Wnt Action in Xenopus Embryo Assay

Because FRP possesses a potential binding site for Wnt molecules and appears to partition among cellular compartments like Wnt-1, it seemed possible that FRP might modulate the signaling activity of Wnt proteins. We envisioned two alternatives: FRP might antagonize Wnt function by binding the protein and blocking access to its cell surface signaling receptor, or FRP might enhance Wnt activity by facilitating the presentation of ligand to the FZ receptors, analogous to the action of soluble interleukin 6 receptors (Kishimoto, T., Taga, T. & Akira, S. (1994) *Cell* 76, 253–62).

To test these possibilities, we examined the effect of FRP on Wnt-dependent dorsal axis duplication during Xenopus embryogenesis. Previous studies have demonstrated that microinjection of mRNA encoding certain Wnt molecules, such as mouse Wnt-1, Wg, XWnt-8 or XWnt-3a, into early Xenopus embryos can induce the formation of an ectopic Spemann organizer and, subsequently, duplication of the dorsal axis (McMahon, A. P. & Moon, R. T. (1989) *Development* 107 Suppl, 161–7; Chakrabarti, A., Matthews, G., Colman, A. & Dale, L. (1992) *Development* 115, 355–69; Wolda, S. L., Moody, C. J. & Moon, R. T. (1993) *Dev Biol* 155, 46–57; Smith, W. C. & Harland, R. M. (1991) *Cell* 67, 753–65; Moon, R. T., Christian, J. L., Campbell, R. M., McGrew, L., DeMarais, A., Torres, M., Lai, C. J., Olson, D. J. & Kelly, G. M. (1993) *Dev Suppl*, 85–94; Sokol, S., Christian, J. L., Moon, R. T. & Melton, D. A. (1991) *Cell* 67, 741–52). In addition, it has been reported that FRZB is a secreted antagonist of Wnt signaling expressed in the Spemann organizer (Leyns, L., Bouwmeester, T., Kim, S. H., Piccolo, S. & De Robertis, E. M. (1997) *Cell* 88, 747–756; Wang, S., Krinks, M., Lin, K., Luyten, F. P. & Moos, M. J. (1997) *Cell* 88, 757–766).

Figure 7:
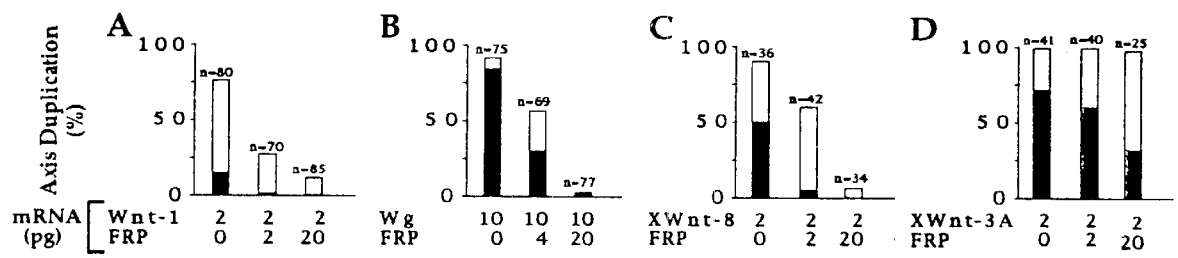
FIG. 7 shows the dorsal axis duplication in Xenopus embryos in response to varying combinations of Wnt and FRP transcripts FIGS. 8A[SEQ ID No. 2, bases 1–1119], 8B [SEQ ID No. 2, bases 1150–2108] and 8C [SEQ ID No. 1] show nucleic acid sequences which encode FRP.

FIG. 7 provides an illustration of these results. FIG. 7 shows the dorsal axis duplication in Xenopus embryos in response to varying combinations of Wnt and FRP transcripts. The total number of embryos injected in two to four independent experiments is indicated by the value of n; each bar represents the percentage of axis duplication; the solid portion within each bar represents the percentage of extensive duplication, which is defined by the presence of the cement gland and at least one eye in the duplicated axis. The amount of mRNA injected per embryo is shown below the bars.

As illustrated in FIG. 7, injection of suboptimal doses of Wnt-1, Wg, or XWnt-8 mRNA into embryos induced partial or complete duplication in at least 75% of the animals. Suboptimal doses were used to enable the detection of enhancement of the axis duplication phenotype, if the role of FRP was to facilitate Wnt signaling. However, when similar quantities of FRP and Wnt RNA were coinjected, the incidence and extent of axial duplication were significantly reduced (FIG. 7). The effect was dose-dependent, as the number of animals with an abnormal phenotype was even lower when the relative amount of FRP RNA was increased five- to ten-fold. Injection of FRP RNA alone at a higher dose (100 μg) into the dorsal side of the embryo did not affect the endogenous dorsal axis formation.

Surprisingly, FRP was much less effective in antagonizing XWnt-3a, suggesting a degree of specificity regarding interactions with different members of the Wnt family. The Wnt signaling pathway is thought to proceed through suppression of the activity of glycogen synthase kinase-3, a cytoplasmic serine-threonine kinase (Miller, J. R. & Moon, R. T. (1996) *Genes Dev* 10, 2527–39). Axis duplication induced by a dominant-negative, kinase-inactive mutant of glycogen synthase kinase-3β (He, X., Saint-Jeannet, J. P., Woodgett, J. R., Varmus, H. E. & Dawid, I. B. (1995) *Nature* 374, 617–22; Dominguez, I., Itoh, K. & Sokol, S. Y. (1995) *Proc Natl Acad Sci U S A* 92, 8498–502; Pierce, S. B. & Kimelman, D. (1995) *Development* 121, 755–65) was not affected by FRP, consistent with the assumption that FRP directly interferes with Wnt signaling at the cell surface, not by indirectly interfering with a late step in the Wnt signaling pathway.

Example 7
Expression and Purification of Recombinant FRP

As disclosed in detail below, recombinant FRP has been produced in a stable mammalian expression system involving Madin-Darby canine kidney (MDCK) cells. One of the advantages of eukaryotic expression is the reliability of disulfide bond formation and associated protein folding, which are likely to be important in the synthesis of the secreted cysteine-rich FRP protein. In contrast, preliminary experiments with prokaryotic expression yielded protein that appeared to be heterogeneous with respect to the folding of disulfide bonds. MDCK cells were transfected by standard calcium phosphate precipitation methodology with a pcDNA vector (Invitrogen) containing the FRP coding sequence. Following G418 selection of transfected cells, immunoblot analysis of conditioned medium from a mass culture revealed the presence of recombinant FRP-crossreactive protein. The amount of FRP in the medium from FRP-transfected MDCK cells appeared to be far greater than quantities produced by cell lines naturally expressing FRP.

As discussed in detail below, the MDCK/FRP culture was expanded into T-175 flasks and a series of pilot experiments conducted to develop a scheme for the purification of recombinant protein. Once the cells reached confluence, serum-containing growth medium was removed, the monolayer was washed twice with phosphate-buffered saline, and then serum-free medium was added. After 72 hours, the culture fluid was harvested and serum-containing medium was added to the flasks. Subsequently, the monolayer was again washed and serum-free medium introduced for another 72 hour period of conditioning. This process was repeated four or five times with the same monolayer cultures. The conditioned medium was promptly concentrated by ultrafiltration at 4° C. in a stirred chamber with a 10-kDa molecular mass cutoff (Amicon). Immunoblot analysis confirmed that FRP protein was present in the retentate, and its concentration was markedly increased compared to that of the starting material. The retentate was fractionated by heparin-TSK high performance liquid chromatography (HPLC).

FIG. 12 provides an illustration of these results. FIG. 12 shows recombinant FRP. (A) Preparation of FRP protein. The FRP coding sequence was subcloned into pcDNA3.1(+) and transfected into MDCK cells by standard calcium phosphate precipitation methodology. Following selection, transfected cells were grown to confluence and switched to serum-free medium. After 72 hours, conditioned medium was collected, concentrated by ultrafiltration and fractionated by heparin-TSK HPLC. At least 90% of the protein did not bind to resin equilibrated in 0.05M phosphate/0.15M NaCl/pH 7.4. After eluting the less tightly bound protein with 0.5M NaCl (data not shown), a modified linear gradient of increasing [NaCl] was used to recover the remaining protein. (B) Immunoblotting with FRP peptide antiserum. Ten $\mu$l aliquots of selected 1 min fractions from heparin-TSK chromatography (indicated by bar in panel A) were resolved by 12% SDS-PAGE, transferred to Immobilon filters, blotted with FRP amino-terminal peptide antiserum (Finch, et al., P.N.A.S. 94: 6770–6775 (1997)) and analyzed by chemiluminescence. Position of molecular mass markers (kDa) is shown at left. (C) Silver-staining of FRP-containing fractions from heparin-TSK chromatography. Five $\mu$l aliquots of indicated fractions were subjected to 12% SDS-PAGE and silver-stained (BioRad kit). Position of molecular mass markers (kDa) is shown at left.

Most protein did not bind to the resin, which had been equilibrated at neutral pH in isotonic buffer. Following a stepwise increase of NaCl concentration to 0.5M, the remaining protein was eluted with a modified linear gradient of increasing [NaCl] (FIG. 12A). FRP was detected by western blotting of aliquots from the major, overlapping protein peaks which eluted with 1.1–1.4M NaCl (FIG. 12B). Silver-staining of proteins resolved by SDS-PAGE demonstrated that the peak fractions only contained bands corresponding in size to immunoreactive FRP (FIG. 12C). Based on optical density, the estimated yield of FRP protein was 0.5–1.0 mg from two liters of conditioned medium (~50–100 times more than the original, naturally occurring source).

Detailed Recombinant FRP Recombinant Expression Protocols

Vectors and constructs included pcDNA3.1(+) with both the full-length human FRP coding sequence as well as site directed mutants of full-length FRP, in which substitutions (Asn to Gln) were made at either or both of the Asn-linked glycosylation sites. Additional vectors included pcDNA3.1 (-)/Myc-His C designed to link Myc and His tags to the carboxy-terminus of recombinant protein of the full-length human FRP coding sequence as well as three truncated FRP derivatives, each lacking a varying amount of the carboxy-terminal portion of the full-length protein; sequences span: 1–171, 1–221, and 1–242.

Constructs were transfected into MDCK cells by standard calcium phosphate methodology, and cultures were subjected to selection with antibiotic (G418, 0.5 mg/ml). Transfected mass culture was expanded, ultimately grown in the absence of G418 (growth medium is DMEM plus 10% fetal bovine serum). Clonal lines were isolated from the mass culture of FRP/MDCK transfectants and screened for elevated FRP expression by immunoblot analysis of culture fluid.

To generate conditioned medium, cells were grown to confluence in T175 flasks (alternatives known in the art also should be suitable, such as cell factories or microcarriers in bioreactors). Medium in these experiments was switched from DMEM plus 10% fetal bovine serum to serum-free DMEM. After 2 or 3 days, conditioned medium was harvested and optionally another round of serum-free DMEM was added, to be harvested, typically after another 3 days. As many as 10 collections could be made from a single monolayer. In some instances, cells were cycled from serum-free to serum containing medium, before switching back to serum-free medium for subsequent collection of conditioned medium Medium was filtered through a 0.45 micron membrane prior to concentration by ultrafiltration. Optionally medium was clarified by centrifugation before filtration. For ultrafiltration, conditioned medium was concentrated in a stainless steel, Amicon model 2000 stirred cell with a YM-10 membrane (10 kD molecular mass cutoff) at 4° C. Typically volumes of 1–2 liters were reduced to 45–90 ml. Concentrates were snap-frozen and stored in freezer.

Purification of FRP

As discussed above, wild type FRP was purified with heparin affinity chromatography. Details of chromatography varied, from linear NaCl gradient with heparin-HPLC column to stepwise NaCl elution with Pharmacia Hi-Trap heparin column. FRP elutes with approximately 1.0 M NaCl.

FRP derivatives containing a Myc-His tag were purified with nickel resin (such as a Pharmacia Hi-Trap His column), typically being eluted with 50 or 100 mM imidazole solution. FRP-containing fractions were identified by immunoblotting and silver stain analysis following SDS-PAGE (12% polyacrylamide). Fractions were snap-frozen and stored in freezer.

Example 8

FRP and FRP Binding Partner Interaction Assays

A substantial body of data strongly suggests that Frizzled molecules function as receptors or components of receptors for Wnt proteins. (See e.g., He, et al., Science 275:1652–1654 (1997).) Deletional analysis indicated that the cysteine-rich domain (CRD) is responsible for conferring Wnt-binding or Wnt-dependent signaling to biological systems. Bhanot, et al., Nature 382:225–230 (1996). Because FRP contains a FZ-type CRD and is able to antagonize Wnt-dependent duplication of the dorsal axis in the Xenopus embryo assay (Finch, et al., P.N.A.S. 94:6770–6775 (1997), FRP is likely to be a receptor for a subset of Wnt family members. To test the hypothesis that FRP inhibits Wnt activity by binding Wnt proteins, the assays to elucidate the interaction of FRP with FRP binding proteins were designed.

Experimental systems to study Wnt binding and other interactions are problematic for a number of reasons. For years, Wnt receptor analysis has been hampered by the insolubility of Wnt proteins, which tend to remain associated with cell surfaces or extracellular matrix. Bradley, et al., EMBO J. 9:1569–1575 (1990). This property has impeded efforts to purify Wnts for tracer labeling and specific, sensitive receptor-ligand binding studies. Moreover, because vertebrates produce at least eight different Frizzleds Wang, et al., J. Biol. Chem. 271:4468–4476 (1996), six secreted Frizzled-related proteins (see e.g., Salic, et al., Development 124:4739–4748 (1997) and fifteen Wnts (Cadigan, et al., Genes Dev. 11:3286–3305 (1997), any cell is likely to endogenously express one or more molecules that could influence Wnt-Frizzled-binding [not to mention proteoglycans, which also affect Wnt binding and activity. (See e.g., Häcker, et al., Development 124:3565–3573 (1997).] This would undoubtedly complicate the interpretation of experiments involving ectopic expression of any component of the putative Wnt-FZ binding complex.

As an alternative, cell-free systems to study the binding of FRP and Wnts were developed. These systems have the advantage of simplicity, as the profile of endogenous Frizzled/FRP/Wnt expression would not be an issue. Moreover, experiments now can be performed with purified recombinant FRP. One model system disclosed in detail below makes use of an ELISA type of format. Microtiter wells are first coated with purified FRP, and then blocked with a large excess of bovine serum albumin (BSA). To minimize the problems associated with solubilizing Wnts, initial studies focused on studying FRP binding to Wingless (Wg) because an expression system is available that releases Wg into conditioned medium. Van Leeuwen, et al., Nature 368:342–344 (1994). Although expression of a heat shock-Wg construct in transfected S2 insect cells results in only a small fraction of recombinant Wg in the media, it is sufficient for binding studies and obviates the need for detergents or other agents to extract the protein from cell surfaces or extracellular matrix. Medium from the heat shock-Wg cells or S2 vector controls is incubated in microtiter wells that have either been coated with FRP and blocked with BSA or only blocked with BSA. After washing, the wells are sequentially incubated with antibody to Wg, secondary antiserum (against the Wg antibody) conjugated to alkaline phosphatase, and p-nitrophenol phosphate. The last reagent is a substrate for the phosphatase; the development of yellow color is a measure of the Wg protein retained in the wells.

FIG. 13 provides an illustration of these results. FIG. 13 illustrates the binding of FRP and Wg. (A) FRP-Wg interaction in ELISA format. Falcon 96-well microtiter plates were coated with recombinant human FRP at 100 ng/well (FRP 100) or left blank (FRP 0) prior to blocking with 4% bovine serum albumin. Subsequently wells were incubated with serial dilutions of conditioned medium from S2 cells expressing Wg via a heat shock promoter (Wg) or medium from control S2 cells (S2). Following washing, wells were incubated sequentially with a rabbit polyclonal antiserum against Wg, goat anti-rabbit antiserum conjugated to alkaline phosphatase, and p-nitrophenol phosphate. Color development, monitored at 405 nm, was indicative of Wg binding in the well. Each data point is the mean ±standard deviation of triplicate measurements; when not shown, deviation was smaller than size of symbol. (B) Immunoblotting of Wg. Samples of conditioned medium used in (A) were concentrated in Centricon-10 devices, resolved by 8% SDS-PAGE, transferred to Immobilon filters, blotted with Wg monoclonal antibody and analyzed by chemiluminescence. The arrow indicates band corresponding to Wg. Position of molecular mass markers is shown at left.

As shown in FIG. 13A, wells coated with 100 ng of FRP display specific and highly reproducible binding of Wg that varies with the dilution of conditioned medium. A small amount of non-specific binding is observed when relatively concentrated Wg-containing samples are incubated in wells that have not been coated with FRP. No background signal is seen in wells coated with FRP and incubated with medium from control S2 cells. This is consistent with the fact that control cells do not express detectable levels of Wg protein (FIG. 13B). Taken together, these data provide strong evidence that FRP is capable of binding Wg. These assays are described in detail below.

FRP-Wingless Standard ELISA Assay

Wells of ELISA plate were coated with purified, recombinant FRP. After blocking with BSA, conditioned medium containing Wingless (Wg) was introduced. Following appropriate incubation period, Wg-containing medium was removed and bound Wg was detected by sequential addition of antibody to Wg, secondary antibody conjugated to alkaline phosphatase and p-nitrophenylphosphate. Amount of yellow color in well, determined by ELISA reader (spectrophotometer measuring absorbance at 405 nm), was a measure of bound Wg. Either the amount of FRP used to coat wells or the dilution of Wg medium (or control medium) could be varied to generate additional quantitative information about the interaction between FRP and Wg.

FRP coating of the wells was accomplished by diluting FRP in 0.02% sodium azide/PBS, and add 50 ul to each well. 100–300 ng FRP/well provides optimal results. The plate was then incubated at 37° C. for 2 hours in a moist environment. In this assay, FRP was not added to the first lane, which serves as a blank. Blocking was accomplished by removing the FRP solution from the wells and adding 100 ul of a 4% BSA in sodium azide/PBS (no need to wash) and incubating at 37° C. for 2 hours. Washing was accomplished by washing the wells 5 times with TAPS (0.05% Tween 20 and 0.02% NaN3/PBS). Wells were filled with squeeze bottle, and then blotted against paper towel.

Wg binding was accomplished diluting Wg-containing or control media in diluent solution (1% BSA in TAPS), and add 50 ul to each well and then incubating at room temperature overnight. The wells were then washed 5 times as disclosed above. The primary antibody was then added by diluting the anti-Wg antibody (mouse monoclonal) in diluent solution to 1:1000, and add 50 ul to each well and incubating at 37° C. for 2 hours. The wells were then washed 5 times as disclosed above.

The secondary antibody was added by diluting this secondary antibody (goat anti-mouse-alkaline phosphatase conjugate) in diluent solution (using a conjugate from TAGO Inc. cat #4650 at a 1:400 dilution); add 50 ul to each well and incubating at 37° C. or 2 hours. The wells were then washed 5 times as disclosed above. Substrate was prepared by dissolving the substrate, p-nitrophenolphosphate (Sigma cat#2640) in carbonate buffer (1 mM $MgCl_2$/0.1M $Na_2CO_3$ pH 9.8) to a final concentration of 2 mg/ml. 65 ul of this substrate was then added to each well and read OD at 405 nm.

Competition Assay

Similar to standard assay discussed above, except Wg-containing medium is preincubated with varying concentrations of FRP or related protein to assess the ability of these proteins to bind Wg. This is manifested by a reduction in Wingless binding to the FRP-coated ELISA well. Typically preincubation is performed at room temperature for 1 hour.

Figure 14:
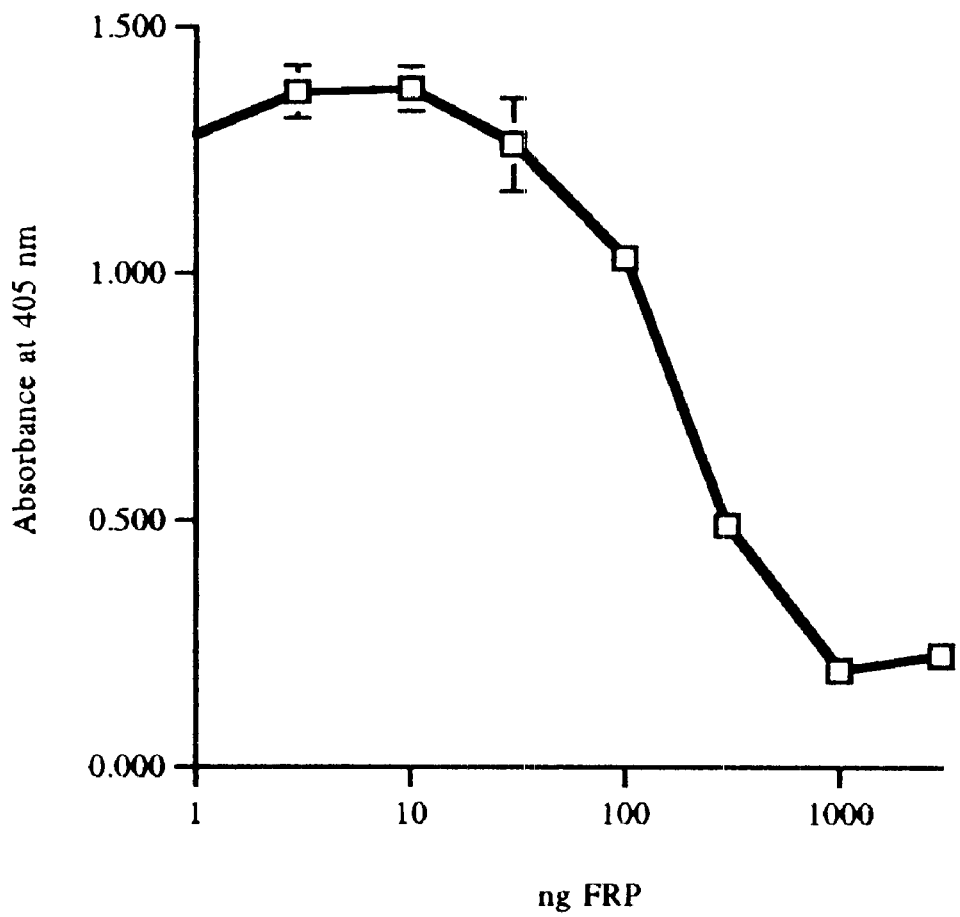
FIG. 14 shows an ELISA type competition assay showing the ability of soluble FRP to block Wg binding to FRP coated cells.

A related variation of the ELISA involves preincubation of Wg medium with proteoglycan such as heparin to assess its effect on subsequent binding to FRP coated wells. Medium can be preincubated with heparin and FRP simultaneously. As an alternative, heparin and/or FRP (or FRP-related proteins) can be added to the medium in the ELISA well without prior incubation. FIG. 14 provides an illustration of these results. Specifically, FIG. 14 illustrates how soluble FRP (ng of FRP/50 ul of Wg containing medium) influences Wg binding to bound FRP in ELISA format.

Preparation of Conditioned Medium from Drosophila S2 Cells—Control S2 and Cells Transfected with Heat Shock-Wingless Construct Growth medium utilized in this assay was Schneider's Drosophila Medium (Gibco cat #11720–034)+supplements. The medium for conditioning was Shields and Sang M3 Insect Medium (Sigma cat# S3652).

The Recovery of frozen cells appears to be the time when cells are most fragile (aside from recovery period, the cells are quite hardy). A key point is to avoid diluting cells until they clearly are thriving. Specifically, an ampule of ~10 million cells in a T-25 flask with final volume of 5–6 ml medium consisting of: Schneider's medium, 10% fetal bovine serum, penicillin (100 units/ml) and streptomycin (100 ug/ml); incubated at 26° C. Periodically, a small amount (1–2 ml) of fresh medium, prewarmed to room temperature was added to the solution, allowing the cell population to become quite dense (turbid) prior to subculture.

For the initial subculture, the cell suspension was transferred with pipette to a T-75 flask containing 20–25 ml of the above medium; typically suspension was diluted from 1:2 to 1:10, or perhaps even greater. Because some cells will remain adherent to the original T-25 flask, fresh medium was added to it to maintain a viable culture. Cells typically grow well at this point. For the subsequent subculture, dense (turbid) cultures were split, usually 1:10, into T-175 flasks for experiments. Cultures become dense and ready for use in ~1 week.

Heat Shock Protocol

The heat shock protocol was carried out by the following steps:
1. Incubate culture at 37° C. for 50 minutes;
2. Transfer culture to room temp (26° C.), and incubate for 40 minutes;
3. Pellet cells at low speed (3000 rpm, 5 minutes in standard lab bench centrifuge);
4. Resuspend pellets 3 times with serum-free Shields and Sang M3 Insect Medium, 20–40 ml/wash and obtain cell count (alternatively one can determine cell count with aliquot of sample during step 1), (typically, cell number is determined after the second resuspension by removing an aliquot, diluting it 5-fold and measuring cell count with a hemacytometer);
5. After the third wash, resuspend cells in Shields and Sang medium at a concentration of 25 million cells/ml and incubate for 5 hours at 26° C.; and
6. Pellet cells as before and collect supernatant for use as conditioned medium.

FRP-Wg Crosslinking

FRP-Wg interactions in a cell-free setting were studied first, as variables are more easily controlled in such systems than in cellular assays. The crosslinking analysis may be extended to cellular systems. In particular, one can assess FRP binding to epitope-tagged, Wnt family members expressed in appropriate host cells such as NIH/3T3 fibroblasts. Crosslinked complexes consisting of $^{125}$I-FRP and Wnt protein were immunoprecipitated with antibodies directly against the epitope tag.

A method for detection of FRP-Wg complexes by crosslinking analysis is as follows.

I. The iodination reaction can be accomplished by reacting 10 ug of purified recombinant FRP and 1 milliCurie of Na$^{125}$I with chloramine-T for 1 minute at room temperature (additional details essentially as described in Bottaro DP et al. J Biol. Chem 265: 12767–12770, (1990)).

The $^{125}$-FRP can be isolated by heparin-Sepharose chromatography. Specifically, tracer was eluted with phosphate buffer (pH7.4) containing 1.0 M NaCl and 1 mg/ml bovine serum albumin (BSA). Certain iodinated FRP derivatives can be recovered on desalting columns (containing resins such as G10) that serve to separate protein tracer from free sodium iodide. Tracer was stored frozen and subjected to not more than a few rounds of freeze-thawing prior to use.

II. Binding of tracer to Wg (all performed at room temperature) can be undertaken as follows. Typically ~1 microCurie (though amount could vary), of $^{125}$-FRP, was incubated with medium from Wg-expressing S2 cells (or control S2 cells) in a final volume of 50 ul for 40 minute. Varying amounts of additional reagents, such as heparin and/or unlabeled FRP, were added in some experiments. After binding period, crosslinking reagent bis (sulfosuccinimidyl) suberate (BS$^3$) was added at a final concentration of 1 mM and incubation continued for 20 minutes. The crosslinking reaction was terminated by the addition of Tris-HCl and glycine (final concentrations were 1 mM and 20 mM, respectively).

III. Detection of crosslinked complexes was undertaken by incubating all or most of the reaction mixture with antibody directed against Wg overnight at 4° C. Protein G-coupled resin (~50 ul slurry of GammaBind, Pharmacia) was then added along with buffer A (50 mM HEPES pH 7.4, 5 mM EDTA, 50 mM NaCl, 1% Triton X-100, 6 mM Na$_4$P$_2$O$_7$, 50 mM NaF, 0.35 mg/ml PMSF,10 ug/mi aprotinin and 10 ug/ml leupeptin) to bring final volume to ~0.5 ml. The reaction mixture was incubated for 1 hour at 4° C. in a rotary shaker. Typically a monoclonal antibody to Wg was used for immunoprecipitation, final concentration of 10 ug/ml (Brook et al., Science 273: 1373–1377 (1996)). After incubation, immune complexes were pelleted by centrifugation in microfuge (3 min at 14,000 rpm). Pellets were washed 3 times, each with 1 ml of buffer A.

Laemmli sample buffer was added to pellets, samples boiled for 4 minutes and proteins resolved by SDS-PAGE (8% polyacrylamide). In some instances, aliquots were removed from reaction mixture prior to addition of antibody and processed for electrophoresis. Gels were fixed (in 20% methanol, 10% acetic acid, 70% water) for 30 minutes at room temperature, dried and exposed to X-ray film at −70° C. for autoradiography.

Figure 15:
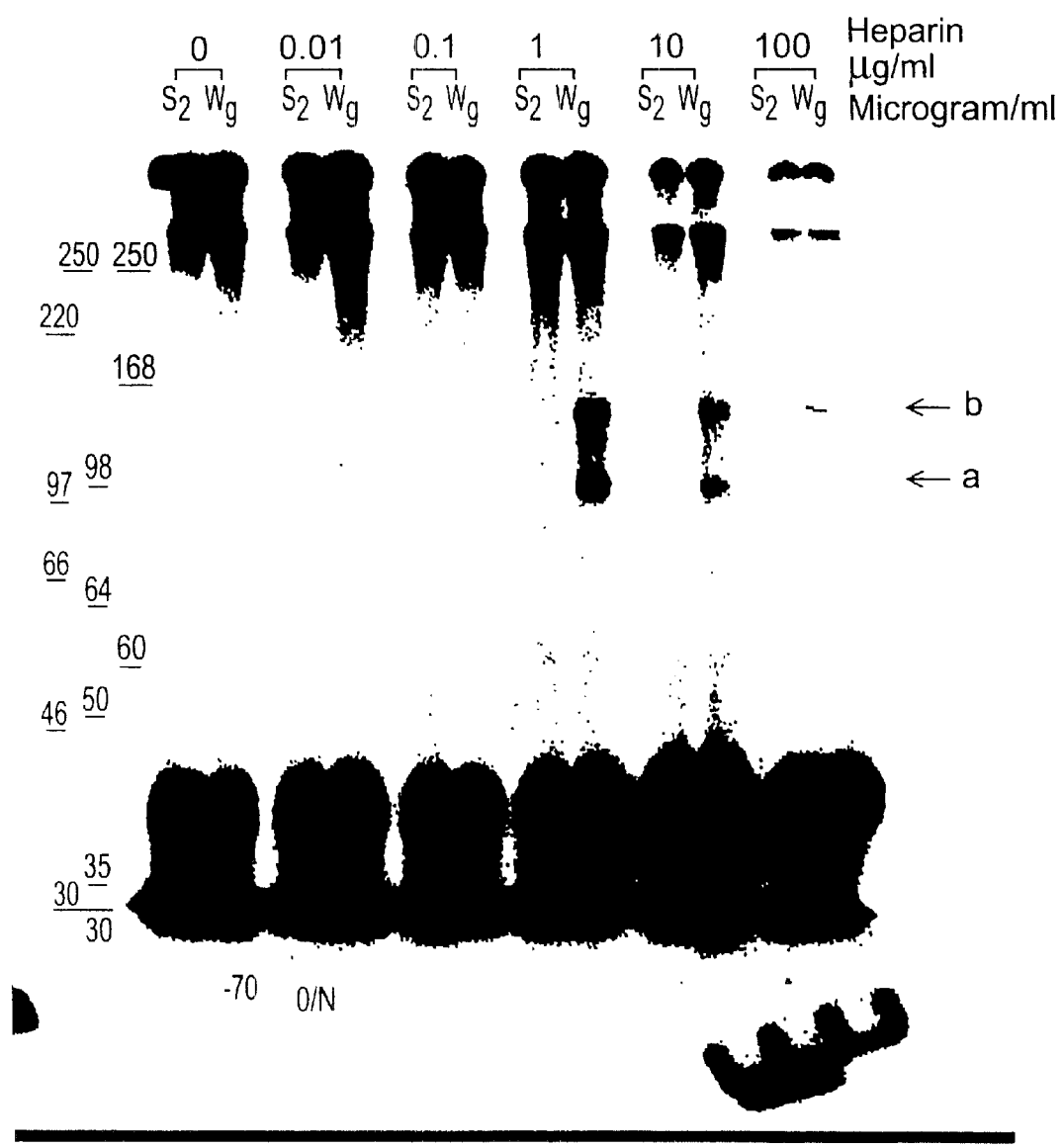
FIG. 15 shows the effects of varying the concentration of heparin in crosslinking reactions between $^{125}$I-FRP and Wg, with the crosslinked molecules being immunoprecipitated with an anti-Wg monoclonal antibody and separated by gel electrophoresis.
Figure 16:
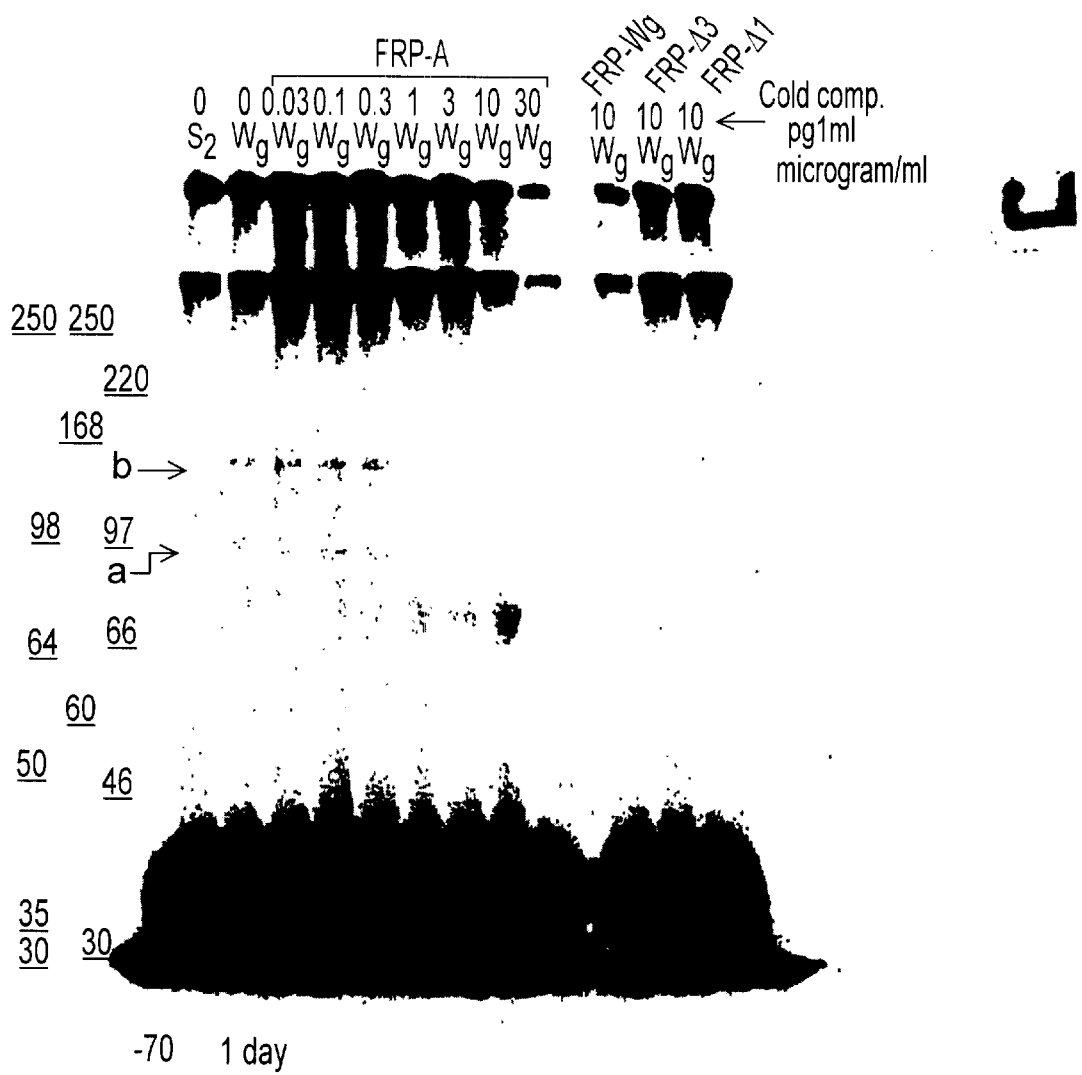
FIG. 16 shows the effects of varying the concentration of unlabelled FRP or FRP derivatives in crosslinking reactions between $^{125}$I-FRP and Wg, with the crosslinked molecules being immunoprecipitated with an anti-Wg monoclonal antibody and separated by gel electrophoresis.

FIGS. 15 and 16 illustrate these $^{125}$I-FRP-Wg Crosslinking reactions under different experimental conditions. Briefly, FIG. 15 shows the effects of varying the concentration of heparin in crosslinking reactions between $^{125}$I-FRP and Wg, with the crosslinked molecules being immunoprecipitated with an anti-Wg monoclonal antibody and separated by gel electrophoresis. In this assay, varying amounts of heparin (Fisher, porcine intestinal) were incubated with $^{125}$I-FRP (approximately 1 microCurie) and conditioned medium from Wg-expressing or control S2 cells at room temperature for 40 min. After a subsequent incubation with BS3 crosslinking agent, the reaction was quenched and the mixture was subjected to immunoprecipitation with monoclonal antibody to Wg. Precipitates were resolved by SDS-PAGE and labeled protein detected by autoradiography of dried gels.

FIG. 16 shows the effects of varying the concentration of unlabelled FRP or FRP derivatives in crosslinking reactions between $^{125}$I-FRP and Wg, with the crosslinked molecules being immunoprecipitated with an anti-Wg monoclonal antibody and separated by gel electrophoresis. Briefly, varying concentrations of unlabeled FRP or FRP derivatives were incubated with $^{125}$I-FRP, conditioned medium from Wg-expressing or control S2 cells and heparin at 1 ug/ml. After a subsequent incubation with BS3 crosslinking agent, the reaction was quenched and the mixture was subjected to immunoprecipitation with monoclonal antibody to Wg. Precipitates were resolved by SDS-PAGE and labeled protein detected by autoradiography of dried gels.

Example 9

Modulation of Embryonic Kidney Cell Tubulogenesis by FRP

Induction of tubulogenesis in culture of isolated metanephric mesenchyme was assessed. This organ culture system was described in an article by Karavanova ID et al. (Development 122: 4159–4167, 1996). In brief, kidneys were removed from F344 rat embryos 13 days post coitum. Metanephric mesenchyme was separated from ureteric bud by enzyme treatment, and cultured on collagen-coated filters. Tissue incubated with serum-free conditioned medium from a rat ureteric bud cell line (RUB1) supplemented with basic FGF and TGFα was induced to differentiate into epithelial tubular structures corresponding to nephrons.

Remarkably, if cultures treated with RUB1 conditioned medium, basic FGF and TGFα also received purified recombinant FRP (5 ug/ml) the induction of tubular structures was completely inhibited. Interestingly, the mesenchymal cells did not die; they even appeared to increase in number and the cultures grew larger during the 3 day incubation period. This result, an increase in condensed mesenchyme but an apparent failure to differentiate into epithelial cells and subsequent failure to form tubular structures, was observed in vivo in mice that were targeted for loss of Wnt 4 expression (Stark K et al. Nature 372: 679–683, 1994). Moreover, other Wnt family members are expressed in kidney and may participate in this process of differentiation and morphogenesis (see Karavanova et al. 1996). Thus, this preliminary result provides additional support for the idea that FRP can function as a soluble antagonist of Wnt activity. On a more elementary level, it demonstrates that purified, recombinant FRP has biological activity.

What is claimed is:

1. An isolated polynucleotide comprising a nucleic acid sequence encoding human Frizzled Related Protein having the amino acid sequence of SEQ ID No. 3.

2. The polynucleotide of claim 1 wherein the polynucleotide sequence is codon optimized for a specific host cell.

3. A vector comprising the polynucleotide of claim 1.

4. The vector of claim 3, wherein the polynucleotide is operably linked to at least one control sequence capable of being recognized by a host cell transformed with the vector.

5. The vector of claim 4, wherein at least one control sequence is a cytomegalovirus promoter.

6. A host cell comprising the vector of claim 4.

7. The host cell of claim 6, wherein the host cells are Madin-Darby canine kidney cells.

8. A process for producing human Frized Related Protein comprising culturing the host cell of claim 6 under conditions such that human Frizzled Related Protein is produced.

9. An isolated polynucleotide comprising a nucleic acid sequence encoding human Frizzled Related Protein having the amino acid sequence of SEQ ID No. 4.

10. The polynucleotide of claim 9 wherein the polynucleotide sequence is codon optimized for a specific host cell.

11. A vector comprising the polynucleotide of claim 9.

12. The vector of claim 1, wherein the polynucleotide is operably linked to at least one control sequence capable of being recognized by a host cell transformed with the vector.

13. The vector of claim 12, wherein at least one control sequence is a cytomegalovirus promoter.

14. A host cell comprising the vector of claim 12.

15. The host cell of claim 14, wherein the host cells are Madin-Darby canine kidney cells.

16. A process for producing human Frizzled Related Protein comprising culturing the host cell of claim 14 under conditions such that human Frizzled Related Protein is produced.

17. A polynucleotide complementary to an mRNA encoding a human Frizzled Related Protein of SEQ ID NO: 3 or SEQ ID NO: 4.

18. An isolated polynucleotide comprising a cDNA or a mRNA encoding human Frizzled Related Protein having the amino acid sequence of SEQ ID No. 3.

19. An isolated polynucleotide comprising a cDNA or a mRNA encoding human Frizzled Related Protein having the amino acid sequence of SEQ ID No. 4.

20. An isolated polynucleotide comprising the nucleic acid sequence shown in SEQ ID No. 1.

21. An isolated polynucleotide comprising the nucleic acid sequence shown in SEQ ID NO. 2.

22. An isolated polynucleotide comprising a nucleic acid sequence encoding human Frizzled Related Protein having at least 90% sequence identity with the amino acid sequence of SEQ ID NO: 3 or SEQ ID NO: 4, wherein the human Frizzled Related Protein can modulate Wnt biological activity.

23. A vector comprising the polynucteotide of claim 22.

24. The vector of claim 23, wherein the polynucleotide is operably linked to at least one control sequence capable of being recognized by a host cell transformed with the vector.

25. The vector of claim 24, wherein at least one control sequence is a cytomegalovirus promoter.

26. A host cell comprising the vector of claim 24.

27. The host cell of claim 26, wherein the host cells are Madin-Darby canine kidney cells.

28. A process for producing human Frizzled Related Protein comprising culturing the host cell of claim 26 under conditions such that the human Frizzled Related Protein polypeptide is produced.

29. The isolated polynucleotide recited in claim 22, wherein the polynucleotide encodes a human Frizzled Related Protein having at least 95% sequence identity with the amino acid sequence of SEQ ID NO: 3 or SEQ ID NO: 4.

30. A vector comprising the polynucleotide of claim 29.

31. The vector of claim 30, wherein the polynucleotide is operably linked to at least one control sequence capable of being recognized by a host cell transformed with the vector.

32. The vector of claim 31, wherein at least one control sequence is a cytomegalovirus promoter.

33. A host cell comprising the vector of claim 31.

34. The host cell of claim 33, wherein the host cells are Madin-Darby canine kidney cells.

35. A process for producing human Frizzed Related Protein comprising culturing the host cell of claim 33 uder conditions such that the human Frizzled Related Protein is produced.

36. The isolated polynucleotide recited in claim 22 wherein the polynucleotide encodes a human Frizzled Related Protein having at least 90% sequence identity with the amino acid sequence of SEQ ID NO: 3.

37. The isolated polynucleotide recited in claim 22 wherein the polynucleotide encodes a human Frizzled Related Protein having at least 95% sequence identity with the amino acid sequence of SEQ ID NO: 3.

38. The isolated polynucleotide of claim 22 wherein the polynucleotide encodes a human Frizzled Related Protein having at least 90% sequence identity with the amino acid sequence of SEQ ID NO: 4.

39. The isolated polynucleotide of claim 22 wherein the polynucleotide encodes a human Frizzled Related Protein having at least 95% sequence identity with the amino acid sequence of SEQ ID NO: 4.

40. An isolated polynucleotide comprising a nucleic acid sequence that shares at least 85% sequence identity with the nucleic acid sequence shown in SEQ ID NO. 1, wherein the polynucleotide encodes a human Frizzled Related Protein that can modulate Wnt biological activity.

41. The isolated polynucleotide recited in claim 40, wherein the polynucleotide shares at least 90% sequence identity with the nucleic acid sequence shown in SEQ ID NO: 1.

42. The isolated polynucleotide recited in claim 40, wherein the polynucleotide shares at least 95% sequence identity with the nucleic acid sequence shown in SEQ ID NO: 1.

43. An isolated polynucleotide comprising a nucleic acid sequence that shares at least 85% sequence identity with the nucleic acid sequence shown in SEQ ID NO. 2, wherein the polynucleotide encodes a human Frizzled Related Protein that can modulate Wnt biological activity.

44. The isolated polynucleotide recited in claim 43, wherein the polynucleotide shares at least 90% sequence identity with the nucleic acid sequence shown in SEQ ID NO: 2.

45. The isolated polynucleotide recited in claim 43, wherein the polynucleotide shares at least 95% sequence identity with the nucleic acid sequence shown in SEQ ID NO: 2.

46. An isolated polynucleotide comprising a nucleic acid sequence that shares at least 85% sequence identity with the nucleic acid sequence shown in SEQ ID NO. 27, wherein the polynucleotide encodes a human Frizzled Related Protein that can modulate Wnt biological activity.

47. The isolated polynucleotide recited in claim 46, wherein the polynucleotide shares at least 90% sequence identity with the nucleic acid sequence shown in SEQ ID NO: 27.

48. The isolated polynucleotide recited in claim 46, wherein the polynucleotide shares at least 95% sequence identity with the nucleic acid sequence shown in SEQ ID NO: 27.

49. The isolated nucleic acid sequence of claim 43, wherein the expression of the nucleic acid sequence is reduced in carcinoma of the mammary gland.

* * * * *

UNITED STATES PATENT AND TRADEMARK OFFICE
CERTIFICATE OF CORRECTION

PATENT NO. : 6,479,255 B1
DATED : November 12, 2002
INVENTOR(S) : Rubin et al.

It is certified that error appears in the above-identified patent and that said Letters Patent is hereby corrected as shown below:

Column 65,
Line 37, "The vector of claim 1" should read -- The vector of claim 11 --.

Signed and Sealed this

Twenty-sixth Day of October, 2004

JON W. DUDAS
*Director of the United States Patent and Trademark Office*

SEQUENCE LISTING

<160> NUMBER OF SEQ ID NOS: 27

<210> SEQ ID NO 1
<211> LENGTH: 2078
<212> TYPE: DNA
<213> ORGANISM: Homo sapiens

<400> SEQUENCE: 1

```
cctgcagcct ccggagtcag tgccgcgcgc ccgccgcccc gcgccttcct gctcgccgca      60
cctccgggag ccggggcgca cccagcccgc agcgccgcct ccccgcccgc gccgcctccg     120
accgcaggcc gagggccgcc actggccggg gggaccgggc agcagcttgc ggccgcggag     180
ccgggcaacg ctggggactg cgccttttgt ccccggaggt ccctggaagt ttgcggcagg     240
acgcgcgcgg ggaggcggcg gaggcagccc cgacgtcgcg gagaacaggg cgcagagccg     300
gcatgggcat cgggcgcagc gaggggggcc gccgcgggc agccctgggc gtgctgctgg     360
cgctgggcgc ggcgcttctg gccgtgggct cggccagcga gtacgactac gtgagcttcc     420
agtcggacat cggcccgtac cagagcgggc gcttctacac caagccacct cagtgcgtgg     480
acatccccgc ggacctgcgg ctgtgccaca acgtgggcta caagaagatg gtgctgccca     540
acctgctgga gcacgagacc atggcggagg tgaagcagca ggccagcagc tgggtgcccc     600
tgctcaacaa gaactgccac gccgggaccc aggtcttcct ctgctcgctc ttcgcgcccg     660
tctgcctgga ccggcccatc tacccgtgtc gctggctctg cgaggccgtg cgcgactcgt     720
gcgagccggt catgcagttc ttcggcttct actggccgcga gatgcttaag tgtgacaagt     780
tcccggaggg ggacgtctgc atcgccatga cgccgcccaa tgccaccgaa gcctccaagc     840
cccaaggcac aacggtgtgt cctccctgtg acaacgagtt gaaatctgag gccatcattg     900
aacatctctg tgccagcgag tttgcactga ggatgaaaat aaaagaagtg aaaaaagaaa     960
atggcgacaa gaagattgtc cccaagaaga agaagcccct gaagttgggg cccatcaaga    1020
agaaggacct gaagaagctt gtgctgtacc tgaagaatgg ggctgactgt ccctgccacc    1080
agctggacaa cctcagccac cacttcctca tcatgggccg caaggtgaag agccagtact    1140
tgctgacggc catccacaag tgggacaaga aaacaaggag gttcaaaaac ttcatgaaga    1200
aaatgaaaaa ccatgagtgc cccacctttc agtccgtgtt taagtgattc tcccgggggc    1260
```

-continued

```
agggtgggga gggagcctcg ggtggggtgg gagcggggggg gacagtgccc gggaacccgt    1320
ggtcacacac acgcactgcc ctgtcagtag tggacattgt aatccagtcg gcttgttctt    1380
gcagcattcc cgctcccttt ccctccatag ccacgctcca aacccagggg tagccatggc    1440
cgggtaaagc aagggccatt tagattagga aggttttttaa gatccgcaat gtggagcagc    1500
agccactgca caggaggagg tgacaaacca tttccaacag caacacagcc actaaaacac    1560
aaaaaggggg attgggcgga aagtgagagc cagcagcaaa aactacattt tgcaacttgt    1620
tggtgtggat ctattggctg atctatgcct ttcaactaga aaattctaat gattggcaag    1680
tcacgttgtt ttcaggtcca gagtagtttc tttctgtctg ctttaaatgg aaacagactc    1740
ataccacact tacaattaag gtcaagccca gaaagtgata agtgcaggga ggaaaagtgc    1800
aagtccatta tctaatagtg acagcaaagg gaccagggga gaggcattgc cttctctgcc    1860
cacagtcttt ccgtgtgatt gtctttgaat ctgaatcagc cagtctcaga tgccccaaag    1920
tttcggttcc tatgagcccg ggcatgatc tgatccccaa gacatgtgga ggggcagcct    1980
gtgcctgcct ttgtgtcaga aaaaggaaac cacagtgagc ctgagagaga cggcgatttt    2040
cgggctgaga aggcagtagt tttcaaaaca catagtta                            2078
```

<210> SEQ ID NO 2
<211> LENGTH: 2075
<212> TYPE: DNA
<213> ORGANISM: Homo sapiens

<400> SEQUENCE: 2

```
cctgcagcct ccggagtcag tgccgcgcgc ccgccgcccc gcgccttcct gctcgccgca     60
cctccgggag ccggggcgca cccagcccgc agcgccgcct cccgcccgc gccgcctccg    120 accgcaggcc gagggccgcc actggccggg gggaccgggc agcagcttgc ggccgcggag    180
ccgggcaacg ctggggactg cgccttttgt ccccggaggt ccctggaagt ttgcggcagg    240
acgcgcgcgg ggaggcggcg gaggcagccc cgacgtcgcg gagaacaggg cgcagagccg    300
gcatgggcat cgggcgcagc gagggggggcc gccgcggggc cctgggcgtg ctgctggcgc    360
tgggcgcggc gcttctggcc gtgggctcgg ccagcgagta cgactacgtg agcttccagt    420
cggacatcgg cccgtaccag agcgggcgct tctacaccaa gccacctcag tgcgtggaca    480
tccccgcgga cctgcggctg tgccacaacg tgggctacaa gaagatggtg ctgcccaacc    540
tgctggagca cgagaccatg gcggaggtga agcagcaggc cagcagctgg gtgccccctgc    600 tcaacaagaa ctgccacgcc gggacccagg tcttcctctg ctcgctcttc gcgcccgtct    660
gcctggaccg gcccatctac ccgtgtcgct ggctctgcga ggccgtgcgc gactcgtgcg    720
agccggtcat gcagttcttc ggcttctact ggcccgagat gcttaagtgt gacaagttcc    780 cggagggggga cgtctgcatc gccatgacga cgcccaatgc caccgaagcc tccaagcccc    840
aaggcacaac ggtgtgtcct ccctgtgaca acagttgaa atctgaggcc atcattgaac    900
atctctgtgc cagcgagttt gcactgagga tgaaaataaa agaagtgaaa aagaaaatg    960 gcgacaagaa gattgtcccc aagaagaaga agcccctgaa gttggggccc atcaagaaga    1020
aggacctgaa gaagcttgtg ctgtacctga agaatggggc tgactgtccc tgccaccagc    1080
tggacaacct cagccaccac ttcctcatca tgggccgcaa ggtgaagagc cagtacttgc    1140
tgacggccat ccacagtgg gacaagaaaa acaaggagtt caaaaacttc atgaagaaaa    1200
tgaaaaacca tgagtgcccc accttttcagt ccgtgtttaa gtgattctcc cggggcagg    1260 gtggggaggg agcctcgggt ggggtgggag cggggggggac agtgcccggg aacccgtggt    1320
```

-continued

```
cacacacacg cactgccctg tcagtagtgg acattgtaat ccagtcggct tgttcttgca    1380
gcattcccgc tccctttccc tccatagcca cgctccaaac cccagggtag ccatggccgg    1440
gtaaagcaag ggccatttag attaggaagg tttttaagat ccgcaatgtg gagcagcagc    1500
cactgcacag gaggaggtga caaccatttt ccaacagcaa cacagccact aaaacacaaa    1560 aaggggggatt gggcggaaag tgagagccag cagcaaaaac tacattttgc aacttgttgg    1620
tgtggatcta ttggctgatc tatgcctttc aactagaaaa ttctaatgat tggcaagtca    1680
cgttgttttc aggtccagag tagtttcttt ctgtctgctt taaatggaaa cagactcata    1740
ccacacttac aattaaggtc aagcccagaa agtgataagt gcaggggagga aaagtgcaag   1800 tccattatct aatagtgaca gcaaagggac caggggagag gcattgcctt ctctgcccac    1860
agtctttccg tgtgattgtc tttgaatctg aatcagccag tctcagatgc cccaaagttt    1920
cggttcctat gagcccgggg catgatctga tccccaagac atgtggaggg gcagcctgtg    1980
cctgcctttg tgtcagaaaa aggaaaccac agtgagcctg agagagacgg cgattttcgg    2040
gctgagaagg cagtagtttt caaaacacat agtta                               2075
```

<210> SEQ ID NO 3
<211> LENGTH: 314
<212> TYPE: PRT
<213> ORGANISM: Homo sapiens

<400> SEQUENCE: 3

```
Met Gly Ile Gly Arg Ser Glu Gly Gly Arg Gly Ala Ala Leu Gly
1               5                   10                  15

Val Leu Ala Leu Gly Ala Ala Leu Ala Val Gly Ser Ala Ser
            20                  25                  30

Glu Tyr Asp Tyr Val Ser Phe Gly Ser Asp Ile Gly Pro Tyr Gly Ser
            35                  40                  45

Gly Arg Phe Tyr Thr Lys Pro Pro Gly Cys Val Asp Ile Pro Ala Asp
        50                  55                  60

Leu Arg Leu Cys His Asn Val Gly Tyr Lys Lys Met Val Leu Pro Asn
65                  70                  75                  80

Leu Leu Glu His Glu Thr Met Ala Glu Val Lys Gly Gly Ala Ser Ser
                85                  90                  95

Trp Val Pro Leu Leu Asn Lys Asn Cys His Ala Gly Thr Gly Val Phe
            100                 105                 110

Leu Cys Ser Leu Phe Ala Pro Val Cys Leu Asp Arg Pro Ile Tyr Pro
            115                 120                 125

Cys Arg Trp Leu Cys Glu Ala Val Arg Asp Ser Cys Glu Pro Val Met
        130                 135                 140

Gly Phe Phe Gly Phe Tyr Trp Pro Glu Met Leu Lys Cys Asp Lys Phe
145                 150                 155                 160

Pro Glu Gly Asp Val Cys Ile Ala Met Thr Pro Pro Asn Ala Thr Glu
                165                 170                 175

Ala Ser Lys Pro Gly Gly Thr Thr Val Cys Pro Pro Cys Asp Asn Glu
            180                 185                 190

Leu Lys Ser Glu Ala Ile Ile Glu His Leu Cys Ala Ser Glu Phe Ala
            195                 200                 205

Leu Arg Met Lys Ile Lys Glu Val Lys Glu Asn Gly Asp Lys Lys
        210                 215                 220

Ile Val Pro Lys Lys Lys Pro Leu Lys Leu Gly Pro Ile Lys Lys
225                 230                 235                 240
```

-continued

```
Lys Asp Leu Lys Lys Leu Val Leu Tyr Leu Lys Asn Gly Ala Asp Cys
            245                 250                 255

Pro Cys His Gly Leu Asp Asn Leu Ser His His Phe Leu Ile Met Gly
        260                 265                 270

Arg Lys Val Lys Ser Gly Tyr Leu Leu Thr Ala Ile His Lys Trp Asp
        275                 280                 285

Lys Lys Asn Lys Glu Phe Lys Asn Phe Met Lys Lys Met Lys Asn His
        290                 295                 300

Glu Cys Pro Thr Phe Gly Ser Val Phe Lys
305                 310

<210> SEQ ID NO 4
<211> LENGTH: 313
<212> TYPE: PRT
<213> ORGANISM: Homo sapiens

<400> SEQUENCE: 4

Met Gly Ile Gly Arg Ser Glu Gly Gly Arg Gly Ala Leu Gly Val
1               5                   10                  15

Leu Leu Ala Leu Gly Ala Ala Leu Leu Ala Val Gly Ser Ala Ser Glu
            20                  25                  30

Tyr Asp Tyr Val Ser Phe Gly Ser Asp Ile Gly Pro Tyr Gly Ser Gly
        35                  40                  45

Arg Phe Tyr Thr Lys Pro Pro Gly Cys Val Asp Ile Pro Ala Asp Leu
50                  55                  60

Arg Leu Cys His Asn Val Gly Tyr Lys Lys Met Val Leu Pro Asn Leu
65                  70                  75                  80

Leu Glu His Glu Thr Met Ala Glu Val Lys Gly Gly Ala Ser Ser Trp
            85                  90                  95

Val Pro Leu Leu Asn Lys Asn Cys His Ala Gly Thr Gly Val Phe Leu
        100                 105                 110

Cys Ser Leu Phe Ala Pro Val Cys Leu Asp Arg Pro Ile Tyr Pro Cys
        115                 120                 125

Arg Trp Leu Cys Glu Ala Val Arg Asp Ser Cys Glu Pro Val Met Gly
        130                 135                 140

Phe Phe Gly Phe Tyr Trp Pro Glu Met Leu Lys Cys Asp Lys Phe Pro
145                 150                 155                 160

Glu Gly Asp Val Cys Ile Ala Met Thr Pro Pro Asn Ala Thr Glu Ala
            165                 170                 175

Ser Lys Pro Gly Gly Thr Thr Val Cys Pro Pro Cys Asp Asn Glu Leu
        180                 185                 190

Lys Ser Glu Ala Ile Ile Glu His Leu Cys Ala Ser Glu Phe Ala Leu
        195                 200                 205

Arg Met Lys Ile Lys Glu Val Lys Glu Asn Gly Asp Lys Lys Ile
210                 215                 220

Val Pro Lys Lys Lys Pro Leu Lys Leu Gly Pro Ile Lys Lys Lys
225                 230                 235                 240

Asp Leu Lys Lys Leu Val Leu Tyr Leu Lys Asn Gly Ala Asp Cys Pro
            245                 250                 255

Cys His Gly Leu Asp Asn Leu Ser His His Phe Leu Ile Met Gly Arg
        260                 265                 270

Lys Val Lys Ser Gly Tyr Leu Leu Thr Ala Ile His Lys Trp Asp Lys
        275                 280                 285

Lys Asn Lys Glu Phe Lys Asn Phe Met Lys Lys Met Lys Asn His Glu
```

```
                    290                 295                 300
Cys Pro Thr Phe Gly Ser Val Phe Lys
305                 310
```

<210> SEQ ID NO 5
<211> LENGTH: 9
<212> TYPE: PRT
<213> ORGANISM: Homo sapiens

<400> SEQUENCE: 5

```
Asn Val Gly Tyr Lys Lys Met Val Leu
1               5
```

<210> SEQ ID NO 6
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Where "Xaa" is any amino acid.

<400> SEQUENCE: 6

```
Phe Tyr Thr Lys Pro Pro Gly Xaa Val
1               5
```

<210> SEQ ID NO 7
<211> LENGTH: 40
<212> TYPE: PRT
<213> ORGANISM: Homo sapiens
<220> FEATURE:
<221> NAME/KEY: MISC_FEATURE
<222> LOCATION: (20)..(20),(30)..(31)
<223> OTHER INFORMATION: Where "Xaa" is any amino acid.

<400> SEQUENCE: 7

```
Phe Gly Ser Asp Ile Gly Pro Tyr Gly Ser Gly Arg Phe Tyr Thr Lys
1               5                   10                  15
Pro Pro Gly Xaa Val Asp Ile Pro Ala Asp Leu Arg Leu Xaa Xaa Asn
                20                  25                  30
Val Gly Tyr Lys Lys Met Val Leu
                35                  40
```

<210> SEQ ID NO 8
<211> LENGTH: 10
<212> TYPE: DNA
<213> ORGANISM: Homo sapiens

<400> SEQUENCE: 8

```
gccrccatgg                                                              10
```

<210> SEQ ID NO 9
<211> LENGTH: 111
<212> TYPE: PRT
<213> ORGANISM: Homo sapiens

<400> SEQUENCE: 9

```
Cys Gly Pro Ile Ser Ile Pro Leu Cys Thr Asp Ile Ala Tyr Asn Gly
1               5                   10                  15
Thr Ile Met Pro Asn Leu Leu Gly His Thr Asn Gly Glu Asp Ala Gly
                20                  25                  30
Leu Glu Val His Gly Phe Tyr Pro Leu Val Lys Gly Cys Ser Pro Glu
                35                  40                  45
```

-continued

Leu Arg Phe Phe Leu Cys Ser Met Tyr Ala Pro Val Cys Thr Val Leu
    50                  55                  60

Glu Gly Ala Ile Pro Pro Cys Arg Ser Ile Cys Glu Arg Ala Arg Gly
65                  70                  75                  80

Gly Cys Glu Ala Leu Met Asn Lys Phe Gly Phe Gly Trp Pro Glu Arg
                85                  90                  95

Leu Arg Cys Glu His Phe Pro Arg His Gly Ala Glu Gly Ile Cys
                100                 105                 110

<210> SEQ ID NO 10
<211> LENGTH: 115
<212> TYPE: PRT
<213> ORGANISM: Homo sapiens

<400> SEQUENCE: 10

Cys Gly Glu Ile Thr Val Pro Met Cys Arg Gly Ile Gly Tyr Asn Leu
1               5                   10                  15

Thr His Met Pro Asn Gly Phe Asn His Asp Thr Gly Asp Glu Ala Gly
                20                  25                  30

Leu Glu Val His Gly Phe Trp Pro Leu Val Glu Ile Gly Cys Ser Pro
            35                  40                  45

Asp Leu Arg Phe Phe Leu Cys Thr Met Tyr Thr Pro Ile Cys Leu Pro
    50                  55                  60

Asp Tyr His Lys Pro Leu Pro Pro Cys Arg Ser Val Cys Glu Arg Ala
65                  70                  75                  80

Lys Ala Gly Cys Ser Pro Leu Met Arg Gly Tyr Gly Phe Ala Trp Pro
                85                  90                  95

Glu Arg Met Ser Cys Asp Arg Leu Pro Val Leu Gly Arg Asp Ala Glu
                100                 105                 110

Val Leu Cys
        115

<210> SEQ ID NO 11
<211> LENGTH: 106
<212> TYPE: PRT
<213> ORGANISM: Murine

<400> SEQUENCE: 11

Cys Glu Pro Ile Thr Leu Arg Met Cys Gly Asp Leu Pro Tyr Asn Thr
1               5                   10                  15

Thr Phe Met Pro Asn Leu Leu Asn His Tyr Asp Gly Gly Thr Ala Ala
                20                  25                  30

Leu Ala Met Glu Pro Phe His Pro Met Val Asn Leu Asp Cys Ser Arg
            35                  40                  45

Asp Phe Arg Pro Phe Leu Cys Ala Leu Tyr Ala Pro Ile Cys Met Glu
    50                  55                  60

Tyr Gly Arg Val Thr Leu Pro Cys Arg Arg Leu Cys Gly Arg Ala Tyr
65                  70                  75                  80

Ser Glu Cys Ser Lys Leu Met Glu Met Phe Gly Val Pro Trp Pro Glu
                85                  90                  95

Asp Met Glu Cys Ser Arg Phe Pro Asp Cys
                100                 105

<210> SEQ ID NO 12
<211> LENGTH: 114
<212> TYPE: PRT
<213> ORGANISM: Murine

-continued

```
<400> SEQUENCE: 12

Cys Asp Pro Ile Arg Ile Ala Met Cys Gly Asn Leu Gly Tyr Asn Val
1               5                  10                  15

Thr Lys Met Pro Asn Leu Val Gly His Glu Leu Gly Thr Asp Ala Glu
            20                  25                  30

Leu Gly Leu Thr Thr Phe Thr Pro Leu Ile Gly Tyr Gly Cys Ser Ser
        35                  40                  45

Gly Leu Gly Phe Phe Leu Cys Ser Val Tyr Val Pro Met Cys Thr Glu
    50                  55                  60

Lys Ile Asn Ile Pro Ile Gly Pro Cys Gly Gly Met Cys Leu Ser Val
65                  70                  75                  80

Lys Arg Arg Cys Glu Pro Val Leu Arg Glu Phe Gly Phe Ala Trp Pro
                85                  90                  95

Asp Thr Leu Asn Cys Ser Lys Phe Pro Pro Gly Asn Asp His Asn His
            100                 105                 110

Met Cys

<210> SEQ ID NO 13
<211> LENGTH: 106
<212> TYPE: PRT
<213> ORGANISM: Murine

<400> SEQUENCE: 13

Cys Glu Pro Ile Thr Val Pro Arg Cys Met Lys Met Thr Tyr Asn Met
1               5                  10                  15

Thr Phe Phe Pro Asn Leu Met Gly His Tyr Asp Gly Gly Ile Ala Ala
            20                  25                  30

Val Glu Met Gly His Phe Leu His Leu Ala Asn Leu Glu Cys Ser Pro
        35                  40                  45

Asn Ile Glu Met Phe Leu Cys Gly Ala Phe Ile Pro Thr Cys Thr Glu
    50                  55                  60

Gly Ile His Val Val Leu Pro Cys Arg Lys Leu Cys Glu Lys Ile Val
65                  70                  75                  80

Ser Asp Cys Lys Lys Leu Met Asp Thr Phe Gly Ile Arg Trp Pro Glu
                85                  90                  95

Glu Leu Glu Cys Asn Arg Leu Pro His Cys
            100                 105

<210> SEQ ID NO 14
<211> LENGTH: 111
<212> TYPE: PRT
<213> ORGANISM: Murine

<400> SEQUENCE: 14

Cys Gly Pro Ile Ser Ile Pro Leu Cys Thr Asp Ile Ala Tyr Asn Gly
1               5                  10                  15

Thr Ile Leu Pro Asn Leu Leu Gly His Thr Asn Gly Glu Asp Ala Gly
            20                  25                  30

Leu Glu Val His Gly Phe Tyr Pro Leu Val Lys Val Gly Cys Ser Pro
        35                  40                  45

Glu Leu Arg Phe Phe Leu Cys Ser Met Tyr Ala Pro Val Cys Thr Val
    50                  55                  60

Leu Asp Gly Ala Ile Pro Pro Cys Arg Ser Leu Cys Glu Arg Ala Arg
65                  70                  75                  80

Gly Cys Glu Ala Leu Met Asn Lys Phe Gly Phe Gly Trp Pro Glu Arg
                85                  90                  95
```

```
Leu Arg Cys Glu Asn Phe Pro Val His Gly Ala Gly Glu Ile Cys
            100                 105                 110

<210> SEQ ID NO 15
<211> LENGTH: 114
<212> TYPE: PRT
<213> ORGANISM: Murine

<400> SEQUENCE: 15

Cys Gly Glu Ile Thr Val Pro Leu Cys Lys Gly Ile Gly Tyr Asn Tyr
1               5                   10                  15

Thr Tyr Met Pro Asn Gly Phe Asn His Asp Thr Gly Asp Glu Ala Gly
            20                  25                  30

Leu Glu Val His Gly Phe Trp Pro Leu Val Glu Ile Gly Cys Ser Pro
            35                  40                  45

Asp Leu Lys Phe Phe Leu Cys Ser Met Tyr Thr Pro Ile Cys Leu Glu
        50                  55                  60

Asp Tyr Lys Lys Pro Leu Pro Pro Cys Arg Ser Val Cys Glu Arg Ala
65                  70                  75                  80

Lys Ala Gly Cys Ala Pro Leu Met Arg Gly Tyr Gly Phe Ala Trp Pro
                85                  90                  95

Asp Arg Met Arg Cys Asp Arg Leu Pro Glu Gly Gly Asn Pro Asp Thr
            100                 105                 110

Leu Cys

<210> SEQ ID NO 16
<211> LENGTH: 111
<212> TYPE: PRT
<213> ORGANISM: Rat

<400> SEQUENCE: 16

Cys Gly Pro Ile Ser Ile Pro Leu Cys Thr Asp Ile Ala Tyr Asn Gly
1               5                   10                  15

Thr Ile Met Pro Asn Leu Leu Gly His Thr Asn Gly Glu Asp Ala Gly
            20                  25                  30

Leu Glu Val His Gly Phe Tyr Pro Leu Val Lys Val Gly Cys Ser Ala
            35                  40                  45

Glu Leu Lys Phe Phe Leu Cys Ser Met Tyr Ala Pro Val Cys Thr Val
        50                  55                  60

Leu Glu Gly Ala Leu Pro Pro Cys Arg Ser Leu Cys Glu Arg Ala Gly
65                  70                  75                  80

Gly Cys Glu Ala Leu Met Asn Lys Phe Gly Phe Gly Trp Pro Asp Thr
                85                  90                  95

Leu Lys Cys Glu Lys Phe Pro Val His Gly Ala Gly Glu Leu Cys
            100                 105                 110

<210> SEQ ID NO 17
<211> LENGTH: 112
<212> TYPE: PRT
<213> ORGANISM: Rat

<400> SEQUENCE: 17

Cys Gly Pro Ile Ser Ile Pro Leu Cys Thr Asp Ile Ala Tyr Asn Gly
1               5                   10                  15

Thr Ile Met Pro Asn Leu Leu Gly His Thr Asn Gly Glu Asp Ala Gly
            20                  25                  30

Leu Glu Val His Gly Phe Tyr Pro Leu Val Lys Val Gly Cys Ser Pro
```

-continued

Glu Leu Arg Phe Phe Leu Cys Ser Met Tyr Ala Pro Val Cys Thr Val
             50                  55                  60

Leu Glu Gly Ala Ile Pro Pro Cys Arg Ser Ile Cys Glu Arg Ala Arg
 65                  70                  75                  80

Gly Gly Cys Glu Ala Leu Met Asn Lys Phe Gly Phe Gly Trp Pro Glu
                 85                  90                  95

Arg Leu Arg Cys Glu His Phe Pro Arg His Gly Ala Glu Gly Ile Cys
                100                 105                 110

<210> SEQ ID NO 18
<211> LENGTH: 111
<212> TYPE: PRT
<213> ORGANISM: Drosophila

<400> SEQUENCE: 18

Cys Glu Pro Ile Thr Ile Ser Ile Cys Lys Asn Ile Pro Tyr Asn Met
 1               5                  10                  15

Thr Ile Met Pro Asn Leu Ile Gly His Thr Lys Gly Glu Glu Ala Gly
                 20                  25                  30

Leu Glu Val His Gly Phe Ala Pro Leu Val Lys Ile Gly Cys Ser Asp
                 35                  40                  45

Asp Leu Gly Leu Phe Leu Cys Ser Leu Tyr Val Pro Val Cys Thr Ile
             50                  55                  60

Leu Glu Arg Pro Ile Pro Pro Cys Arg Ser Leu Cys Glu Ser Ala Arg
 65                  70                  75                  80

Val Cys Glu Lys Leu Met Lys Thr Tyr Asn Phe Asn Trp Pro Glu Asn
                 85                  90                  95

Leu Glu Cys Ser Lys Phe Pro Val His Gly Gly Glu Asp Leu Cys
                100                 105                 110

<210> SEQ ID NO 19
<211> LENGTH: 109
<212> TYPE: PRT
<213> ORGANISM: Homo sapiens

<400> SEQUENCE: 19

Cys Val Asp Ile Pro Ala Asp Leu Arg Leu Cys His Asn Val Gly Tyr
 1               5                  10                  15

Lys Lys Met Val Leu Pro Asn Leu Leu Glu His Glu Thr Met Ala Glu
                 20                  25                  30

Val Lys Gly Gly Ala Ser Ser Trp Val Pro Leu Leu Asn Lys Asn Cys
                 35                  40                  45

His Ala Gly Thr Gly Val Phe Leu Cys Ser Leu Phe Ala Pro Val Cys
             50                  55                  60

Leu Asp Arg Pro Ile Tyr Pro Cys Arg Trp Leu Cys Glu Ala Val Arg
 65                  70                  75                  80

Asp Ser Cys Glu Pro Val Met Gly Phe Phe Gly Phe Tyr Trp Pro Glu
                 85                  90                  95

Met Leu Lys Cys Asp Lys Phe Pro Glu Gly Asp Val Cys
                100                 105

<210> SEQ ID NO 20
<211> LENGTH: 114
<212> TYPE: PRT
<213> ORGANISM: Drosophila

<400> SEQUENCE: 20

```
Cys Glu Glu Ile Thr Ile Pro Met Cys Arg Gly Ile Gly Tyr Asn Met
1               5                   10                  15

Thr Ser Phe Pro Asn Glu Met Asn His Glu Thr Gly Asp Glu Ala Gly
            20                  25                  30

Leu Glu Val His Gly Phe Trp Pro Leu Val Glu Ile Lys Cys Ser Pro
        35                  40                  45

Asp Leu Lys Phe Phe Leu Cys Ser Met Tyr Thr Pro Ile Cys Leu Glu
    50                  55                  60

Asp Tyr His Lys Pro Leu Pro Val Cys Arg Ser Val Cys Glu Arg Ala
65                  70                  75                  80

Arg Ser Gly Cys Ala Pro Ile Met Gly Gly Tyr Ser Phe Glu Trp Pro
                85                  90                  95

Glu Arg Met Ala Cys Glu His Leu Pro Leu His Gly Asp Pro Asp Asn
                100                 105                 110

Leu Cys

<210> SEQ ID NO 21
<211> LENGTH: 114
<212> TYPE: PRT
<213> ORGANISM: C. elegans

<400> SEQUENCE: 21

Cys Gly Lys Val Asp His Glu Met Cys Asn Asp Leu Pro Tyr Asn Leu
1               5                   10                  15

Thr Ser Phe Pro Asn Leu Val Asp Glu Glu Ser Trp Lys Asp Ala Ser
            20                  25                  30

Glu Ser Ile Leu Thr Tyr Lys Pro Leu Leu Ser Val Val Cys Ser Glu
        35                  40                  45

Gly Leu Lys Phe Phe Leu Cys Ser Val Tyr Phe Pro Met Cys Asn Glu
    50                  55                  60

Lys Leu Ala Asn Pro Ile Gly Pro Cys Arg Pro Leu Cys Leu Ser Val
65                  70                  75                  80

Gly Glu Lys Cys Leu Pro Val Leu Glu Ser Phe Gly Phe Lys Trp Pro
                85                  90                  95

Asp Val Ile Arg Cys Asp Lys Phe Pro Leu Glu Asn Asn Arg Glu Lys
                100                 105                 110

Met Cys

<210> SEQ ID NO 22
<211> LENGTH: 110
<212> TYPE: PRT
<213> ORGANISM: Murine

<400> SEQUENCE: 22

Cys Leu Pro Leu Pro Pro Thr Leu Thr Leu Cys Ser Arg Leu Gly Ile
1               5                   10                  15

Gly His Phe Trp Leu Pro Asn His Leu His His Thr Asp Ser Val Glu
            20                  25                  30

Val Glu Ala Thr Val Gly Ala Trp Gly Arg Phe Leu His Thr Asn Cys
        35                  40                  45

His Pro Phe Leu Ala Trp Phe Cys Leu Leu Leu Ala Pro Ser Cys
    50                  55                  60

Gly Pro Gly Pro Pro Pro Leu Pro Pro Cys Arg Gly Phe Cys Glu
65                  70                  75                  80

Ala Leu Glu Asp Glu Cys Trp Asn Tyr Leu Ala Gly Asp Arg Leu Pro
```

```
                        85                  90                  95
Val Val Cys Ala Ser Leu Pro Ser Gly Glu Asp Gly Tyr Cys
                100                 105                 110

<210> SEQ ID NO 23
<211> LENGTH: 112
<212> TYPE: PRT
<213> ORGANISM: Homo sapiens

<400> SEQUENCE: 23

Cys Glu Pro Val Arg Ile Pro Leu Cys Lys Ser Leu Pro Trp Asn Met
1               5                   10                  15

Thr Lys Met Pro Asn His Leu His Ser Thr Gly Ala Asn Ala Ile Leu
                20                  25                  30

Ala Ile Glu Gly Phe Glu Gly Leu Leu Gly Thr His Cys Ser Pro Asp
            35                  40                  45

Leu Leu Phe Phe Leu Cys Ala Met Tyr Ala Pro Ile Cys Thr Ile Asp
        50                  55                  60

Phe Gly His Glu Pro Ile Asn Pro Cys Lys Ser Val Cys Glu Arg Ala
65                  70                  75                  80

Arg Gly Gly Cys Glu Pro Ile Leu Ile Lys Tyr Arg His Ser Trp Pro
                85                  90                  95

Glu Asn Leu Ala Cys Glu Glu Leu Pro Val Tyr Asp Arg Gly Val Cys
                100                 105                 110

<210> SEQ ID NO 24
<211> LENGTH: 113
<212> TYPE: PRT
<213> ORGANISM: Murine

<400> SEQUENCE: 24

Cys Lys Pro Ile Pro Ala Asn Leu Gly Leu Cys His Gly Ile Glu Tyr
1               5                   10                  15

Gly Asn Met Arg Leu Pro Asn Leu Leu Gly His Glu Thr Met Lys Glu
                20                  25                  30

Val Leu Glu Gly Ala Gly Ala Trp Ile Pro Leu Val Met Lys Gly Cys
            35                  40                  45

His Pro Asp Thr Lys Lys Phe Leu Cys Ser Leu Phe Ala Pro Val Cys
        50                  55                  60

Leu Asp Asp Leu Asp Glu Thr Ile Gly Pro Cys His Ser Leu Cys Met
65                  70                  75                  80

Gly Val Lys Asp Arg Cys Ala Pro Val Met Ser Ala Phe Gly Phe Pro
                85                  90                  95

Trp Pro Asp Met Leu Glu Cys Asp Arg Phe Pro Gly Asp Asn Asp Leu
                100                 105                 110

Cys

<210> SEQ ID NO 25
<211> LENGTH: 75
<212> TYPE: PRT
<213> ORGANISM: synthetic construct

<400> SEQUENCE: 25

Cys Pro Ile Ile Pro Leu Cys Ile Tyr Asn Thr Met Pro Asn Leu Leu
1               5                   10                  15

Gly His Gly Ala Gly Leu Glu Val His Gly Phe Pro Leu Val Cys Ser
                20                  25                  30
```

```
Pro Leu Phe Phe Leu Cys Ser Met Tyr Ala Pro Cys Leu Pro Ile Pro
         35                  40                  45

Pro Cys Arg Ser Leu Cys Glu Arg Ala Gly Cys Glu Pro Leu Met Phe
     50                  55                  60

Gly Phe Trp Pro Glu Leu Cys Phe Pro Gly Cys
 65                  70                  75

SEQ ID NO 26
LENGTH: 2124
<212> TYPE: DNA
<213> ORGANISM: Homo sapiens

<400> SEQUENCE: 26
gaattctcag gaattcgagg tagaaggtgg cagagagact tctgttcctg ggggccgagc      60
tgttgtgctg ataccgtcct cttggcgtct gccctagtgg ggacccttga ttttaacttg     120
aagttcctgg actgggtcta accttagcat gtgtgcctga gtgatggact tggtatttac     180
accagccacg ctgataagtg cacatgtgtt tttaatgttt tggctttcca caccacaaac     240
acacagatgt gctgtcgccc gggctaggac ttgagtaggg ttttttctat taaatatata     300
ttatatattt aaaaaagtgt cctcccagag ctaataccgt tgctagcagc tcttcctgcc     360
gccacaccgg gcaaagtcca cccactgccc cagtgttgag ggccaccatg ggcggcccca     420
cctggagagg tgctgctcac agcaaacagc tccaactgcg ccttcgcctc gccttccagg     480
gagcccagcc aggcccactg gtatttacaa gcagacctcc ctcgcttca gccttcctga     540 accctgtta gttgggaaac cacctgtctg caccgcagct agagaaccga ggagaggagc     600
cgctagtcta aagggctgtt ggttgaaatt aggaagcagt gtaaagaaaa agaaaaaaaa     660
agtttgggag gccaaggcag gagcatcacc tgaggtcagc agttcgagac cagcctggct     720
aacgtggtga acccccgtct ctactaaaaa tacaaaaaat tagcgggggc gtggtggcac     780
gcggctgtaa tcccagctac tcgggaggct gaggcaggag aatggcttga acccgggagg     840
cggaggaagc agtcacggag atagcgccat tgcactccag cttaggcaac aagagagcga     900
aacttcgtca aaaaaaaaaa gtcttcataa tttcatgggt ttgcaagtat gatccaggct     960
ccccgcttct ctgcaagcca atgcgagtta attacagcgt ccgccctggt ctctctccac    1020
cccacgccgt gatccattcc ccttcttttt ctcccctgt cttttcctac tcccccttt     1080 atttatgtat ttttggtttt gtttttttaag gggtgttgag ccgcgtctgg ttctagtaaa    1140
ccgaacccgc tcgcgaggga ggcgattggc tcccgcgccg gtgacggacg tggtaacgag    1200
tgcggctcgc cccgccggga gctgattggc tgcgcgggc ggctccgagg gctcggccgt    1260
aggagccccg cgcactccag ccctgcagcc tccgagtca gtgccgcgcg cccgccgccc    1320
cgcgccttcc tgctcgccgc acctccggga gccggggcgc acccagcccg cagcgccgcc    1380
tccccgcccg cgccgcctcc gaccgcaggc cgagggccgc cactggccgg ggggaccggg    1440
cagcagcttg cggccgcgga gccgggcaac gctgggact cgccttttg tccccggagg     1500 tccctggaag tttgcggcag gacgcgcgcg ggaggcggc ggaggcagcc ccgacgtcgc    1560
ggagaacagg gcgcagagcc ggcatgggca tcgggcgcac ggaggggggc gccgcgggg    1620 cagccctggg cgtgctgctg gcgctgggcg gcgcttctgg ccgtgggctc ggcagcgagt    1680
acgactacgt gagcttccag tcggacatcg gcccgtacca gagcgggcgc ttctacacca    1740
agccacctca gtgcgtggac atcccgcgcg acctgcggct gtgccacaac gtgggctaca    1800
agaagatggt gctgcccaac ctgctggagc acgagaccat ggcggaggtg aagcagcagg    1860
```

-continued

| | |
|---|---|
| ccagcagctg ggtgcccctg ctcaacaaga actgccacgc cgggcaccca ggtcttcctc | 1920 |
| tgctcgctct cgcgcccgtc tgcctggacc ggcccatcta cccgtgtcgc tggctctgcg | 1980 |
| aggccgtgcg cgactcgtgc gagccggtca tgcagttctt cggcttctac tggcccgaga | 2040 |
| tgcttaagtg tgacaagttc cccgaggggg acgtctgcat cgccatgacg ccgcccaatg | 2100 |
| ccaccgaagc ctccaagccc caag | 2124 |

<210> SEQ ID NO 27
<211> LENGTH: 4500
<212> TYPE: DNA
<213> ORGANISM: Homo sapiens

<400> SEQUENCE: 27

| | |
|---|---|
| ctcggccgta ggagccccgc gcactccagc cctgcagcct ccggagtcag tgccgcgcgc | 60 |
| ccgccgcccc gcgccttcct gctcgccgca cctccgggag ccggggcgca cccagcccgc | 120 |
| agcgccgcct ccccgcccgc gccgcctccg accgcaggcc gagggccgcc actggccggg | 180 |
| gggaccgggc agcagcttgc ggccgcgag ccggcaacg ctggggactg cgccttttgt | 240 |
| ccccggaggt ccctggaagt tgcggcagg acgcgcgcg ggaggcggcg gaggcagccc | 300 |
| cgacgtcgcg gagaacaggg cgcagagccg gcatgggcat cgggcgcagc gagggggggcc | 360 |
| gccgcggggc agccctgggc gtgctgctgg cgctgggcgc ggcgcttctg gccgtgggct | 420 |
| cggccagcga gtacgactac gtgagcttcc agtcggacat cggcccgtac cagagcgggc | 480 |
| gcttctacac caagccacct cagtgcgtgg acatccccgc ggacctgcgg ctgtgccaca | 540 |
| acgtgggcta caagaagatg gtgctgccca acctgctgga gcacgagacc atggcggagg | 600 |
| tgaagcagca ggccagcagc tgggtgcccc tgctcaacaa gaactgccac gccggcaccc | 660 |
| aggtcttcct ctgctcgctc ttcgcgcccg tctgcctgga ccggcccatc tacccgtgtc | 720 |
| gctggctctg cgaggccgtg cgcgactcgt gcgagccggt catgcagttc ttcggcttct | 780 |
| actggcccga gatgcttaag tgtgacaagt tccccgaggg ggacgtctgc atcgccatga | 840 |
| cgccgcccaa tgccaccgaa gcctccaagc ccaaggcac aacggtgtgt cctccctgtg | 900 |
| acaacgagtt gaaatctgag gccatcattg aacatctctg tgccagcgag tttgcactga | 960 |
| ggatgaaaat aaaagaagtg aaaaagaaa atggcgacaa gagattgtc cccaagaaga | 1020 |
| agaagcccct gaagttgggg cccatcaaga agaaggacct gaagaagctt gtgctgtacc | 1080 |
| tgaagaatgg ggctgactgt ccctgccacc agctggacaa cctcagccac cacttcctca | 1140 |
| tcatgggccg caaggtgaag agccagtact tgctgacggc catccacaag tgggacaaga | 1200 |
| aaaacaagga gttcaaaaac ttcatgaaga aatgaaaaa ccatgagtgc ccacctttc | 1260 |
| agtccgtgtt taagtgattc tcccggggc agggtgggga gggagcctcg ggtggggtgg | 1320 |
| gagcgggggg gacagtgccc cggaacccg tgggtcaca cacacgcact cgcctgtca | 1380 |
| gtagtggaca ttgtaatcca gtcggcttgt tcttgcagca ttcccgctcc cttccctcca | 1440 |
| tagccacgct ccaaacccca gggtagccat ggccgggtaa agcaagggcc atttagatta | 1500 |
| ggaaggtttt taagatccgc aatgtggagc agcagccact gcacaggagg aggtgacaaa | 1560 |
| ccatttccaa cagcaacaca gcccactaaaa cacaaaaagg gggattgggc ggaaagtgag | 1620 |
| agccagcagc aaaaactaca ttttgcaact tgttggtgtg gatctattgg ctgatctatg | 1680 |
| cctttcaact agaaaattct aatgattggc aagtcacgtt gttttcaggt ccagagtagt | 1740 |
| ttctttctgt ctgctttaaa tggaaacaga ctcataccac acttacaatt aaggtcaagc | 1800 |
| ccagaaagtg ataagtgcag ggaggaaaag tgcaagtcca ttatgtaata gtgacagcaa | 1860 |

```
agggaccagg ggagaggcat tgccttctct gcccacagtc tttccgtgtg attgtctttg    1920
aatctgaatc agccagtctc agatgcccca aagtttcggt tcctatgagc ccggggcatg    1980
atctgatccc caagacatgt ggaggggcag cctgtgcctg cctttgtgtc agaaaaagga    2040
aaccacagtg agcctgagag agacggcgat tttcgggctg agaaggcagt agttttcaaa    2100
acacatagtt aaaaagaaa caaatgaaaa aaatttttaga acagtccagc aaattgctag    2160
tcagggtgaa ttgtgaaatt gggtgaagag cttaggattc taatctcatg ttttttcctt    2220
ttcacatttt taaagaaca atgacaaaca cccacttatt tttcaaggtt ttaaaacagt    2280
ctacattgag catttgaaag gtgtgctaga acaaggtctc ctgatccgtc cgaggctgct    2340
tcccagagga gcagctctcc ccaggcattt gccaagggag gcggatttcc ctggtagtgt    2400
agctgtgtgg ctttccttcc tgaagagtcc gtggttgccc tagaacctaa cacccctag    2460 caaaactcac agagctttcc gttttttctt ttcctgtaaa gaacatttc ctttgaactt    2520 gattgcctat ggatcaaaga aattcagaac agcctgcctg tcccccgca cttttacat    2580 atatttgttt catttctgca gatggaaagt tgacatgggt ggggtgtccc catccagcga    2640
gagagtttca aaagcaaaac atctctgcag tttttcccaa gtaccctgag atacttccca    2700
aagcccttat gtttaatcag cgatgtatat aagccagttc acttagacaa ctttaccctt    2760
cttgtccaat gtacaggaag tagttctaaa aaaatgcat attaatttct tcccccaaag    2820
ccggattctt aattctctgc aacactttga ggacatttat gattgtccct ctgggccaat    2880
gcttataccc agtgaggatg ctgcagtgag gctgtaaagt ggcccctgc ggccctagcc    2940 tgacccggag aaaggatggt agattctgtt aactcttgaa gactccagta tgaaaatcag    3000
catgcccgcc tagttaccta ccggagagtt atcctgataa attaacctct cacagttagt    3060
gatcctgtcc ttttaacacc ttttttgtgg ggttctctct gacctttcat cgtaaagtgc    3120
tggggacctt aagtgatttg cctgtaattt tggatgatta aaaatgtgt atatatatta    3180 gctaatcaga aatattctac ttctctgttg tcaaactgaa attcagagca agttcctgag    3240
tgcgtggatc tgggtcttag ttctggttga ttcactcaag agttcagtgc tcatacgtat    3300
ctgctcattt tgacaaagtg cctcatgcaa ccgggccctc tctctgcggc agagtcctta    3360 gtggagggt ttacctggaa catagtagtt accacagaat acggaagagc aggtgactgt    3420
gctgtgcagc tctctaaatg ggaattctca ggtaggaagc aacagcttca gaaagagctc    3480
aaaataaatt ggaaatgtga atcgcagctg tgggttttac caccgtctgt ctcagagtcc    3540
caggaccttg agtgtcatta gttactttat tgaaggtttt agacccatag cagctttgtc    3600
tctgtcacat cagcaatttc agaaccaaaa gggaggctct ctgtaggcac agagctgcac    3660
tatcacgagc ctttgttttt ctccacaaag tatctaacaa aaccaatgtg cagactgatt    3720
ggcctggtca ttggtctccg agagaggagg tttgcctgtg atttcctaat tatcgctagg    3780
gccaaggtgg gatttgtaaa gctttacaat aatcattctg gatagagtcc tgggaggtcc    3840
ttggcagaac tcagttaaat ctttgaagaa tatttgtagt tatcttagaa gatagcatgg    3900
gaggtgagga ttccaaaaac attttatttt taaaatatcc tgtgtaacac ttggctcttg    3960
gtacctgtgg gttagcatca agttctcccc agggtagaat tcaatcagag ctccagtttg    4020
catttggatg tgtaaattac agtaatccca tttcccaaac ctaaaatctg ttttttctcat    4080 cagactctga gtaactggtt gctgtgtcat aacttcatag atgcaggagg ctcaggtgat    4140
ctgtttgagg agagcaccct aggcagcctg cagggaataa catactggcc gttctgacct    4200
```

-continued

```
gttgccagca gatacacagg acatggatga aattcccgtt tcctctagtt tcttcctgta   4260
gtactcctct tttagatcct aagtctctta caaaagcttt gaatactgtg aaaatgtttt   4320
acattccatt tcatttgtgt tgtttttta actgcatttt accagatgtt ttgatgttat    4380
cgcttatgtt aatagtaatt cccgtacgtg ttcattttat tttcatgctt tttcagccat   4440
gtatcaatat tcacttgact aaagtcactc aattaatcaa taaaaaaaaa aaaaaaaaa    4500
```